US012616667B2

(12) United States Patent
Ford et al.

(10) Patent No.: US 12,616,667 B2
(45) Date of Patent: *May 5, 2026

(54) COMPOSITIONS AND METHODS FOR IMPROVING NEUROLOGICAL DISEASES AND DISORDERS

(71) Applicant: CURASEN THERAPEUTICS, INC., San Carlos, CA (US)

(72) Inventors: Anthony P. Ford, Los Altos Hills, CT (US); Gabriel Vargas, San Carlos, CA (US); Wei Chen, Saratoga, CA (US); Renee S. Martin, San Carlos, CA (US)

(73) Assignee: CuraSen Therapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/986,797

(22) Filed: Nov. 14, 2022

(65) Prior Publication Data

US 2023/0157974 A1 May 25, 2023

Related U.S. Application Data

(60) Provisional application No. 63/279,585, filed on Nov. 15, 2021.

(51) Int. Cl.

| | |
|---|---|
| ***A61K 31/138*** | (2006.01) |
| ***A61K 31/05*** | (2006.01) |
| ***A61P 25/28*** | (2006.01) |
| ***C07D 213/61*** | (2006.01) |

(52) U.S. Cl.

CPC ............ *A61K 31/138* (2013.01); *A61K 31/05* (2013.01); *A61P 25/28* (2018.01); *C07D 213/61* (2013.01)

(58) Field of Classification Search

CPC ..... C07D 213/61; A61P 25/28; A61K 31/138; A61K 31/05

See application file for complete search history.

(56) References Cited

U.S. PATENT DOCUMENTS

| | | | | |
|---|---|---|---|---|
| 7,135,497 | B1 | 11/2006 | Zeman et al. | |
| 7,528,175 | B2 * | 5/2009 | Bond | A61K 31/138 514/649 |
| 9,320,724 | B2 | 4/2016 | Salehi et al. | |
| 9,539,221 | B2 | 1/2017 | Bond | |
| 10,947,196 | B2 | 3/2021 | Ford et al. | |
| 11,040,944 | B2 | 6/2021 | Ford et al. | |
| 11,607,395 | B2 * | 3/2023 | Ford | A61K 31/138 |
| 2004/0034087 | A1 | 2/2004 | Kilian et al. | |
| 2007/0021421 | A1 | 1/2007 | Hampton et al. | |
| 2008/0033027 | A1 | 2/2008 | Bascomb et al. | |
| 2010/0240764 | A1 | 9/2010 | Greb et al. | |
| 2012/0263764 | A1 | 10/2012 | Watson | |
| 2014/0235726 | A1 | 8/2014 | Salehi et al. | |
| 2014/0256822 | A1 * | 9/2014 | McCarty | A61K 9/006 514/653 |
| 2020/0308114 | A1 | 10/2020 | Ford et al. | |
| 2020/0308115 | A1 * | 10/2020 | Ford | C07D 413/04 |
| 2021/0121444 | A1 | 4/2021 | Ford | |
| 2021/0186897 | A1 | 6/2021 | Ford et al. | |
| 2021/0251559 | A1 | 8/2021 | Ford | |
| 2021/0308077 | A1 | 10/2021 | Scherzer | |

FOREIGN PATENT DOCUMENTS

| | | | |
|---|---|---|---|
| EP | 3946329 | | 2/2022 |
| EP | 4161495 | | 4/2023 |
| EP | 4161496 | A1 | 4/2023 |
| WO | WO 2019/241744 | A1 | 12/2019 |

OTHER PUBLICATIONS

Lodeweyckx et al., "Safety, Tolerability and Cerebral Blood Flow After Single Doses of the Beta2-Agonist, Clenbuterol, in Patients with Mild Cognitive Impairment or Parkinson's Disease", 2020, Journal of Prevention of Alzheimer's Disease, 8 (Suppl 1), S87-S88 (Year: 2020).*

Drugs.com, "Albuterol Dosage", first available 2010, Drugs.com (Year: 2010).*

Drugs.com, "Albuterol Inhalation", first available 2010, Drugs.com (Year: 2010).*

Chen et al., "Comorbidity and dementia: A nationwide survey in Taiwan", 2017, PLoS One, 12, pp. 1-12 (Year: 2017).*

Drugs.com, "Nadolol Dosage", 2023, Drugs.com (Year: 2023).*

Jessen et al., "Beta2-adrenergic agonist clenbuterol increases energy expenditure and fat oxidation, and induces mTOR phosphorylation in skeletal muscle of young healthy men", 2020, Drug Testing and Analysis, 12, pp. 610-618 (Year: 2020).*

Lodeweyckx et al., "Safety, Tolerability and Cerebral Blood Flow After Single Doses of the Beta2-Agonist, Clenbuterol, in Patients with Mild Cognitive Impairment or Parkinson's Disease", 2021, Journal of Prevention of Alzheimer's Disease, 8 (Suppl 1), S87-S88 (correction to publishing date) (Year: 2021).*

Wheeldon et al., "The effects of lower than conventional doses of oral nadolol on relative beta1/beta2-adrenoceptor blockade", Br J Clin Pharmac, 1994, 38, pp. 103-108 (Year: 1994).*

Nomura et al., "Clinical significance of REM sleep behavior disorder in Parkinson's disease", 2013, Sleep Medicine, 14, pp. 131-135 (Year: 2013).*

Ridler, "Asthma drug could protect against PD", Nature Reviews Neurology, 2017, 1 pg. (Year: 2017).*

Nathan, "Diabetes: Advances in Diagnosis and Treatment", JAMA, 2015, 314, pp. 1052-1062 (Year: 2015).*

(Continued)

*Primary Examiner* — Jeffrey H Murray
*Assistant Examiner* — Madeline E Braun
(74) *Attorney, Agent, or Firm* — DLA Piper LLP (US)

(57) ABSTRACT

In various aspects and embodiments provided are compositions and methods for identifying patients in need of improving cognition and/or treating a neurodegenerative disease in a patient and treating such patient. More specifically, the disclosure in some embodiments includes administration of a β-AR agonist (such as a β-agent) and a peripherally acting β-blocker (PABRA) to a patient in need thereof.

9 Claims, 15 Drawing Sheets

(56) References Cited

OTHER PUBLICATIONS

Yoon et al., "Rapid Screening of Blood-Brain Barrier Penetration of Drugs Using the Immobilized Artificial Membrane Phosphatidylcholine Column Chromatography", 2006, SLAS Discovery, 11, pp. 13-20 (Year: 2006).*

PCT International Search Report and Written Opinion in International Application No. PCT/US2021/048540, dated Dec. 7, 2021, 20 pages.

PCT International Search Report and Written Opinion in International Application No. PCT/US2023/22422, dated Aug. 16, 2023, 12 pages.

Teng et al., "Therapeutic effects of clenbyterol in a murine model of amyotrophic lateral sclerosis", Neuroscience Letters, Jan. 2006, 397(1-2):155-158.

Bartus et al., "β2-Adrenoceptor agonists as novel, safe and potentially effective therapies for Amyotrophic lateral sclerosis (ALS)", Neurobiol Dis, Jan. 2016, 85: 11-24.

Gurney, "The use of transgenic mouse models of amyotrophic lateral sclerosis in preclinical drug studies", J Neurol Sci, Oct. 1997, 152(Suppl 1):S-67-73.

Kobayashi et al., "Effects of Early Albuterol (Salbutamol) Administration on the Development of posttraumatic Stress Symptoms", Psychiatry Research, 2011, 185(1-2): 296-298.

PCT International Search Report and Written Opinion in International Application No. PCT/US2023/84629.

Wang et al., "Determination of the Competitive Adsorption Isotherms of Nadolol Enantiomers by an Improved h-Root Method", Industrial & Engineering Chemistry Research, 2003, 42(24): 6171-6180.

EP; Extended European Search Report issued on Aug. 26, 2024 in European Application No. 21865003.4.

US; Office Action issued on Aug. 23, 2024 in U.S. Appl. No. 18/198,191.

Tartaglia et al., "Differentiation between primary lateral sclerosis and amyotrophic lateral sclerosis: examination of symptoms and signs at disease onset and during follow-up," Arch Neurol. Feb. 2007.; 64(2); 2007. (Abstract only).

Notification of Transmittal of the International Search Report and the Written Opinion of International Application No. PCT/US2025/018417 issued Jun. 6, 2025, 15 pages.

* cited by examiner

| | | | | | | | | | | | |
|---|---|---|---|---|---|---|---|---|---|---|---|
| NADOLOL | 2 mg | 20mg | | 2 mg | 20mg | | 2 mg | 20mg | | 2 mg | 20mg |
| COMPOUND 03-5 | 3 mg | 12 mg | | 3 mg | 12 mg | | 3 mg | 12 mg | | 3 mg | 12 mg |

COMPOSITIONS AND METHODS FOR IMPROVING NEUROLOGICAL DISEASES AND DISORDERS

CROSS-REFERENCE TO RELATED APPLICATIONS

This application claims benefit of priority under 35 U.S.C. § 119(e) of U.S. Ser. No. 63/279,585, filed Nov. 15, 2021, the entire contents of which is incorporated herein by reference in its entirety.

FIELD OF THE INVENTION

The present disclosure relates generally to compositions and methods for improving cognition and/or treating a neurodegenerative disease in a patient.

BACKGROUND

United States Patent Application Publication Number 20130096126 discloses "a method for enhancing learning or memory of both in a mammal having impaired learning or memory or both from a neuro-degenerative disorder, which entails the step of administering at least one compound or a salt thereof which is a $\beta_1$-ARenergic receptor agonist, partial agonist or receptor ligand in an amount effective to improve the learning or memory or both of said mammal."

United States Patent Application Publication Number 20140235726 discloses "a method of improving cognition in a patient with Down syndrome, which entails administering one or more $\beta_2$ adrenergic receptor agonists to the patient in an amount and with a frequency effective to improve cognition of the patient as measured by contextual learning tests."

United States Patent Application Publication Number 20160184241 discloses "a method of improving cognition in a patient with Down syndrome, which entails intranasally administering one or more $\beta_2$-AR agonists or pharmaceutically-acceptable salts of either or both to the patient in an amount and with a frequency effective to improve cognition of the patient as measured contextual learning tests."

PCT Application Publication Number WO2017115873 discloses "a combination of two or more compounds selected from the group consisting of compounds represented by the Compound No. 1-130, a preventive or therapeutic agent for Alzheimer's disease (AD)" and states "In an attempt to achieve the aforementioned object, the present inventors have screened an existing drug library consisting of 1280 kinds of pharmaceutical compounds approved by the Food and Drug Administration (FDA) in America by using nerve cells induced to differentiate from iPS cells derived from AD patients, and extracted 129 kinds (including one kind of concomitant drug) of compounds that improve Aβ pathology in the nerve cells as candidate therapeutic drugs for AD."

PCT Application Publication Number WO2006108424 states "[t]he invention furthermore relates to dermatological compositions without skin sensitization properties and which contain an enantiomerically pure enantiomer of a $\beta_2$ adrenoceptor agonist.

PCT Application Publication Number WO2018195473 provides "methods of treating a subject who has a synucleinopathy (e.g., Parkinson's disease) that include administering to a subject in need of such treatment therapeutically effective amounts of a $\beta_2$-adrenoreceptor agonist and at least one therapeutic agent."

PCT Application WO2019241736 (Ford) discloses "compositions and methods for improving cognition and/or treating a neurodegenerative disease in a patient"and that the methods may" . . . include identifying a patient in need of, or desiring improvement of, cognitive function and/or treatment of a neurodegenerative disease and administering to the patient a β agonist and optionally a peripherally acting β-blocker (PABRA)." Ford further discloses that "[e] xamples of selective peripherally acting β-blockers (PABRA) that may in certain embodiments be used in the methods disclosed herein include nadolol, atenolol, sotalol and labetalol."

PCT Application WO2018195473 (Sherzer) discloses "[a] method of treating a subject who has a synucleinopathy, the method comprising: administering to a subject in need of such treatment therapeutically effective amounts of a β2-adrenoreceptor agonist and at least one therapeutic agent selected from the group consisting of: a synucleinopathy therapeutic agent, a β2-adrenoreceptor antagonist and a health supplement, . . . to thereby treat Parkinson's disease in the subject . . . wherein the β2-adrenoreceptor antagonist is selected from the group consisting of carteolol, carvedilol, labetalol, nadolol, penbutolol, pindolol, sotalol, timolol, oxprenolol and butaxamine."

SUMMARY

In one aspect, a method for improving cognitive function and/or treating a neurodegenerative disease is provided wherein the method includes administering a therapeutically effective amount of a β-AR agonist (such as a β-agent) and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of a β-AR agonist (such as a 1-agent) and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of a β-AR agonist (such as a β-agent) and a sub-therapeutic dose of a peripherally acting β-blocker (PABRA) to a patient.

The term "β-agent" as used herein means a compound with a structure of Formula (I), Formula (I''), Formula (II), Formula (III), Formula (I'), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), or Formula (XXV') as provided herein; or an optically pure stereoisomer, pharmaceutically acceptable salt, solvate, or prodrug thereof. In various embodiments, the β-agent is a compound provided in Table 1 herein. In some embodiments, the β-agent is Compound 03-5, or an optically pure stereoisomer, pharmaceutically acceptable salt, solvate, or prodrug thereof. In certain embodiments, a β-agent as disclosed herein is an agonist, partial agonist or antagonist of an adrenergic receptor; in some embodiments the 1-agent is a β-AR agonist, in some embodiments the β-agent is a β1-adrenergic receptor agonist, β2-adrenertic receptor agonist or non-selective β1/β2-adrenergic receptor agonist; in some embodiments the β-agent is a β1-adrenergic receptor agonist; in some embodiments the β-agent is a β2-adrenergic receptor agonist; in some embodiments the β-agent is a non-selective β1/β2-adrenergic agonist.

In some embodiments a β-agent is a compound according to Formula (I) or an optically pure stereoisomer, pharmaceutically acceptable salt, solvate, prodrug thereof Formula (I)

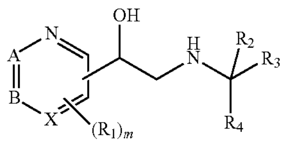

In some embodiments, each A, B, and X is independently a nitrogen or carbon. In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)— cycloalkyl, unsubstituted or substituted —(C═O)-aryl, unsubstituted or substituted —(C═O)— heteroaryl, unsubstituted or substituted aryl, and unsubstituted or substituted heteroaryl. In some embodiments, m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

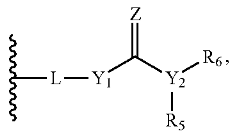

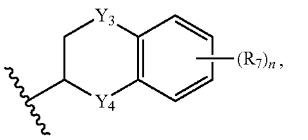

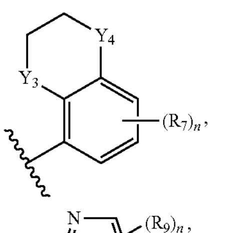

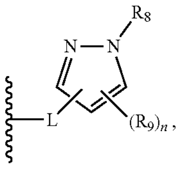

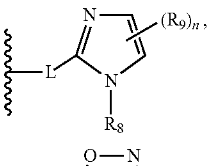

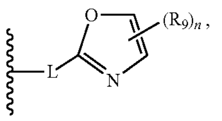

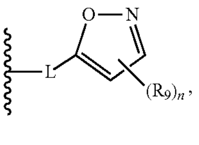

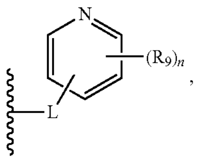

-continued

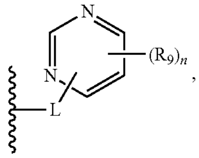

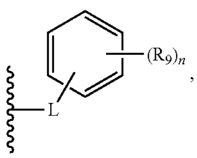

and

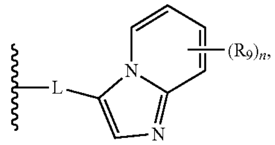

or $R_2$ and $R_3$ together with the carbon form an unsubstituted or substituted 3-7 membered cycloalkyl or heterocycle ring.

In some embodiments, L is a C1-C5 alkyl linker optionally substituted, each $Y_1$, $Y_2$, $Y_3$, and $Y_4$ is independently a covalent bond, a carbon, an oxygen, or a nitrogen, optionally substituted with hydrogen, unsubstituted or substituted alkyl, or unsubstituted or substituted cycloalkyl, and Z is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

Also disclosed herein is a β-agent that is a compound according to Formula (II) or an optically pure stereoisomer, pharmaceutically acceptable salt, solvate, or prodrug thereof Formula (II)

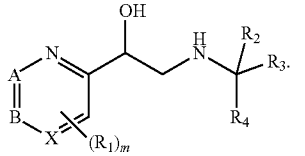

In some embodiments, each A, B, and X is independently a nitrogen or carbon. In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)— cycloalkyl, unsubstituted or substituted —(C═O)-aryl, unsubstituted or substituted —(C═O)— heteroaryl, unsubstituted or substituted aryl, and unsubstituted or substituted heteroaryl. In some embodiments, m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, un-substituted or substituted alkenyl, unsubstituted or substituted alkynyl, unsubstituted or substituted cycloalkyl, unsubstituted or substituted aryl, unsubstituted or substituted heteroaryl,

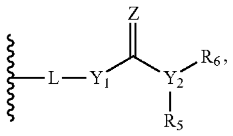 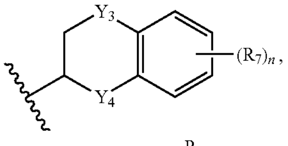

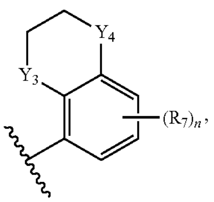 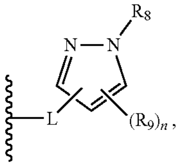

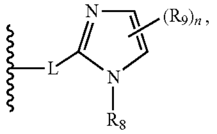 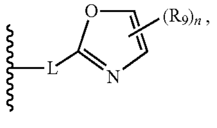

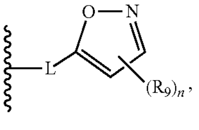 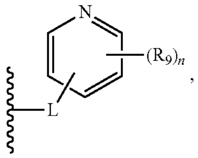

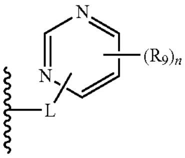 , 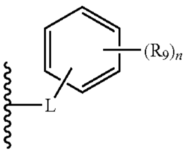 , and

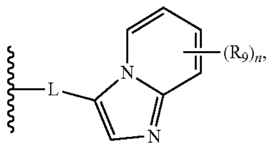

or $R_2$ and $R_3$ together with the carbon form an unsubstituted or substituted 3-7 membered cycloalkyl or heterocycle ring.

In some embodiments, L is a C1-C5 alkyl linker optionally substituted, each $Y_1$, $Y_2$, $Y_3$, and $Y_4$ is independently a covalent bond, a carbon, an oxygen, or a nitrogen, optionally substituted with hydrogen, unsubstituted or substituted alkyl, or unsubstituted or substituted cycloalkyl, and Z is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

In further embodiments, a β-agent is a compound according to Formula (III) or an optically pure stereoisomer, pharmaceutically acceptable salt, solvate, or prodrug thereof Formula (III)

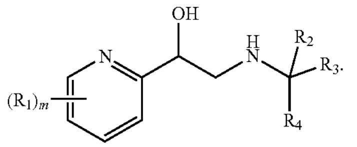

In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl. m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

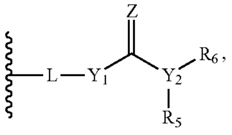 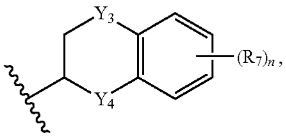

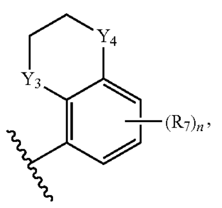 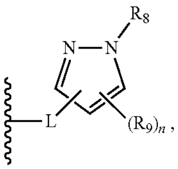

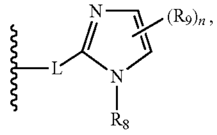 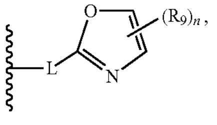

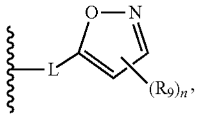 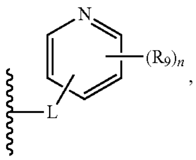

-continued

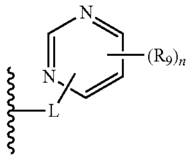

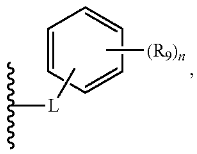

and

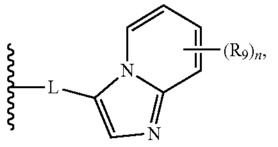

or $R_2$ and $R_3$ together with the carbon form an unsubstituted or substituted 3-7 membered cycloalkyl or heterocycle ring.

In some embodiments, L is a C1-C5 alkyl linker optionally substituted, each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl, and Y is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

Further disclosed herein is a compound according to Formula (I'):

Formula (I')

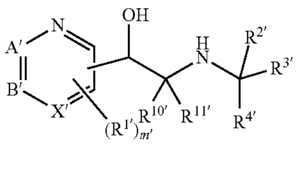

or a pharmaceutically acceptable salt thereof, wherein:

A', B', and X' are each independently nitrogen or carbon;

each $R^{1'}$ is independently halogen, —R', —CN, —$NO_2$, —$SF_5$, —$OR^x$, —$NR^x_2$, —$NHR^x$, —$SO_2R'$, —C(O)R', —C(O)NR'$_2$;

each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each $R^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

$R^{2'}$, $R^{3'}$, and $R^{4'}$ are each independently halogen, —R', —CN, —$NO_2$, —OR', —NR'$_2$,

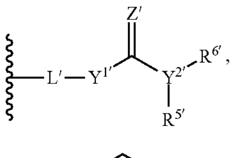

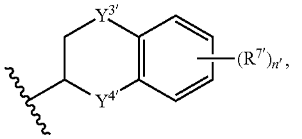

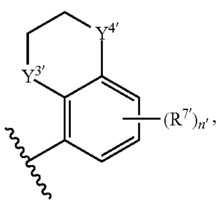

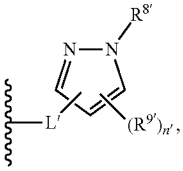

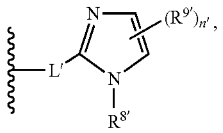

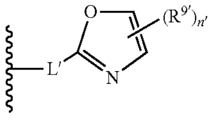

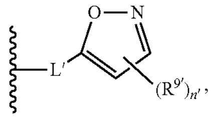

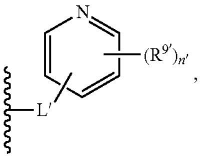

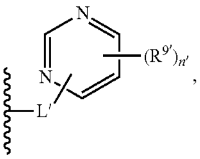

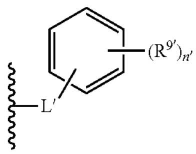

, or

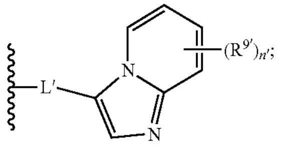

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted $C_{1-5}$ alkylene;

$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

$R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, —$NO_2$, —$NR'_2$, or —OR';

n' is an integer selected from 0 to 4;

$R^{8'}$ is hydrogen, —CN, optionally substituted alkyl, or an optionally substituted aryl ring; and each $R^{9'}$ is independently hydrogen, halogen, —CN, —$OR^x$, —$NR'_2$, or optionally substituted alkyl; and $R^{10'}$ and $R^{11'}$ are each independently hydrogen or optionally substituted $C_{1-2}$ aliphatic.

Further disclosed herein is a compound according to Formula (I"):

Formula (I")

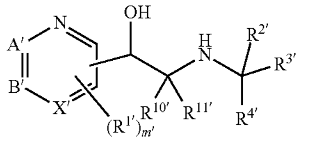

or a pharmaceutically acceptable salt thereof, wherein:

A', B', and X' are each independently nitrogen or carbon;

each $R^{1'}$ is independently halogen, —R', —CN, —$NO_2$, —$SF_5$, —$OR^x$, —$NR^x_2$, —$NHR^x$, —$SO_2R'$, —C(O)R', —C(O)$NR'_2$, —NR'C(O)R', —NR'$CO_2R'$, or —$CO_2R'$;

each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each $R^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

$R^{2'}$, $R^{3'}$, and $R^{4'}$ are each independently halogen, —R', —CN, —$NO_2$, —OR', —$NR'_2$,

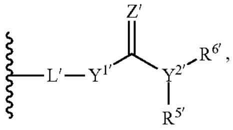

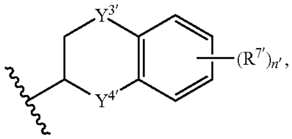

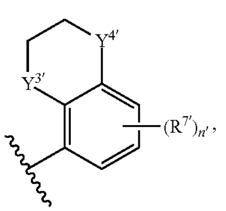

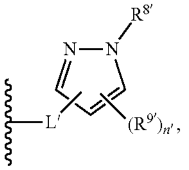

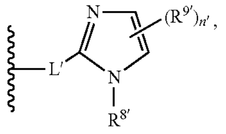

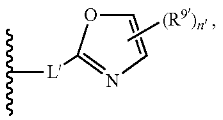

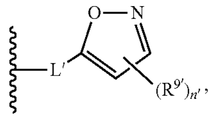

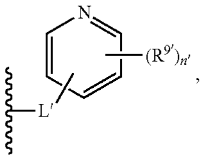

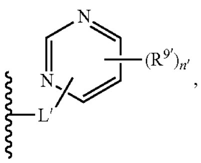

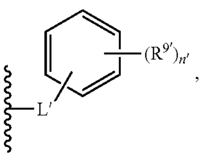

, or

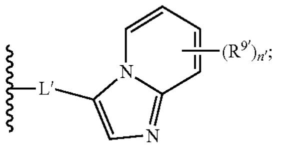

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted $C_{1-5}$ alkylene;

$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

$R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, —$NO_2$, —$NR'_2$, or —OR';

n' is an integer selected from 0 to 4;

$R^{8'}$ is hydrogen, —CN, optionally substituted alkyl, or an optionally substituted aryl ring; and each $R^{9'}$ is independently hydrogen, halogen, —CN, —OR', —$NR'_2$, or optionally substituted alkyl; and $R^{10'}$ and $R^{11'}$ are each independently hydrogen or optionally substituted $C_{1-2}$ aliphatic.

In some embodiments a β-agent is a compound with the following structure:

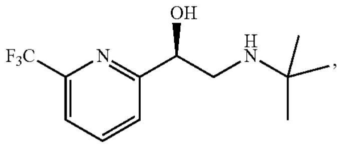

or a pharmaceutically acceptable salt thereof.

In some embodiments a β-agent is a compound with the following structure:

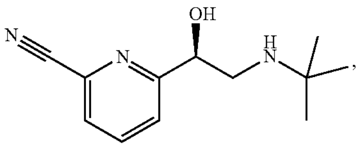 [SMILES: CC(C)(C)NC[C@H](O)c1cccc(C#N)n1]

or a pharmaceutically acceptable salt thereof.

In some embodiments a β-agent is a compound with the following structure:

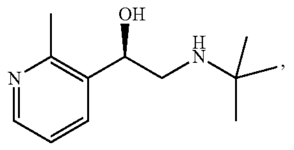

or a pharmaceutically acceptable salt thereof.

In one aspect, a method for improving cognitive function and/or treating a neurodegenerative disease is provided wherein the method includes administering a therapeutically effective amount Compound 03-5, or an optically pure stereoisomer, pharmaceutically acceptable salt, solvate, or prodrug thereof, and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of Compound 03-5 and a sub-therapeutic dose of a peripherally acting β-blocker (PABRA) to a patient. In one embodiment, a method for improving cognitive function and/or treating a neurodegenerative disease is provided wherein the method includes administering a therapeutically effective amount of Compound 03-5 and a sub-therapeutic dose of a peripherally acting β-blocker (PABRA) to a patient.

As used herein, the term "patient" can be used interchangeably with "subject" and refers to an individual that receives a composition or treatment as disclosed herein or is subjected to a method of the disclosure. In certain embodiments a patient or subject may have been diagnosed with a condition, disease or disorder and a composition or method of the disclosure is administered/applied with the intention of treating condition, disease or disorder. In some embodiments a patient or subject is any individual that receives a composition or method of the disclosure and has not necessarily been diagnosed with any particular condition, disease or disorder. In some embodiments, a patient or subject is any individual desiring an improvement in cognition or cognitive function. In various embodiments, a patient or subject may be a human or any other animal (canine, feline, etc.).

In some embodiments of the methods and compositions provided herein, the purpose of the PABRA is not to directly treat a specific disease indication or condition, but rather to offset undesirable peripheral side effects of a β-AR agonist (such as a β-agent) (e.g., the PABRA may be administered to reduce, restrict, or counter any adverse effect(s) of the β-AR agonist (such as a β-agent), such as cardiac effects or performance-enhancing effects, thus, reducing the likelihood of abuse), and therefore in some embodiments, the PABRA dose may be lower than that generally used in previously approved therapeutic situations and indications where the PABRA is intended to directly treat a specific disease. As used herein, the term "sub-therapeutic dose" means a dose of an agent that is less than the minimum dose that is independently effective to treat a specific disease indication. In some embodiments, a sub-therapeutic dose is less than the lowest dose for which an agent is independently approved to treat any specific disease indication by a regulatory agency. In some embodiments, a sub-therapeutic dose is less than the lowest dose for which an agent is approved to treat any specific disease indication by the United States FDA. In some embodiments, a sub-therapeutic dose is less than the lowest dose for which an agent is approved to treat any specific disease indication by a regulatory agency (such as the US FDA). In certain embodiments, a subtherapeutic dose of a PABRA is sufficient to off-set or counter one or more undesirable side effects of a β-AR agonist (such as a β-agent), but the dose is less than what would generally be administered to independently treat a disease or disorder. For example, in some embodiments a sub-therapeutic dose may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a dose that the agent is effective for, or approved for treating a specific disease indication. In certain embodiments, a sub-therapeutic dose for a PABRA may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% as compared to a dose that the agent is effective for, or approved for, treating a specific disease indication. For example, the PABRA nadolol at a dose of 40 mg once daily is approved in the United States for treatment of hypertension and angina pectoris, therefore a sub-therapeutic dose of nadolol in certain embodiments would be a dose that is less than 40 mg daily; for example a sub-therapeutic dose of nadolol may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to the 40 mg daily dose; or in some embodiments a sub-therapeutic dose of nadolol may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% of a 40 mg daily dose. In some embodiments, the peripherally acting β-blocker (PABRA) is nadolol and is administered in a total daily dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments the aforementioned doses of nadolol are weekly doses, or are twice-weekly doses. Another example of a PABRA that could be used in the methods described herein is Atenolol. Atenolol approved for various indications including hypertension, angina pectoris prophylaxis, angina pectoris, and myocardial infarction at doses ranging from 25-200 mg once daily. Accordingly, a sub-therapeutic dose of atenolol in certain embodiments would be a dose that is less than 25 mg daily; for example a sub-therapeutic dose of atenolol may be 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a 25 mg daily dose; or in some embodiments a sub-therapeutic dose of atenolol may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% of a 25 mg daily dose. In some embodiments, the peripherally acting β-blocker (PABRA) is atenolol and is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments the aforementioned doses of atenolol are weekly doses, or are twice-weekly doses.

In certain embodiments, a PABRA as used herein may have relatively limited CNS (blood-brain barrier) penetration and thus be preferentially active in the periphery.

In certain embodiments of the methods and compositions disclosed herein, the β-AR agonist (such as a β-agent) is administered in a dose that is therapeutically effective in improving cognition and/or treating a neurodegenerative disease in a patient. In some embodiments, the β-AR agonist (such as a β-agent) can be administered at a dose of from about 0.01 to 100 mg. In some embodiments, the β-AR agonist (such as a β-agent) can be administered at a dose of from about 30 to 160 μg. In some embodiments, the β-AR agonist (such as a β-agent) can be administered at a dose of from about 50 to 160 μg. For some embodiments, the β-AR agonist (such as a β-agent) can be administered at a dose of from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments, the β-AR agonist (such as a β-agent) can be administered in a dose from 150 μg to 1 mg; or from 200 μg to 500 μg, or about 250 μg, or about 300 μg, or about 400 μg, or about 500 μg. In some embodiments, the β-AR agonist (such as a 1-agent) can be administered in a dose from 0.5-50 mg; or 1-25 mg; or 1-10 mg; or 10-20 mg; or 25-50 mg; or mg; or 2-8 mg; or about 1 mg; or about 2 mg; or about 3 mg; or about 4 mg, or about 5 mg; or about 6 mg; or about 7 mg; or about 8 mg; or about 10 mg; or abut 15 mg; or about 20 mg; or about 25 mg; or about 30 mg; or about 40 mg; or about 50 mg. In some embodiments of the aspects or embodiments provided herein the β-AR agonist (such as a β-agent) is administered in a dose that is from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. In some embodiments the aforementioned doses are daily doses, twice daily doses, weekly doses, or twice-weekly doses.

In some embodiments of any of the methods or compositions provided herein, the β-AR agonist (such as a β-agent) is administered in the morning. As used herein, the term "morning" means before 1 PM; or before noon; or before 11:30 AM; or before 11 AM; or before 10:30 AM; or before 10 AM; or before 9:30 AM; or before 9 AM; or before 8:30 AM; or before 8 AM; or within 30 mins from the time the subject awakes; or within 45 mins from time the subject awakes; or within 60 mins from the time the subject awakes; or within 90 mins from the time the subject awakes; or within 2 hours from the time the subject awakes; or within 2.5 hours from the time the subject awakes; or within 3 hours from the time the subject awakes; or within 3.5 hours from the time the subject awakes; or within 4 hours from the time the subject awakes; or within 5 hours from the time the subject awakes; or within 6 hours from the time the subject awakes; or or within 30 mins from the time the subject awakes; or within 45 mins from the time the subject awakes; or within 60 mins from the time the subject awakes; or within 90 mins from the time the subject awakes; or within 2 hours from the time the subject awakes; or within 2.5 hours from the time the subject awakes; or within 3 hours from the time the subject awakes; or within 3.5 hours from the time the subject awakes; or within 4 hours from the time the subject awakes; or within 5 hours from the time the subject awakes; or within 6 hours from the time the subject awakes; or before the subject eats after waking up; or at least 15 mins before the subject eats after waking up; or at least 30 mins before the subject eats after waking up; or at least 45 mins before the subject eats after waking up; or at least 1 hour before the subject eats after waking up.

In certain embodiments of the methods and compositions disclosed herein, the β-agent is Compound 03-5, or an optically pure stereoisomer, pharmaceutically acceptable salt, solvate, or prodrug thereof, and is administered in a dose that is therapeutically effective in improving cognition and/or treating a neurodegenerative disease in a patient. In some embodiments, Compound 03-5 can be administered at a dose of from about 0.01 to 100 mg. In some embodiments, Compound 03-5 can be administered at a dose of from about 30 to 160 μg. In some embodiments, the Compound 03-5 can be administered at a dose of from about 50 to 160 μg. For some embodiments, Compound 03-5 can be administered at a dose of from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments Compound 03-5 can be administered in a dose from 150 μg to 1 mg; or from 200 μg to 500 μg, or about 250 μg, or about 300 μg, or about 400 μg, or about 500 μg. In some embodiments, the Compound 03-05 can be administered in a dose from 0.5-50 mg; or 1-25 mg; or 3-20; or 1-20; or 1-10 mg; or 10-20 mg; or 25-50 mg; or mg; or 2-8 mg; or about 1 mg; or about 2 mg; or about 3 mg; or about 4 mg, or about 5 mg; or about 6 mg; or about 7 mg; or about 8 mg; or about 10 mg; or about 11; or about 12; or about 13; or about 14; or abut 15 mg; or about 20 mg; or about 25 mg; or about 30 mg; or about 40 mg; or about 50 mg. In some embodiments of the aspects or embodiments provided herein Compound 03-5 is administered in a dose that is from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg. In some embodiments the aforementioned doses are daily doses, twice daily doses, weekly doses, or twice-weekly doses.

For some embodiments the doses of any agent provided herein can be a total daily dose. In some embodiments the total daily dose as provided herein is achieved by dosing once daily, in some embodiments the total daily dose is achieved by dosing twice daily, and in yet other embodiments the total daily dose is achieved by dosing more than two times daily. In certain embodiments, the doses of any agent provided herein can be a dose administered weekly or twice weekly. For some embodiments, the therapeutically effective amount of R-agent and the sub-therapeutic dose of the peripherally acting β-blocker (PABRA) are administered for a period of weeks or more; or three weeks or more; or five weeks or more; or ten weeks or more; or twenty weeks or more; or a year or more.

In one aspect, a method for improving cognitive function and/or treating a neurodegenerative disease is provided wherein the method includes administering a therapeutically effective amount of a β-AR agonist (such as a β-agent) and a peripherally acting 1-blocker (PABRA) to a patient, wherein the peripherally acting β-blocker (PABRA) is administered in a dose of about 15 mg or less. In some embodiments, the peripherally acting β-blocker (PABRA; such as nadolol or atenolol) is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. For some embodiments where it is not indicated differently, the above-mentioned doses are a total daily dose. For some, the above-mentioned doses are a total weekly dose. For some embodiments, the therapeutically effective amount of 3-AR agonist (such as a β-agent) and the dose of the peripherally acting β-blocker (PABRA) are administered for a period of weeks or more.

In one aspect, a method for improving cognitive function and/or treating a neurodegenerative disease is provided wherein the method includes administering a therapeutically effective amount of Compound 03-5, or an optically pure stereoisomer, pharmaceutically acceptable salt, solvate, or prodrug thereof, and a peripherally acting β-blocker (PABRA) to a patient, wherein the peripherally acting β-blocker (PABRA) is administered in a dose of about 15 mg or less. In some embodiments, the peripherally acting β-blocker (PABRA; such as nadolol or atenolol) is administered in a dose of about 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. For some embodiments where it is not indicated differently, the above-mentioned doses are a total daily dose. For some, the above-mentioned doses are a total weekly dose. For some embodiments, the therapeutically effective amount of 3-AR agonist (such as a β-agent) and the dose of the peripherally acting β-blocker (PABRA) are administered for a period of weeks or more.

The methods provided herein may further include subjecting the patient to brain imaging to determine regional metabolic activation and/or cerebral perfusion in cerebro-cortical, forebrain, midbrain and brainstem areas and/or to identify whether said patient is in need of or desiring improvement of cognitive function and/or treatment of a neurodegenerative disease. In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, magnetic resonance imaging-arterial spin labeling (MRI-ASL), or magnetic resonance imaging-blood oxygenation level dependent computerized tomography (MRI-BOLD). In some embodiments the brain imaging may include MRI-ASL used to monitor cerebral blood flow, including, for example, cerebral blood flow to the hippocampus or thalamus. In some embodiments, of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathy burden (for example, based on imaging or CSF sampling) and/or improving regional cerebral metabolic status (reversing hypometabolism) or perfusion in the patient. In certain embodiments of the methods and compositions disclosed herein the β-AR agonist (such as a β-agent) is administered in a dose that is therapeutically effective in improving cognition and/or treating a neurodegenerative disease in a patient. As such, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathy burden (for example, based on imaging or CSF sampling) and/or improvement of regional cerebral metabolic/perfusion status (reversing hypometabolism or hypoperfusion). In another aspect, a method is provided wherein the method includes subjecting a patient to brain imaging to determine regional metabolic activation or perfusion in cerebrocortical, forebrain, midbrain and brainstem areas and/or to identify whether said patient is in need of or desiring improvement of cognitive function and/or treatment of a neurodegenerative disease, and administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a dose of about 15 mg or less. In a similar aspect, a method is provided wherein the method includes subjecting a patient to brain imaging to determine regional metabolic or perfusion activation in cerebrocortical, forebrain, midbrain and brainstem areas and/or to identify whether said patient is in need of or desiring improvement of cognitive function and/or treatment of a neurodegenerative disease, and administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a sub-therapeutic dose.

The method can further include subsequently re-subjecting said patient to brain imaging to determine any improvement in regional metabolic activation in cerebrocortical, forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD.

In yet another aspect, a method is provided wherein the method includes subjecting a patient to brain imaging to determine regional metabolic activation in forebrain, midbrain and brainstem areas, and administering to said patient a β-AR agonist (such as a β-agent) and a peripherally acting β-blocker (PABRA), wherein the peripherally acting β-blocker (PABRA) is administered in a dose of about 15 mg or less. In a related aspect, a method is provided wherein the method includes subjecting a patient to brain imaging to determine regional metabolic activation in forebrain, midbrain and brainstem areas, and administering to said patient a β-AR agonist (such as a β-agent) and a peripherally acting β-blocker (PABRA), wherein the peripherally acting β-blocker (PABRA) is administered in a sub-therapeutic dose. The method can further include subsequently re-subjecting said patient to brain imaging to determine any improvement in regional metabolic or perfusion activation in cerebrocortical, limbic, forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD. In some embodiments the brain imaging may include MRI-ASL used to monitor cerebral blood flow, including, for example, cerebral blood flow to the hippocampus; and an improvement of cerebral blood flow (for example to the hippocampus) in the subsequent MRI-ASL is indicative of effective action of the of 3-AR agonist (such as a β-agent) and/or improved cognition in the patient.

In some embodiments, a detectable label is provided, which can generate a spatial pattern of the brain imaging result. In some embodiments, 2-[$^{18}$F]fluoro-2-deoxy-D-glucose ($^{18}$FDG) can be used for FDG-PET, which can provide characteristic spatial patterns of brain metabolism and can help clinicians to make a reasonably accurate and early diagnosis for appropriate management or prognosis.

In some embodiments a detectable label on blood water molecules is produced by magnetic RF treatment of blood in the neck, which can generate a spatial pattern of the brains perfusion as an imaging result. In some such embodiments, MRI-ASL is used, which can provide characteristic spatial patterns of brain perfusion and can help clinicians to make a reasonably accurate and early diagnosis for appropriate management or prognosis.

In some aspects, a method for improving cognitive function and/or treating a neurodegenerative disease is provided wherein the method includes administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a dose of about 15 mg or less. In some related aspects, a method for improving cognitive function and/or treating a neurodegenerative disease is provided wherein the method includes administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a sub-therapeutic dose.

The method in some embodiments may further include subjecting a patient to brain imaging to determine regional metabolic activation in forebrain, midbrain and brainstem areas and/or to identify whether said patient is in need of or desiring improvement of cognitive function and/or treatment of a neurodegenerative disease. In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism). In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a dose of about 15 mg or less. In a related aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient a β-AR agonist (such as a β-agent) and a peripherally acting β-blocker (PABRA) to improve cognition and/or treat a neurodegenerative disease in said patient, wherein the peripherally acting β-blocker (PABRA) is administered in a sub-therapeutic dose. For some embodiments, the peripherally acting β-blocker (PABRA) is administered to reduce, restrict, or counter any adverse effects of the β-AR agonist (such as a β-agent), e.g., performance-enhancing effects, and reduces the likelihood of abuse. In a similar aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient Compound 03-5, or an optically pure stereoisomer, pharmaceutically acceptable salt, solvate, or prodrug thereof, and a peripherally acting β-blocker (PABRA) to improve cognition and/or treat a neurodegenerative disease in said patient, wherein the peripherally acting β-blocker (PABRA) is administered in a dose of about 15 mg or less. In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient Compound 03-5, or an optically pure stereoisomer, pharmaceutically acceptable salt, solvate, or prodrug thereof, and a peripherally acting β-blocker (PABRA) to improve cognition and/or treat a neurodegenerative disease in said patient, wherein the peripherally acting β-blocker (PABRA) is administered in a sub-therapeutic dose. For some embodiments, the peripherally acting β-blocker (PABRA) is administered to reduce, restrict, or counter any adverse effects of the β-AR agonist (such as a β-agent), e.g., performance-enhancing effects, and reduces the likelihood of abuse.

The method can further include subsequently re-subjecting said patient to brain imaging to determine any improvement in regional metabolic or perfusion activation in cerebrocortical, forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD. In yet another aspect, a method is provided wherein the method includes subjecting a patient to brain imaging determine regional metabolic activation in forebrain, midbrain and brainstem areas; administering to said patient a β-AR agonist (such as a β-agent) and a peripherally acting β-blocker (PABRA); and subsequently re-subjecting said patient to brain imaging to determine any improvement in regional metabolic activation in forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD. In some embodiments, the patient does not have Alzheimer's disease. In some embodiments, the patient does not have Down Syndrome. In some embodiments, the patient does not have Parkinson's disease. In some embodiments, the patient does not have dementia with Lewy bodies.

In some embodiments of any of the aspects and embodiments herein, the β-AR agonist (such as a β-agent) can be administered at a dose of from about 0.01 to 100 mg. In some embodiments, the β-AR agonist (such as a β-agent) can be administered at a dose of from about 30 to 160 μg. In some embodiments, the β-AR agonist (such as a β-agent) can be administered at a dose of from about 50 to 160 μg. For some embodiments, the β-AR agonist (such as a β-agent) can be administered at a dose of from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 μg, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg. In some embodiments, the β-AR agonist (such as a β-agent) can be administered in a dose from 150 μg to 1 mg; or from 200 μg to 500 μg, or about 250 μg, or about 300 μg, or about 400 μg, or about 500 μg. In some embodiments, the β-AR agonist (such as a β-agent) can be administered in a dose from 0.5-50 mg; or 1-25 mg; or 1-10 mg; or 10-20 mg; or 25-50 mg; or mg; or 2-8 mg; or about 0.25 mg; or about 0.5 mg; or about 0.75 mg; or about 1 mg; or about 2 mg; or about 3 mg; or about 4 mg, or about 5 mg;

or about 6 mg; or about 7 mg; or about 8 mg; or about 10 mg; or about 11 mg, or about 12 mg, or about 13 mg, or about 14 mg, or about 15 mg; or about 20 mg; or about 25 mg; or about 30 mg; or about 40 mg; or about 50 mg. In some embodiments of the aspects or embodiments provided herein the β-AR agonist (such as a β-agent) is administered in a dose that is from 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg; or about 11 mg; or about 12 mg; or about 13 mg; or about 15 mg. In some embodiments the aforementioned doses are daily doses, twice daily doses, weekly doses, or twice-weekly doses. For some embodiments, the dose of β-AR agonist (such as a β-agent) and the peripherally acting β-blocker (PABRA) are administered or weekly for a period of weeks or more.

For some embodiments, nadolol is a mixture of four diastereomers. For some embodiments, the nadolol administered is a specific enantiomerically pure isomer.

In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism).

In some embodiments, the brain imaging is fluorodeoxyglucose positron emission tomography (FDG-PET), used alone or in combination with other imaging approaches such as magnetic resonance imaging (MRI) and CT. In some embodiments, the brain imaging is, or can include, MRI-ASL or MRI-BOLD. In some embodiments of the aspects and embodiments disclosed herein, "improving cognition and/or treating a neurodegenerative disease" in a patient may include improving cognitive and executive function, improving inflammatory status in cerebral or cerebrospinal fluid (CSF) samples, attenuating proteinopathies burden (for example, based on imaging or CSF sampling) and/or improving regional cerebral metabolic status (reversing hypometabolism) in the patient. Likewise, in certain embodiments, "identifying a patient in need of or desiring improvement of cognitive function and/or treatment of a neurodegenerative disease" may include identifying a patient in need of or desiring improvement of cognitive and executive function, improvement of inflammatory status in cerebral or CSF samples, attenuation of proteinopathies burden (for example, based on imaging or CSF sampling) and/or improvement of regional cerebral metabolic status (reversing hypometabolism). In another aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol or tulobuterol and nadolol to improve cognition and/or treat a neurodegenerative disease in said patient, wherein nadolol is administered in a dose of about 15 mg or less. In a related aspect, a method is provided wherein the method includes subjecting a patient to brain imaging to determine regional metabolic activation in forebrain, midbrain and brainstem areas and/or to identify whether said patient is in need of or desiring improvement of cognitive function and/or treatment of a neurodegenerative disease, and administering to said patient clenbuterol or tulobuterol and nadolol to improve cognition and/or treat a neurodegenerative disease in said patient, wherein nadolol is administered in a sub-therapeutic dose.

The method can further include subsequently re-subjecting said patient to brain imaging to determine any improvement in regional metabolic activation in forebrain, midbrain and brainstem areas, cognitive function and/or treatment of said neurodegenerative disease. In some embodiments, the brain imaging is FDG-PET, used alone or in combination with other imaging approaches such as MRI and CT. In some embodiments, the brain imaging is, or can include, MRI-ASL or MRI-BOLD. In yet another aspect, a method is provided wherein the method includes subjecting a patient to brain imaging determine regional metabolic activation in forebrain, midbrain and brainstem areas; administering to said patient clenbuterol or tulobuterol and nadolol to improve cognition and/or treat a neurodegenerative disease in said patient, wherein nadolol is administered in a dose of about 15 mg or less; and subsequently re-subjecting said patient to brain imaging to determine any improvement in regional metabolic activation in forebrain, midbrain and brainstem areas, cognitive function. In some embodiments, the brain imaging is FDG-PET, used alone or in combination with other imaging approaches such as MRI and CT. In some embodiments, the brain imaging is, or can include, MRI-ASL or MRI-BOLD.

In some aspects, a method is provided which includes treating a subject identified as having diminished cognitive function and/or being in need of or desiring improvement of cognitive function and/or treatment of a neurodegenerative disease by administering the subject a pharmaceutical composition including a β-agent, $\beta_1$-AR agonist, a $\beta_2$-AR agonist, a peripherally acting β-blocker (PABRA), or any combination thereof. In some embodiments, the method further includes assessing effectiveness of the treatment. In some embodiments, the treatment is assessed by subjecting the subject to a test to assess improved cognitive function or amelioration of the neurodegenerative disease. In some embodiments, the method further includes adjusting administration of the pharmaceutical composition by adjusting dosage of the pharmaceutical composition and/or timing of administration of the pharmaceutical composition.

In some embodiments of any of the aspects or embodiments provided herein, the methods or compositions include a β-agent and a PABRA. In some embodiments of any of the aspects or embodiments provided herein, the methods or compositions include a β-agent and a PABRA.

As used herein, the term "β agonist" or "β-AR agonist" are used interchangeably to mean an agent that acts as an agonist of a β-adrenergic receptor (β-AR). A β agonist may be a $\beta_1$ agonist, a $\beta_1$ agonist, or a non-selective β agonist. In some embodiments a β-AR agonist is a β-agent.

As used herein, the term "$\beta_1$ agonist" is used to mean $\beta_1$-adrenergic receptor agonist or $\beta_1$-AR agonist. In certain embodiments the term $\beta_1$ agonist is understood to include compounds that are primarily $\beta_1$ agonists, but which may also exhibit some peripheral agonism for other adrenergic receptors, such as $\beta_2$-adrenergic receptors. In this application, the terms "$\beta_1$-adrenergic receptor agonist", "$\beta_1$-AR agonist", "$\beta_1$ AR agonist" and "$\beta_1$ agonist" may be used interchangeably. In certain embodiments, the term $\beta_1$-AR agonist expressly includes both selective and partial agonists, as well as biased and non-biased agonists. Examples of $\beta_1$ adrenergic agonists include, for example, xamoterol, noradrenalin, isoprenaline, dopamine and dobutamine and the pharmaceutically-acceptable salts of any of the above. Partial agonists and ligands of the $\beta_1$-AR are known. Further, using the methodology of Kolb et al., but for $\beta_1$-AR instead, one skilled in the art could determine new ligands by structure-based discovery. See *Proc. Natl. Acad. Sci.* USA 2009, 106, 6843-648.

As used herein, the term "$\beta_2$ agonist" is used to mean $\beta_2$-adrenergic receptor agonist or $\beta_2$-AR agonist. In certain embodiments, the term $\beta_2$ agonist is understood to include compounds that are primarily $\beta_2$ agonists, but which may also exhibit some peripheral agonism for other adrenergic receptors, such as $\beta_1$-adrenergic receptors. In this application the terms "$\beta_2$-adrenergic receptor agonist", "$\beta_2$-AR agonist", "$\beta_2$AR agonist" and "$\beta_2$ agonist" may be used interchangeably. In some embodiments the term $\beta_2$-AR agonist expressly includes both selective and partial agonists. $\beta_2$ agonists that may be used in accordance with various aspects and embodiments of the present disclosure may be short-acting, long-acting or ultra long-acting. Examples of short-acting $\beta_2$ agonists that may be used are salbutamol, levosalbutamol, terbutaline, pirbuterol, procaterol, metaproterenol, bitolterol mesylate, oritodrine, isoprenaline, salmefamol, fenoterol, terbutaline, albuterol, and isoetharine. Examples of long-acting $\beta_2$ agonists that may be used are salmeterol, bambuterol, formoterol and clenbuterol. Examples of ultra long-acting $\beta_2$ agonists include indacaterol, vilanterol and olodaterol. Other examples of $\beta_2$ agonists include tulobuterol, mabuterol, and ritodrine.

As used herein, the term "peripherally acting β-blocker (PABRA)" means a β adrenergic receptor antagonist or simply a $\beta_1$-, $\beta_2$- or non-selective β-blocker. Examples of selective peripherally acting β-blockers (PABRA) that may in certain embodiments be used in the methods disclosed herein include nadolol, atenolol, sotalol and labetalol. In certain embodiments a β-blocker that can be used in the methods herein is one or more selected from the group consisting of acebutolol, betaxolol, bisoprolol, celiprolol, esmolol, metaprolol and nevivolol; in other embodiments the methods do not use acebutolol, betaxolol, bisoprolol, celiprolol, esmolol, metaprolol or nevivolol as a β-blocker. Peripherally acting β-blocker (PABRA) can be used to reduce, restrict, or counter any adverse effects of the β-agent, $\beta_1$-AR agonist and/or $\beta_2$-AR agonist, e.g., performance enhancing effects, and therefore reduces any risk of abuse. For example, nadolol can be used to reduce, restrict, or counter any peripheral β agonist effects of a β-agent.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

In certain embodiments a peripherally acting β-blocker (PABRA) is administered to the patient prior to administration of a β-AR agonist (such as a β-agent). In other embodiments, a peripherally acting β-blocker (PABRA) is administered to the patient concurrently with the administration of a β-AR agonist (such as a β-agent). In other embodiments, a peripherally acting β-blocker (PABRA) is co-administered to the patient in a single dosing formulation, in a single tablet and/or in a single capsule.

In certain embodiments of the compositions and methods provided herein, one or more peripherally acting β-blocker (PABRA) are administered prior to or concurrently with a β-AR agonist (such as a β-agent) in order to inhibit or preclude agonism of peripheral $\beta_1$ and/or $\beta_2$ adrenergic receptors by the β-AR agonist (such as a β-agent). In various embodiments it is preferred to block peripheral $\beta_1$ and/or $\beta_2$ adrenergic receptors in accordance with the compositions and methods of the present disclosure in order to preclude, or at least minimize, any adverse effects, e.g., peripheral cardiac effects, on humans being treated.

In certain embodiments, it may be desirable for a PABRA to be administered prior to a β-AR agonist (such as a β-agent) such as to occupy peripheral β-ARs before the β-AR agonist has access to the receptors. Accordingly, in some embodiments, a PABRA and a β-AR agonist (such as a β-agent) are administered once daily (for example once daily in the morning) at a dose specified herein, the PABRA is administered prior to (i.e., 15 mins to 6 hours; or 15 mins to 3 hours; or 1 to 6 hours; or 1 to 5 hours; or 1 to 4 hours; or 1-3 hours; or 1.5 to 2.5 hours; or 2-3 hours; or 2-4 hours; or 2-5 hours; or 1.5 to 3 hours; or 1.5 to 3.5 hours; or 1.5 to 4 hours; or about 30 mins, or about 1 hour; or about 1.5 hours; or about 2 hours; or about 2.5 hours; or about 3 hours; or about 3.5 hours; or about 4 hours; or about 5 hours; 12 hours; one day) the β-AR agonist. In some embodiments a PABRA and a β-AR agonist (such as a β-agent) are administered once daily (for example once daily in the morning) at a dose specified herein, wherein for the first day only the PABRA (without the β-AR agonist) at a dose such as specified herein is administered; and for each day after the first day both the PABRA and the β-AR agonist (such as a β-agent; and at a dose such as specified herein) are administered concurrently (for example, in a single, or joint, formulation such as described herein). In some embodiments a PABRA and a β-AR agonist (such as a β-agent) are administered once daily (for example once daily in the morning) at a dose specified herein, wherein for the first and second day only the PABRA (without the β-AR agonist) at a dose such as specified herein is administered; and for each day after the second day both the PABRA and the β-AR agonist (such as a β-agent; and at a dose such as specified herein) are administered concurrently (for example, in a single, or joint, formulation such as described herein).

In certain embodiments of the methods provided herein, the β-AR agonist (such as a β-agent) is administered orally, intravenously, intramuscularly, transdermally, by inhalation or intranasally. In certain embodiments of the methods provided herein, the β-AR agonist (such as a β-agent) is administered orally.

In certain embodiments of the methods provided herein, the peripherally acting β-blocker (PABRA) is administered orally, intravenously, intramuscularly, by inhalation or intranasally. In certain embodiments of the methods provided herein, the peripherally acting β-blocker (PABRA) is administered orally.

In certain embodiments of the methods provided herein, the β-AR agonist (such as a β-agent) and the peripherally acting β-blocker (PABRA) are administered to the patient in a single formulation. In some embodiments, the single formulation is in the form of a tablet. For some embodiments both agents (β-AR agonist (such as a β-agent) and PABRA) are present in a tablet. For some embodiments, the tablet includes 30 to 160 μg of β-AR agonist (such as a β-agent), and/or 0.1 mg to 10 mg of β-AR agonist (such as a β-agent), and from about 0.1 to 15 mg of the peripherally acting β-blocker (PABRA). In some embodiments, the tablet includes the peripherally acting β-blocker (PABRA) in a sub-therapeutic dose. In some embodiments, the tablet includes the peripherally acting β-blocker (PABRA) in an amount that is 0.01 to 15 mg, 0.1 to 15 mg, 0.1 to 10 mg, 0.1 to 1 mg, 0.1 to 0.5 mg, 0.2 to 0.3 mg, 0.23 to 0.27 mg; 0.1 to 5 mg, 1 to 15 mg, 1 to 10 mg, 1 to 5 mg, 5 to 10 mg, 10 mg or less, 7 mg or less, 5 mg or less, 1 mg or less, about 0.01 mg, about 0.05 mg; about 0.1 mg, about 0.2 mg, about 0.25 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, or about 10 mg. In some embodiments, the tablet includes the peripherally acting β-blocker (PABRA, such as nadolol or atenolol) in an amount that results in a dose of about 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to the 5 mg twice daily (or 10 mg total daily) dose; or in some embodiments a sub-therapeutic dose of a PABRA in the tablet may be about 90%; or about 85%; or about 80%; or about 75%; or about 70%; or 6 about 5%; or about 60%; or about 55%; or about 50%; or about 45%; or about 40%; or about 35%; or about 30%; or 25%; or about 20%; or about 15%; or about 10% or less; about 5%; or about 4%; or about 3%; or about 2.5%; or about 2%; or about 1.5% or less; or about 1%; or about 0.5% as compared to a dose that the agent is effective for, or approved for treating a specific disease indication. For some embodiments the tablet having the aforementioned doses is administered daily. For some embodiments the tablet having the aforementioned doses is administered weekly. In some embodiments, the tablet includes the peripherally acting β-blocker (PABRA) in an amount from about 5 to 10 mg. In some embodiments, the β-AR agonist (such as a β-agent) is present in the tablet from about 0.01 to 100 mg. For some embodiments, the β-AR agonist (such as a β-agent) is present in the tablet from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. For some embodiments, the β-AR agonist (such as a β-agent) is present in the tablet from 0.5-50 mg; or 1-25 mg; or 1-10 mg; or 10-20 mg; or 25-50 mg; or mg; or 2-8 mg; or about 0.25 mg; or about 0.5 mg; or about 0.75 mg; or about 1 mg; or about 2 mg; or about 3 mg; or about 4 mg, or about 5 mg; or about 6 mg; or about 7 mg; or about 8 mg; or about 10 mg; or about 11 mg, or about 12 mg, or about 13 mg, or about 14 mg, or about 15 mg; or about 20 mg; or about 25 mg; or about 30 mg; or about 40 mg; or about 50 mg. For some embodiments, the above-mentioned doses are a total daily dose. For some embodiments, the above-mentioned doses are a weekly dose. For some embodiments, the dose of β-AR agonist (such as a β-agent) and the peripherally acting β-blocker (PABRA) in a tablet are administered for a period of weeks or more.

In certain embodiments of the methods provided herein, the β-AR agonist (such as a 1-agent) and the peripherally acting β-blocker (PABRA) are administered to the patient in a joint formulation. For some embodiments, joint formulation includes from about 30 to 160 μg of the β-AR agonist (such as a β-agent) and 15 mg or less of the peripherally acting β-blocker (PABRA). For some embodiments, joint formulation includes from about 0.5 to 20 mg of the β-AR agonist (such as a β-agent), and 15 mg or less of the peripherally acting β-blocker (PABRA). In some embodiments, the joint formulation includes the peripherally acting β-blocker (PABRA) in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. In some embodiments, the joint formulation includes the peripherally acting β-blocker (PABRA) in an amount from about 5 to 10 mg. In some embodiments, the β-AR agonist (such as a β-agent) is present in the joint formulation from about 0.01 to 100 mg. For some embodiments, the β-AR agonist (such as a β-agent) is present in the joint formulation from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. In some embodiments, the β-AR agonist (such as a β-agent) is present in the joint formulation from about 0.5-50 mg; or 1-25 mg; or 1-10 mg; or 10-20 mg; or 25-50 mg; or mg; or 2-8 mg; or about 1 mg; or about 2 mg; or about 3 mg; or about 4 mg, or about 5 mg; or about 6 mg; or about 7 mg; or about 8 mg; or about 10 mg; or about 0.25 mg; or about 0.5 mg; or about 0.75 mg; or about 15 mg; or about 20 mg; or about 25 mg; or about 30 mg; or about 40 mg; or about 50 mg. For some embodiments, the above-mentioned doses are a total daily dose. For some embodiments the doses of the joint formulations are administered weekly and the dose is total weekly dose. For some embodiments, the dose of β-AR agonist (such as a β-agent) and the peripherally acting β-blocker (PABRA) are administered daily or weekly for a period of weeks or more.

For some embodiments of the methods and compositions provided herein, both Compound 03-5, or an optically pure stereoisomer, pharmaceutically acceptable salt, solvate, or prodrug thereof, and nadolol are administered to the patient orally. For some embodiments, of the methods provided herein, Compound 03-5 and nadolol are administered to the patient orally and both agents are present in a tablet. For some embodiments, the tablet includes from about 0.01 to 100 mg of Compound 03-5 and from about 0.1 to 15 mg of nadolol. In some embodiments, the tablet includes nadolol in an amount from about 5 to 10 mg. In some embodiments, the tablet includes nadolol in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. For some embodiments, nadolol is a mixture of four diastereomers. For some embodiments, the nadolol administered is a specific enantiomerically pure isomer.

For some embodiments, of the methods provided herein, Compound 03-5 and nadolol are administered to the patient orally and both agents are present in a capsule. For some embodiments, the capsule includes from about 0.01 to 100 mg of Compound 03-5 and from about 0.1 to 15 mg of nadolol. In some embodiments, the capsule includes nadolol in an amount from about 5 to 10 mg. In some embodiments, the capsule includes nadolol in an amount from about 0.1 to 15 mg, 0.1 to 10 mg, 0.1 to 1 mg, 0.1 to 5 mg, 1 to 15 mg, 1 to 10 mg, 1 to 5 mg, 10 mg or less, 7 mg or less, 5 mg or less, 1 mg or less, 0.1 mg, 0.5 mg, 1 mg, 2 mg, 3 mg, 4 mg, 5 mg, 6 mg, 7 mg, 8 mg, 9 mg, or 10 mg. For some embodiments, nadolol is a mixture of four diastereomers. For some embodiments, the nadolol administered is a specific enantiomerically pure isomer.

In some embodiments, Compound 03-5, or an optically pure stereoisomer, pharmaceutically acceptable salt, solvate, or prodrug thereof, is present in a tablet from about 0.01 to 100 mg. For some embodiments, Compound 03-5 is present in the tablet from about 30 to 160 μg, 50 to 160 μg, 80 to 160 μg, 100 to 160 μg, 120 to 160 μg, 140 to 160 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, 30 μg, 40 μg, 50 μg, 60 μg, 70 μg, 80 μg, 90 μg, 100 μg, 110 μg, 120 μg, 130 μg, 140 μg, 150 μg, or 160 μg. For some embodiments, Compound 03-5 is present in the tablet from about 0.5-50 mg; or 1-25 mg; or 1-10 mg; or 10-20 mg; or 25-50 mg; or mg; or 2-8 mg; or about 0.25 mg; or about 0.5 mg; or about 0.75 mg; or about 1 mg; or about 2 mg; or about 3 mg; or about 4 mg, or about 5 mg; or about 6 mg; or about 7 mg; or about 8 mg; or about 10 mg; or about 0.25 mg; or about 0.5 mg; or about 0.75 mg; or about 15 mg; or about 20 mg; or about 25 mg; or about 30 mg; or about 40 mg; or about 50 mg. For some embodiments, the tablet would be a total daily dose and is expected to be administered daily for a period of weeks or more. For some embodiments, the tablet would be a total weekly dose and is expected to be administered weekly for a period of weeks or more.

For some embodiments, nadolol can reduce, restrict, or counter any adverse effects of compound 03-5, e.g., potential performance enhancing effects, which reduce the likelihood of abuse.

Clenbuterol, and certain other β-agonists, have hypertrophic and lipolytic properties side effect that have resulted in illicit abuse by athletes and individuals desiring muscle building, athletic performance-enhancing, and/or weight loss. These side effects and propensity for abuse have created hurdles for regulatory approval (such as FDA approval) and create a certain level of a public health risk. However, the hypertrophic and lipolytic actions are caused in large part by activation of peripheral β receptors; accordingly the hypertrophic and lipolytic side effects and propensity for abuse can be reduced, mitigated or eliminated by co-administering a PABRA such as disclosed herein in combination with a β-AR agonist (such as a β-agent). In particular if the β-AR agonist (such as a β-agent) and PABRA are made and sold only in single formulations having both agents such as described herein, then it will be very difficult or impossible for those seeking illicit use or abuse to separate the agents to make a product that would be effective for muscle building, athletic performance-enhancing, or weight loss illicit use. Accordingly, in some aspects and embodiments, provided are compositions and methods that involve a single formulation (such as, for example an oral tablet or a oral capsule) having a β-AR agonist (such as a β-agent) and PABRA, that is effective for improving cognition (a CNS action) but that have a reduced risk of illicit use/abuse as compared to a formulation having only a β-AR agonist (such as a β-agent) without a PABRA. In many embodiments a sub-therapeutic dose of the PABRA is sufficient to counteract the side effects of the β-AR agonist (such as a β-agent), accordingly, a single formulation (such as, for example an oral tablet) as described herein having a β-AR agonist (such as a β-agent) and PABRA may have a therapeutically active dose of the β-AR agonist (such as a β-agent) and a sub-therapeutic dose of the PABRA.

In some embodiments of the aspects and embodiments provided herein, the patient is identified as having a neurodegenerative disease that is one or more selected from the group consisting of MCI (mild cognitive impairment), aMCI (amnestic MCI), Vascular Dementia, mild Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), Parkinson's disease associated with REM sleep behavior disorder (RBD+PD) and/or positive response to RBD Single-Question Screen (RBD1Q) and without hallucinations, MCI or mild dementia due to Parkinson's disease associated with REM sleep behavior disorder (RBD+PD) and/or positive response to RBD Single-Question Screen (RBD1Q) and without hallucinations, ADHD (attention deficit hyperactivity disorder), Alzheimer's disease (AD), early AD, and Down Syndrome (DS). In some embodiments the of the patient is identified as having a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the patient does not have Alzheimer's disease (AD). In some embodiments the patient does not have Down Syndrome. In some embodiments the patient does not have Parkinson's disease. In some embodiments the patient does not have dementia with Lewy bodies. In some embodiments, the patient is diagnosed with MCI. In some embodiments, the patient is diagnosed with mild dementia. In some embodiments, the patient is diagnosed with Parkinson's disease associated with REM sleep behavior disorder (RBD+PD). In some embodiments, the patient is diagnosed with Parkinson's disease associated with REM sleep behavior disorder (RBD+PD) and/or positive response to RBD Single-Question Screen (RBD1Q). In some embodiments, the patient is diagnosed with Parkinson's disease associated with REM sleep behavior disorder (RBD+PD) and/or positive response to RBD Single-Question Screen (RBD1Q) and without hallucinations. In some embodiments, the patient is diagnosed with MCI or mild dementia due to Parkinson's disease associated with REM sleep behavior disorder (RBD+PD) and/or positive response to RBD Single-Question Screen (RBD1Q). In some embodiments, the patient is diagnosed with MCI or mild dementia due to Parkinson's disease associated with REM sleep behavior disorder (RBD+PD) and/or positive response to RBD Single-Question Screen (RBD1Q) and without hallucinations.

In some embodiments, the patient is subjected to a cognition test or model after said administration. In some embodiments, the patient is subjected to a cognition test or model after said administration wherein the cognition test or model is a memory test; a diagnostic indicator of mental status, brain function, mental condition; a contextual learning test and/or brain imaging. In some embodiments, the patient is subjected to a cognition test or model before said administration. In some embodiments, the patient is subjected to a cognition test or model before said administration wherein the cognition test or model is a memory test; a diagnostic indicator of mental status, brain function, mental condition; a contextual learning test and/or brain imaging. In some embodiments the patient is subjected to a cognition test or model such as a memory test; a diagnostic indicator of mental status, brain function, mental condition; a contextual learning test and/or brain imaging before said administration and the cognition test or model is used to identify a patient in need of or desiring improvement of cognitive function and/or treatment of a neurodegenerative disease in accordance with the methods and compositions provided herein. In some embodiments, the patient is subjected to a cognition test or model before and after said administration. In some embodiments, the patient is subjected to a cognition test or model before and after said administration wherein the cognition test or model is a memory test; a diagnostic indicator of mental status, brain function, mental condition; a contextual learning test and/or brain imaging. In some embodiments, the cognition test determines a change from baseline in QTc interval using the Fredericia (QTcF) and Bazett (QTcB) corrections. In some embodiments the cognition test includes a CANTAB assessment. In some embodiments the cognition test includes assessing a Change from Baseline in Negative Emotional Bias in the Facial Expression Recognition Task (FERT) test.

In certain embodiments, the patient demonstrates improved cognition following said administration. In some embodiments, the patient demonstrates improved cognition as demonstrated by an improvement in a cognition test or model; a memory test; a diagnostic indicator of mental status, brain function, mental condition; a contextual learning test; brain imaging or the like in the patient.

"Improving cognition," "improved cognition" or "improvement in cognition" means an improvement in an individual's cognitive capacity, or memory, or the like. In certain embodiments, the methods described herein result in an improvement cognition, for example as demonstrated by an improvement in a cognition test, a memory test, brain imaging and/or a contextual learning test in the patient. In some embodiments, the methods described herein result in an improvement in a contextual learning test in the patient wherein said contextual learning test is a spatial contextual learning test or Arizona Cognitive Test Battery (ACTB).

In some embodiments, the patient is a mammal. In some embodiments the patient is a human. In some embodiments, the patient is a child human. In some embodiments the patient is an adult human. Child, as used herein, means a human from about 5 to 20 years of age. Adult, as used herein, means a human from about 21 years of age and older.

BRIEF DESCRIPTION OF THE DRAWINGS

The accompanying drawings, which are incorporated in and constitute a part of this specification, exemplify various embodiments of the present invention and, together with the description, serve to explain and illustrate principles of the present disclosure. The drawings are intended only to illustrate major features of the exemplary embodiments in a diagrammatic manner.

DETAILED DESCRIPTION OF THE INVENTION

Figure 1:
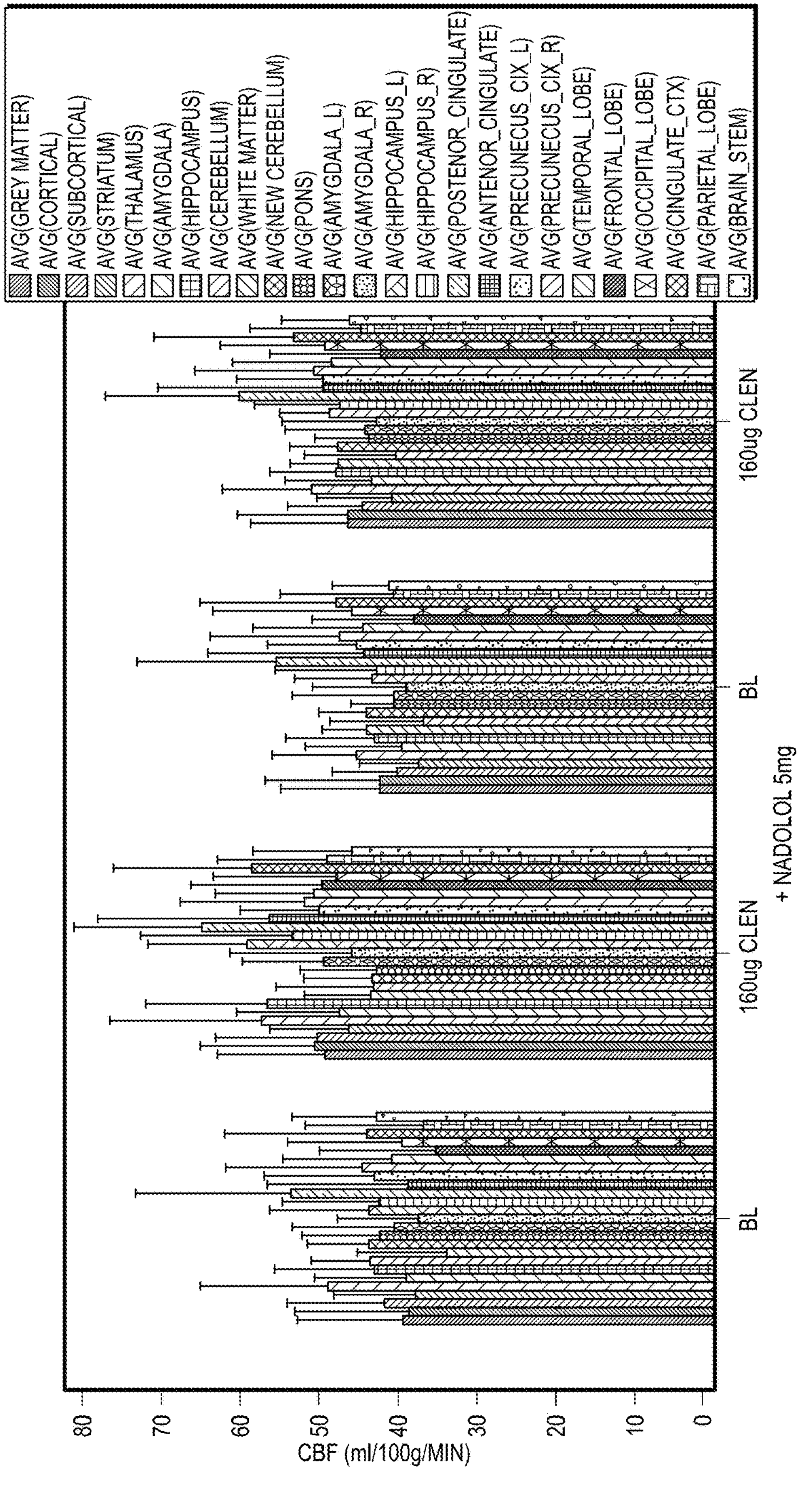
FIG. 1 shows a graph of cerebral blood flow in patients after being administered a single dose of clenbuterol and/or nadolol relative to their baseline.
Figure 2:
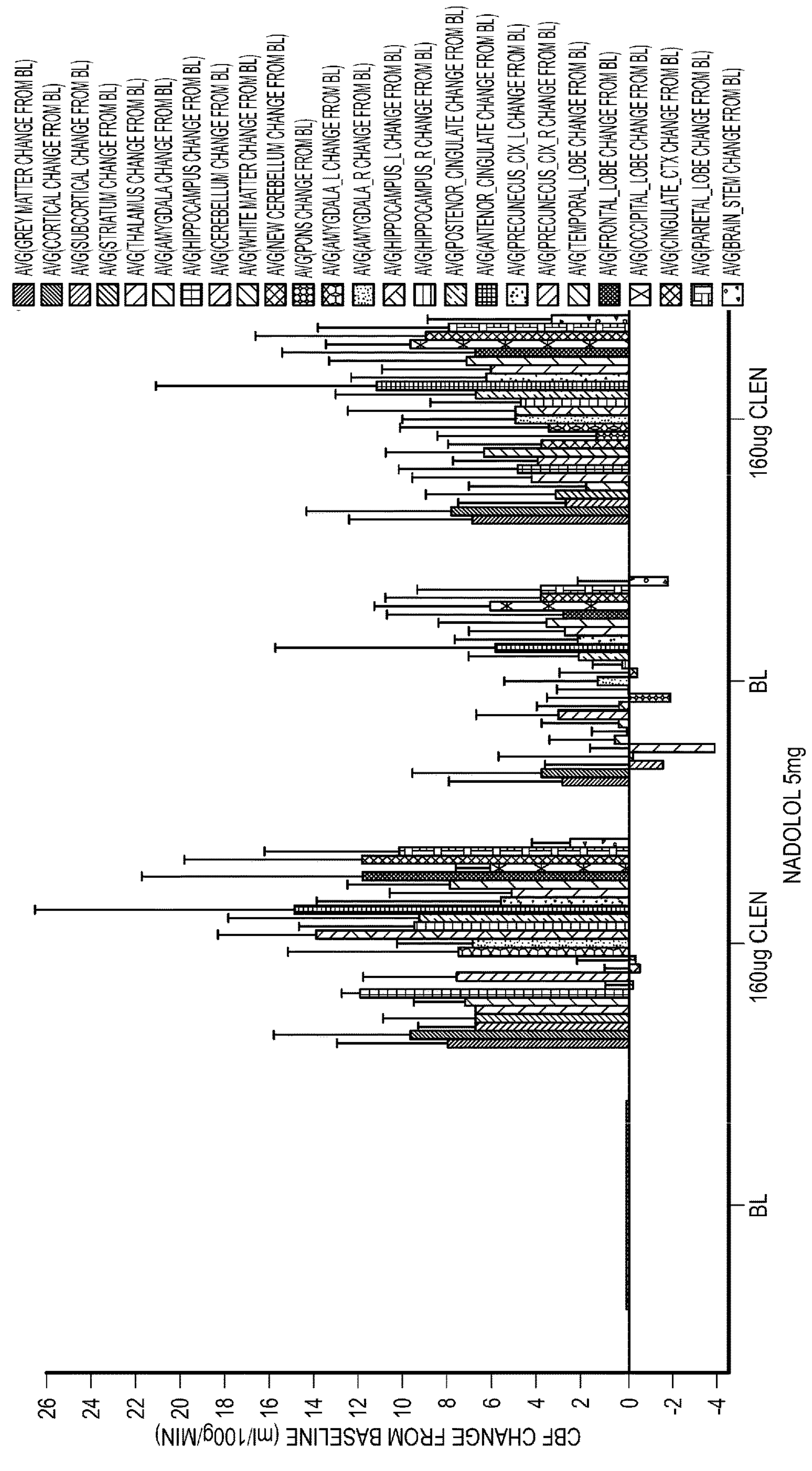
FIG. 2 shows a graph of cerebral blood flow in patients after being administered a single dose of clenbuterol and/or nadolol relative to their baseline.

In certain aspects and embodiments of the present disclosure, compositions and methods result in an improved cognition, raised cerebral metabolic activity and/or improved inflammatory control in a patient. In some embodiments, the methods described herein result in an improvement cognition, for example as demonstrated by an improvement in a cognition test or model; a memory test; a diagnostic indicator of mental status, brain function, mental condition; a contextual learning test; or the like in the patient. Such cognitive tests, diagnostics and models are well known in the art. In various aspects and embodiments, any of many accepted contextual learning tests for animals or humans can be used to assess baseline cognitive function and/or to measure or quantify improved cognitive function. In some embodiments, the compositions and methods described herein may result in an improvement one or more tests, diagnostics and models as follows. Likewise for the raised cerebral metabolic activity and improved inflammatory control—these in certain embodiments may be imaged via FDG-PET and via sampling of cerebrospinal fluid (CSF) allowing measures of inflammatory cytokines and markers of glial cell activation. In some embodiments, magnetic resonance imaging-arterial spin labeling (MRI-ASL) can be used for neuroimaging. In some embodiments, magnetic resonance imaging-blood oxygenation level dependent computerized tomography (MRI-BOLD) can be used for neuroimaging. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

β-Agents

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multi-cyclic ring systems include, but are not limited to, bicycle [4.4.0]decane, bicycle[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(O)-cycloalkyl, or —$S(O)_2$-cycloalkyl.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, $-CH{=}CH(CH_3)$, $-CH{=}C(CH_3)_2$, $-C(CH_3){=}CH_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and $-C{\equiv}C(CH_3)$, among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(O)-aryl, or —$S(O)_2$-aryl. Heteroaryloxy refers to —O-heteroaryl. Heteroarylthio refers to —S— heteroaryl. This term also encompasses oxidized forms of sulfur, such as —S(O)-heteroaryl, or —$S(O)_2$-heteoaryl.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O— heterocycyl. Heterocyclylthio refers to —S-heterocycyl. This term also encompasses oxidized forms of sulfur, such as —S(O)-heterocyclyl, or —$S(O)_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —$NO_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

As described herein, β-agent compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR^{\circ}$; $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$; —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$S(O)(NR^{\circ})R^{\circ}$; —$S(O)_2N{=}C(NR^{\circ}_2)_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; —$SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$; -(halo$R^{\bullet}$); —$(CH_2)_{0-2}OH$; —$(CH_2)_{0-2}OR^{\bullet}$; —$(CH_2)_{0-2}CH(OR^{\bullet})_2$; —O(halo$R^{\bullet}$); —CN; —$N_3$; —$(CH_2)_{0-2}C(O)R^{\bullet}$; —$(CH_2)_{0-2}C(O)OH$; —$(CH_2)_{0-2}C(O)OR^{\bullet}$; —$(CH_2)_{0-2}SR'$; —$(CH_2)_{0-2}SH$; —$(CH_2)_{0-2}NH_2$; —$(CH_2)_{0-2}NHR^{\bullet}$; —$(CH_2)_{0-2}NR^{\bullet}_2$; —$NO_2$, —$SiR^{\bullet}_3$; —$OSiR^{\bullet}_3$; —$C(O)SR^{\bullet}$; —($C_{1-4}$ straight or branched alkylene)$C(O)OR^{\bullet}$; or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O; =S; =NNR*$_2$; =NNHC(O)R*; =NNHC(O)OR*; =NNHS(O)$_2$R*; =NR*; =NOR*; —O(C(R*$_2$))$_{2-3}$O—; or —S(C(R*$_2$))$_{2-3}$S—; wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$; -(haloR$^●$); —OH, —OR$^●$; —O(haloR$^●$); —CN; —C(O)OH; —C(O)OR$^●$; —NH$_2$; —NHR$^●$; —NR$^●_2$; or —NO$_2$; wherein each R$^●$ is unsubstituted or where preceded by "halo" is substituted only with one or more halogens, and is independently $C_{1-4}$ aliphatic, —CH$_2$Ph; —O(CH$_2$)$_{0-1}$Ph; or a 5-6-membered saturated; partially unsaturated; or aryl ring having 0-4 heteroatoms independently selected from nitrogen, oxygen, or sulfur.

Suitable substituents on a substitutable nitrogen of an "optionally substituted" group include —R$^†$; —NR$^†_2$; —C(O)R$^†$; —C(O)OR$^†$; —C(O)C(O)R$^†$; —C(O)CH$_2$C(O)R$^†$; —S(O)$_2$R$^†$; —S(O)$_2$NR$^†_2$; —C(S)NR$^†_2$; —C(NH)NR$^†_2$; or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^†$; -(haloR$^†$); —OH; —OR$^†$; —O(haloR$^†$); —CN; —C(O)OH; —C(O)OR$^†$; —NH$_2$; —NHR$^†$; —NR$^†_2$; or —NO$_2$; wherein each R$^†$ is unsubstituted or where preceded by "halo" is substituted only with one or more halogens, and is independently $C_{1-4}$ aliphatic, —CH$_2$Ph; —O(CH$_2$)$_{0-1}$Ph; or a 5-6-membered saturated; partially unsaturated; or aryl ring having 0-4 heteroatoms independently selected from nitrogen, oxygen, or sulfur.

Thiol refers to —SH. Thiocarbonyl refers to (=S). Sulfonyl refers to —SO$_2$-alkyl, —SO$_2$-substituted alkyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclyl, and —SO$_2$-substituted heterocyclyl. Sulfonylamino refers to —NR$^a$SO$_2$alkyl, —NR$^a$SO$_2$-substituted alkyl, —NR$^a$SO$_2$cycloalkyl, —NR$^a$SO$_2$ substituted cycloalkyl, —NR$^a$SO$_2$aryl, —NR$^a$SO$_2$ substituted aryl, —NR$^a$SO$_2$heteroaryl, —NR$^a$SO$_2$ substituted heteroaryl, —NR$^a$SO$_2$heterocyclyl, —NR$^a$SO$_2$ substituted heterocyclyl, wherein each R$^a$ independently is as defined herein.

Carboxyl refers to —COOH or salts thereof. Carboxyester refers to —C(O)O-alkyl, —C(O)O— substituted alkyl, —C(O)O-aryl, —C(O)O-substituted aryl, —C(O)β-cycloalkyl, —C(O)O— substituted cycloalkyl, —C(O)O-heteroaryl, —C(O)O-substituted heteroaryl, —C(O)O-heterocyclyl, and —C(O)O-substituted heterocyclyl. (Carboxyester)amino refers to —NR$^a$—C(O)O-alkyl, —NR$^a$—C(O)O-substituted alkyl, —NR$^a$—C(O)O-aryl, —NR$^a$—C(O)O-substituted aryl, —NR$^a$—C(O)O—cycloalkyl, —NR$^a$—C(O)O-substituted cycloalkyl, —NR$^a$—C(O)O-heteroaryl, —NR$^a$—C(O)O— substituted heteroaryl, —NR$^a$—C(O)O-heterocyclyl, and —NR$^a$—C(O)O-substituted heterocyclyl, wherein R$^a$ is as recited herein. (Carboxyester)oxy refers to —O—C(O)O-alkyl, —O—C(O)O— substituted alkyl, —O—C(O)O-aryl, —O—C(O)O-substituted aryl, —O—C(O)β-cycloalkyl, —O—C(O)O— substituted cycloalkyl, —O—C(O)O-heteroaryl, —O—C(O)O-substituted heteroaryl, —O—C(O)O— heterocyclyl, and —O—C(O)O-substituted heterocyclyl. Oxo refers to (=O).

The terms "amine" and "amino" refer to derivatives of ammonia, wherein one of more hydrogen atoms have been replaced by a substituent which include, but are not limited to alkyl, alkenyl, aryl, and heterocyclyl groups. In some embodiments, substituted amino can include —NH—CO—R. Carbamate groups refers to —O(C=O)NR$_1$R$_2$, where R$_1$ and R$_2$ are independently hydrogen, aliphatic groups, aryl groups, or heterocyclyl groups.

Aminocarbonyl refers to —C(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylalkyl refers to -alkylC(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylamino refers to —NR$^a$C(O)N(R$^b$)$_2$, wherein R$^a$ and each R$^b$ are as defined herein. Aminodicarbonylamino refers to —NR$^a$C(O)C(O)N(R$^b$)$_2$, wherein R$^a$ and each R$^b$ are as defined herein. Aminocarbonyloxy refers to —O—C(O)N(R$^b$)$_2$, wherein each R$^b$ independently is as defined herein. Aminosulfonyl refers to —SO$_2$N(R$^b$)$_2$, wherein each R$^b$ independently is as defined herein.

Imino refers to —N=R$^c$ wherein R$^c$ may be selected from hydrogen, aminocarbonylalkyloxy, substituted aminocarbonylalkyloxy, aminocarbonylalkylamino, and substituted aminocarbonylalkylamino.

Additionally, unless otherwise stated, structures depicted herein are also meant to include compounds that differ only in the presence of one or more isotopically enriched atoms. For example, compounds having the present structures including the replacement of hydrogen by deuterium (e.g., D or $H^2$) or tritium (e.g., T or $H^3$), or the replacement of a carbon by a $^{13}$C- or $^{14}$C-enriched carbon are included and are within the scope of this invention. Such compounds are useful, for example, as analytical tools, as probes in biological assays, or as therapeutic agents in accordance with the present invention.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

Disclosed herein is a β-agent compound according to Formula (I) or an optically pure stereoisomer, pharmaceutically acceptable salt, solvate, or prodrug thereof Formula (I)

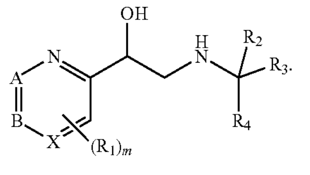

Each A, B, and X can be independently a nitrogen or carbon. Each $R_1$ can be independently hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

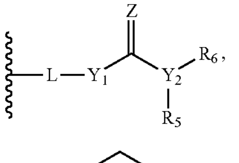,
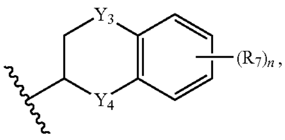,
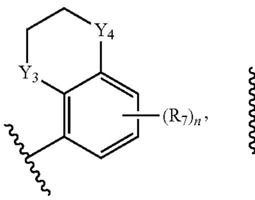,
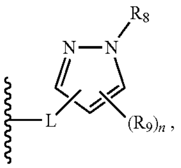,
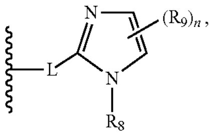,
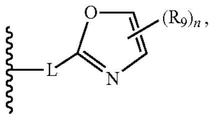,
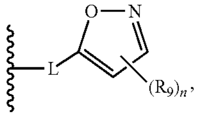,
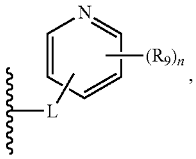,
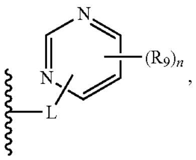,
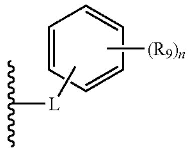, or
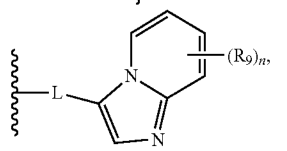, or $R_2$ and $R_3$ together with the carbon can form an unsubstituted or substituted 3-7 membered cycloalkyl or heterocycle ring.

L can be a C1-C5 alkyl linker optionally substituted, each $Y_1$, $Y_2$, $Y_3$, and $Y_4$ can be independently a covalent bond, a carbon, an oxygen, or a nitrogen, optionally substituted with hydrogen, unsubstituted or substituted alkyl, or unsubstituted or substituted cycloalkyl, and Z can be O or S.

$R_5$ and $R_6$ can be independently hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Also disclosed herein is a β-agent compound according to Formula (II) or an optically pure stereoisomer, pharmaceutically acceptable salt, solvate, or prodrug thereof Formula (II)

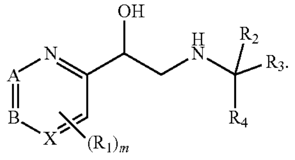

Each A, B, and X can be independently a nitrogen or carbon. Each $R_1$ can be hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

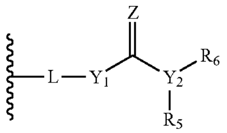
,
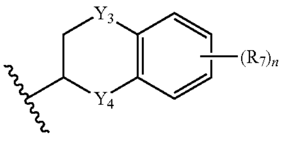
,
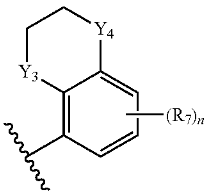
,
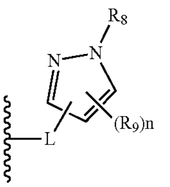
,
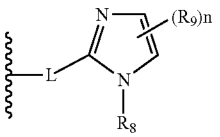
,
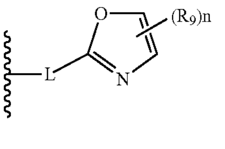
,
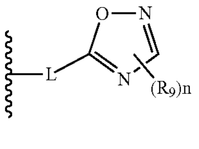
, -continued

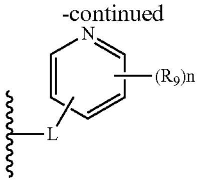
,
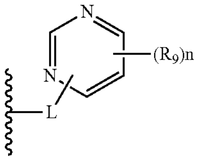
,
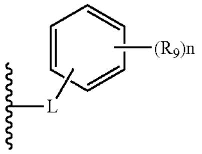
, or
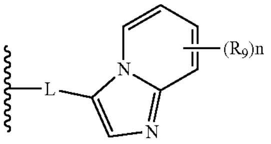
, or $R_2$ and $R_3$ together with the carbon can form an unsubstituted or substituted 3-7 membered cycloalkyl or heterocycle ring.

L can be a C1-C5 alkyl linker optionally substituted, each $Y_1$, $Y_2$, $Y_3$, and $Y_4$ can be independently a covalent bond, a carbon, an oxygen, or a nitrogen, optionally substituted with hydrogen, unsubstituted or substituted alkyl, or unsubstituted or substituted cycloalkyl, and Z can be O or S.

$R_5$ and $R_6$ can be independently hydrogen, unsubstituted or substituted alkyl, or $R_5$ and $R_6$ can be cyclically linked and together with $Y_2$ to form an optionally substituted cycloalkyl or heterocycle, each $R_7$ can be hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Further disclosed herein is a compound according to Formula (III) or an optically pure stereoisomer, pharmaceutically acceptable salt, solvate, or prodrug thereof Formula (III)

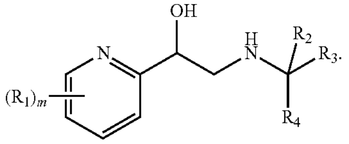

Each $R_1$ can be independently hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

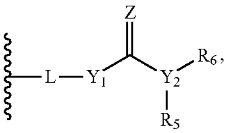
,
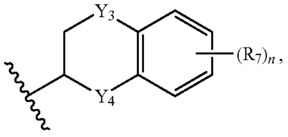
,
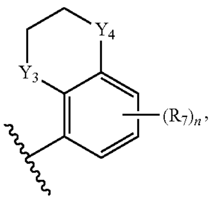
,
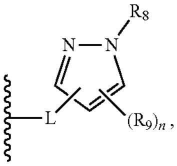
,
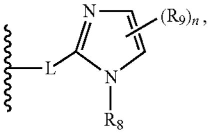
,
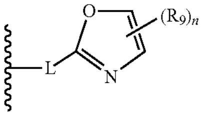
,
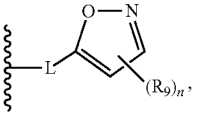
,
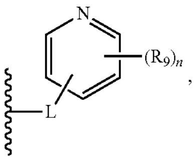
,
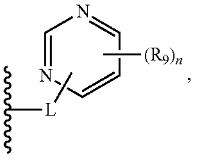
,
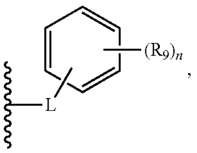
, or
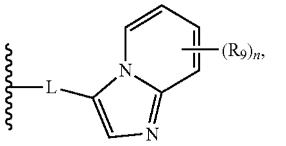
, or $R_2$ and $R_3$ together with the carbon can form an unsubstituted or substituted 3-7 membered cycloalkyl or heterocycle ring.

L can be a C1-C5 alkyl linker optionally substituted, each $X_1$, $X_2$, $X_3$, and $X_4$ can be independently a covalent bond, a carbon, an oxygen, or a nitrogen, optionally substituted with hydrogen, unsubstituted or substituted alkyl, or unsubstituted or substituted cycloalkyl, and Y can be O or S.

$R_5$ and $R_6$ can be independently hydrogen, unsubstituted or substituted alkyl, or $R_5$ and $R_6$ can be cyclically linked and together with $Y_2$ to form an optionally substituted cycloalkyl or heterocycle, each $R_7$ can be independently hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Further disclosed herein is a β-agent compound according to Formula (I'):

Formula (I')

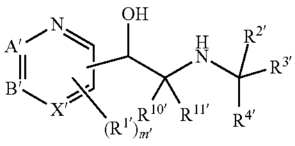

or a pharmaceutically acceptable salt thereof, wherein:

A', B', and X' are each independently nitrogen or carbon;

each $R^{1'}$ is independently halogen, —R', —CN, —$NO_2$, —$SF_5$, —$OR^x$, —$NR^x_2$, —$NHR^x$, —$SO_2R'$, —C(O)R', —C(O)$NR'_2$;

each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each $R^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

$R^{2'}$, $R^{3'}$, and $R^{4'}$ are each independently halogen, —R', —CN, —$NO_2$, —OR', —$NR'_2$,

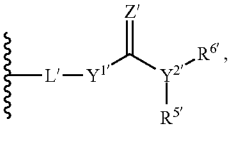
,
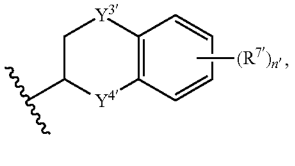
,

-continued

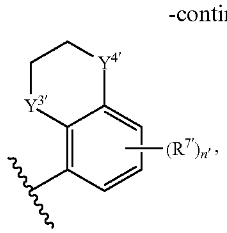,
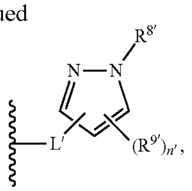,
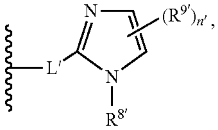,
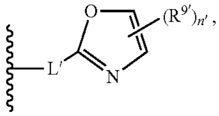,
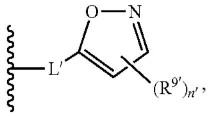,
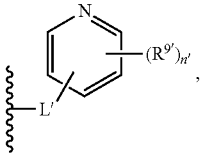,
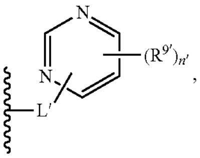,
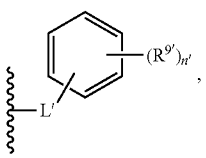, or
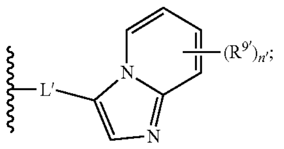;

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted $C_{1-5}$ alkylene;

$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

$R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, $—NO_2$, $—NR'_2$, or —OR';

n' is an integer selected from 0 to 4;

$R^{8'}$ is hydrogen, —CN, optionally substituted alkyl, or an optionally substituted aryl ring;

each $R^{9'}$ is independently hydrogen, halogen, —CN, $—OR^x$, $—NR^x_2$, or optionally substituted alkyl; and $R^{10'}$ and $R^{11'}$ are each independently hydrogen or optionally substituted $C_{1-2}$ aliphatic.

Further disclosed herein is a β-agent compound according to Formula (I"):

Formula (I'')

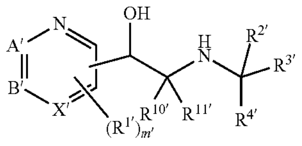

or a pharmaceutically acceptable salt thereof, wherein:

A', B', and X' are each independently nitrogen or carbon;

each $R^{1'}$ is independently halogen, —R', —CN, $—NO_2$, $—SF_5$, $—OR^x$, $—NR^x_2$, $—NHR^x$, $—SO_2R'$, —C(O)R', $—C(O)NR'_2$, —NR'C(O)R', $—NR'CO_2R'$, or $—CO_2R'$;

each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each $R^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

$R^{2'}$, $R^{3'}$, and $R^{4'}$ are each independently halogen, —R', —CN, $—NO_2$, —OR', $—NR'_2$,

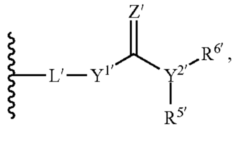,
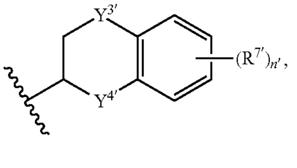,

-continued

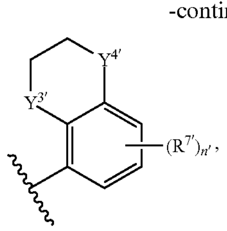

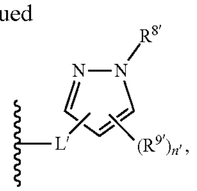

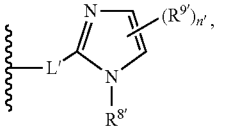

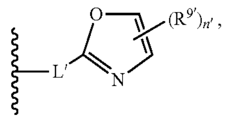

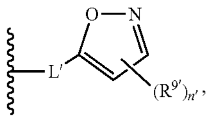

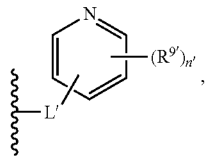

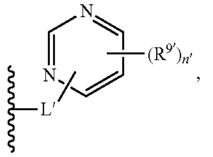

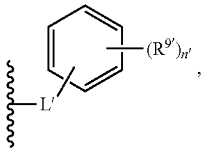

or

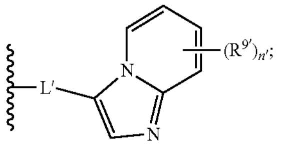

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted $C_{1-5}$ alkylene;

$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

$R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, —$NO_2$, —$NR'_2$, or —OR';

n' is an integer selected from 0 to 4;

$R^{8'}$ is hydrogen, —CN, optionally substituted alkyl, or an optionally substituted aryl ring;

each $R^{9'}$ is independently hydrogen, halogen, —CN, —$OR^x$, —$NR^x_2$, or optionally substituted alkyl; and $R^{10'}$ and $R^{11'}$ are each independently hydrogen or optionally substituted $C_{1-2}$ aliphatic.

As defined above and described herein, A' is nitrogen or carbon. In some embodiments A' is nitrogen. In some embodiments A' is carbon.

In some embodiments A' is selected from those depicted in Table 1, below.

As defined above and described herein, B' is nitrogen or carbon. In some embodiments B' is nitrogen. In some embodiments B' is carbon.

In some embodiments B' is selected from those depicted in Table 1, below.

As defined above and described herein, X' is nitrogen or carbon. In some embodiments X' is nitrogen. In some embodiments X' is carbon.

In some embodiments X' is selected from those depicted in Table 1, below.

As defined above, each $R^{1'}$ is independently halogen, —R', —CN, —$NO_2$, —$SF_5$, —$OR^x$, —$NR^x_2$, —$NHR^x$, —$SO_2R'$, —C(O)R', —C(O)$NR'_2$, —NR'C(O)R', —NR'$CO_2$R', or —$CO_2$R'.

In some embodiments, $R^{1'}$ is hydrogen. In some embodiments, $R^{1'}$ is halogen. In some embodiments, $R^{1'}$ is —R'. In some embodiments, $R^{1'}$ is cyano. In some embodiments, $R^{1'}$ is —$NO_2$. In some embodiments, $R^{1'}$ is —$SF_5$. In some embodiments, $R^{1'}$ is —$OR^x$. In some embodiments, $R^{1'}$ is —$NR^x_2$. In some embodiments, $R^{1'}$ is —$NHR^x$. In some embodiments, $R^{1'}$ is —$SO_2$R'. In some embodiments, $R^{1'}$ is —C(O)R'. In some embodiments, $R^{1'}$ is —C(O)$NR'_2$. In some embodiments, $R^{1'}$ is —NR'C(O)R'. In some embodiments, $R^{1'}$ is —NR'$CO_2$R'. In some embodiments, $R^{1'}$ is —$CO_2$R'.

In some embodiments, $R^{1'}$ is —Br. In some embodiments, $R^{1'}$ is —Cl. In some embodiments, $R^{1'}$ is —F.

In some embodiments, $R^{1'}$ is —$CH_3$. In some embodiments, $R^{1'}$ is —$CH_2CH_3$. In some embodiments, $R^{1'}$ is —$CH(CH_3)_2$.

In some embodiments, $R^{1'}$ is —$CF_3$. In some embodiments, $R^{1'}$ is —$CF_2H$. In some embodiments, $R^{1'}$ is —$CFH_2$. In some embodiments, $R^{1'}$ is —$CF_2CH_3$. In some embodiments, $R^{1'}$ is —$CH_2CF_3$. In some embodiments, $R^{1'}$ is —C≡CCH. In some embodiments, $R^{1'}$ is vinyl. In some embodiments, $R^{1'}$ is —C≡$CCF_3$. In some embodiments, $R^{1'}$ is —$CO_2$H.

In some embodiments, $R^{1'}$ is —CN.

In some embodiments, $R^{1'}$ is —$OCH_3$. In some embodiments, $R^{1'}$ is —$OCH_2CH_3$. In some embodiments, $R^{1'}$ is —$OCH(CH_3)_2$. In some embodiments, $R^{1'}$ is —$OCF_3$. In some embodiments, $R^{1'}$ is —$NHCH_3$. In some embodiments, $R^{1'}$ is —$NHCD_3$. In some embodiments, $R^{1'}$ is —$N(CD_3)CO_2$tBu. In some embodiments, $R^{1'}$ is —$NHCH_2CH_3$. In some embodiments, $R^{1'}$ is —$NHCH_2(CH_3)_2$. In some embodiments, $R^{1'}$ is —$NHCH_2CF_3$. In some embodiments, $R^{1'}$ is —NHPh. In some embodiments, $R^{1'}$ is —NHAc. In some embodiments, $R^{1'}$ is —$N(CH_3)_2$. In some embodiments, $R^{1'}$ is

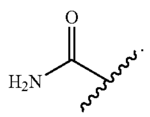

In some embodiments, $R^{1'}$ is

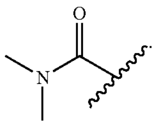 [SMILES: *C(=O)N(C)C]

In some embodiments, $R^{1'}$ is

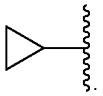

In some embodiments, $R^{1'}$ is

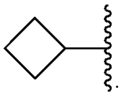 [SMILES: *C1CCC1]

In some embodiments, $R^{1'}$ is

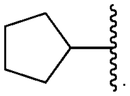

In some embodiments, $R^{1'}$ is

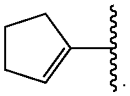

In some embodiments, $R^{1'}$ is

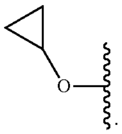

In some embodiments, $R^{1'}$ is

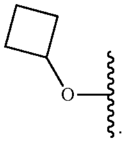 [SMILES: *OC1CCC1]

In some embodiments, $R^{1'}$ is

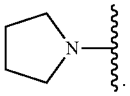 [SMILES: *N1CCCC1]

In some embodiments, $R^{1'}$ is

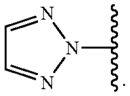

In some embodiments, $R^{1'}$ is

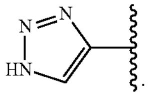

In some embodiments, $R^{1'}$ is

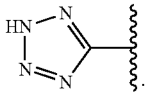

In some embodiments, $R^{1'}$ is

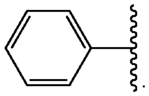

In some embodiments, $R^{1'}$ is

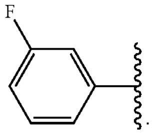

In some embodiments, $R^{1'}$ is

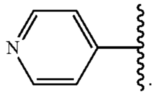

In some embodiments $R^{1'}$ is

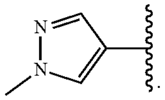

In some embodiments, $R^{1'}$ is

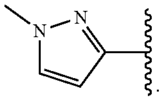 [SMILES: *c1ccn(C)n1]

In some embodiments, $R^{1'}$ is

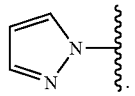

In some embodiments, $R^{1'}$ is

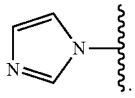 [SMILES: *n1ccnc1]

In some embodiments, $R^{1'}$ is

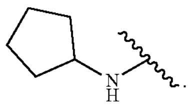 [SMILES: *NC1CCCC1]

In some embodiments, $R^{1'}$ is

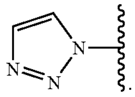 [SMILES: *n1ccnn1]

In some embodiments, $R^{1'}$ is

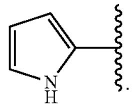

In some embodiments, $R^{1'}$ is

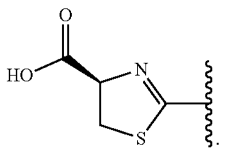 [SMILES: *C1=N[C@H](C(=O)O)CS1]

In some embodiments, $R^{1'}$ is

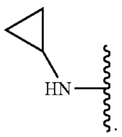 [SMILES: *NC1CC1]

In some embodiments, $R^{1'}$ is

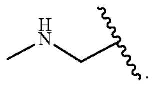

In some embodiments, $R^{1'}$ is

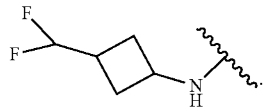 [SMILES: *NC1CC(C(F)F)C1]

In some embodiments, $R^{1'}$ is

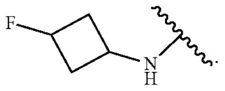

In some embodiments, $R^{1'}$ is

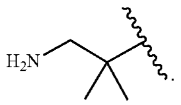 [SMILES: *C(C)(C)CN]

In some embodiments, $R^{1'}$ is selected from those depicted in Table 1, below.

As defined above, each R' is independently hydrogen or an optionally substituted group selected from $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur.

In some embodiments, R' is hydrogen.

In some embodiments, R' is an optionally substituted $C_{1-6}$ aliphatic. For instance, in some embodiments, R' is $—CF_3$, $—CF_2H$, or $—CFH_2$.

In some embodiments, R' is an optionally substituted 3-8 membered saturated monocyclic carbocyclic ring.

In some embodiments, R' is an optionally substituted 3-8 membered partially unsaturated monocyclic carbocyclic ring.

In some embodiments, R' is an optionally substituted phenyl.

In some embodiments, R' is an optionally substituted 8-10 membered bicyclic partially unsaturated carbocyclic ring.

In some embodiments, R' is an optionally substituted 8-10 membered bicyclic aromatic carbocyclic ring.

In some embodiments, R' is an optionally substituted 4-8 membered saturated monocyclic heterocyclic ring having 1-2 heteroatoms independently selected from nitrogen, oxygen, or sulfur.

In some embodiments, R' is an optionally substituted 4-8 membered partially unsaturated monocyclic heterocyclic ring having 1-2 heteroatoms independently selected from nitrogen, oxygen, or sulfur.

In some embodiments, R' is an optionally substituted 5-6 membered monocyclic heteroaromatic ring having 1-4 heteroatoms independently selected from nitrogen, oxygen, or sulfur.

In some embodiments, R' is an optionally substituted 8-10 membered bicyclic partially unsaturated ring having 1-5 heteroatoms independently selected from nitrogen, oxygen, or sulfur.

In some embodiments, R' is an optionally substituted 8-10 membered bicyclic heteroaromatic ring having 1-5 heteroatoms independently selected from nitrogen, oxygen, or sulfur.

In some embodiments, R' is selected from those depicted in Table 1, below.

As defined above, each $R^x$ is independently an optionally substituted group selected from $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur.

In some embodiments, $R^x$ is an optionally substituted $C_{1-6}$ aliphatic. For instance, in some embodiments, $R^x$ is —$CF_3$, —$CF_2H$, or —$CFH_2$. In some embodiments, $R^x$ is $C_{1-6}$ alkyl.

As defined above, m' is an integer selected from 0 to 4.

In some embodiments, m' is 0. In some embodiments, m' is 1. In some embodiments, m' is 2. In some embodiments, m' is 3. In some embodiments, m' is 4.

As defined above, $R^{2'}$, $R^{3'}$, and $R^{4'}$ are each independently halogen, —R', —CN, —OH, —OR', —NR'$_2$, —NHR', —$NH_2$,

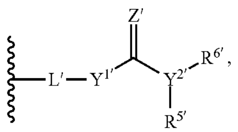

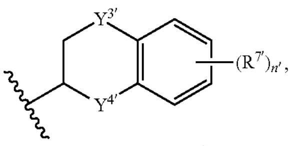

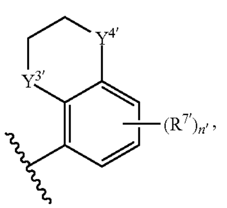

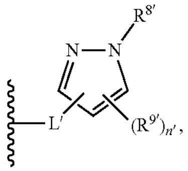

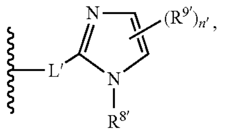

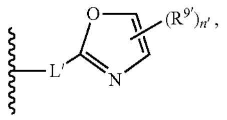

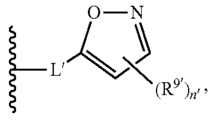

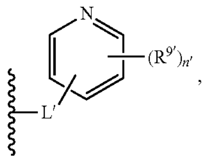

-continued

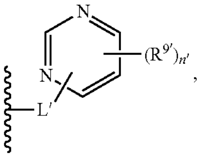

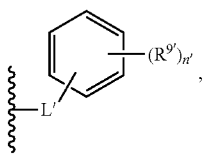

or

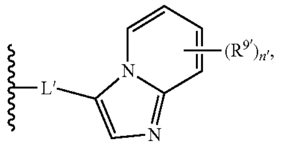

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

In some embodiments, $R^{2'}$ is hydrogen. In some embodiments, $R^{2'}$ is halogen. In some embodiments, $R^{2'}$ is —R'. In some embodiments, $R^{2'}$ is —CN. In some embodiments, $R^{2'}$ is —$NO_2$. In some embodiments, $R^{2'}$ is —OH. In some embodiments, $R^{2'}$ is —OR'. In some embodiments, $R^{2'}$ is —NR'$_2$. In some embodiments, $R^{2'}$ is —NHR'. In some embodiments, $R^{2'}$ is —$NH_2$.

In some embodiments, $R^{2'}$ is

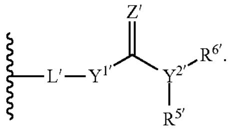

In some embodiments, $R^{2'}$ is

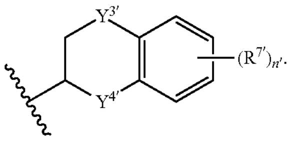

In some embodiments, $R^{2'}$ is

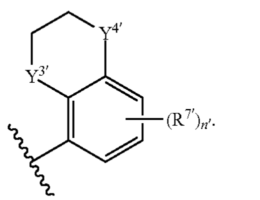

In some embodiments, $R^{2'}$

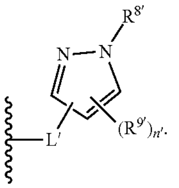

In some embodiments, $R^{2'}$ is

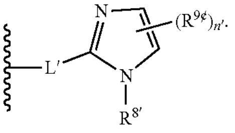

In some embodiments, $R^{2'}$ is

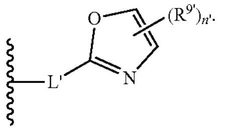

In some embodiments, $R^{2'}$ is

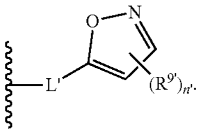

In some embodiments, $R^{2'}$ is

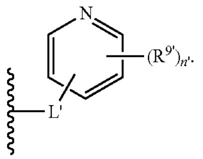

In some embodiments, $R^{2'}$ is

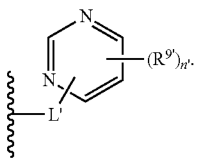

In some embodiments, $R^{2'}$ is

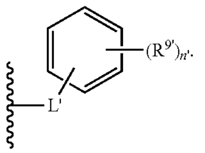

In some embodiments, $R^{2'}$ is

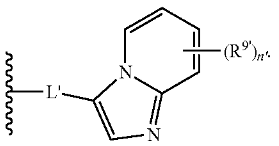

In some embodiments, $R^{2'}$ is hydrogen. In some embodiments, $R^{2'}$ is deuterium. In some embodiments, $R^{2'}$ is —$CH_3$. In some embodiments, $R^{2'}$ is —$CD_3$. In some embodiments, $R^{2'}$ is

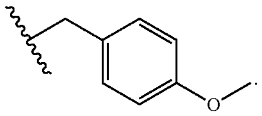 [SMILES: *Cc1ccc(OC)cc1]

In some embodiments, $R^{3'}$ is hydrogen. In some embodiments, $R^{3'}$ is halogen. In some embodiments, $R^{3'}$ is —R'. In some embodiments, $R^{3'}$ is —CN. In some embodiments, $R^{3'}$ is —$NO_2$. In some embodiments, $R^{3'}$ is —OH. In some embodiments, $R^{3'}$ is —OR'. In some embodiments, $R^{3'}$ is —$NR'_2$. In some embodiments, $R^{3'}$ is —NHR'. In some embodiments, $R^{3'}$ is —$NH_2$.

In some embodiments, $R^{3'}$ is

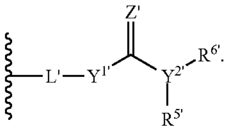

In some embodiments, $R^{3'}$ is

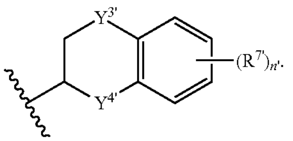

In some embodiments, $R^{3'}$ is

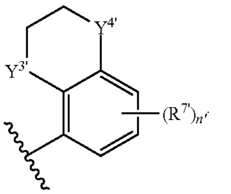

In some embodiments, $R^{3'}$ is

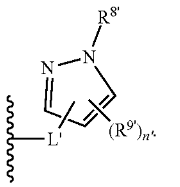

In some embodiments, $R^{3'}$ is

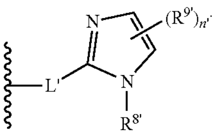

In some embodiments, $R^{3'}$ is

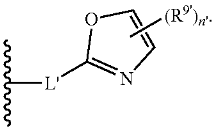

In some embodiments, $R^{3'}$ is

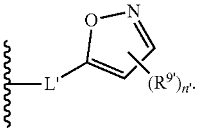

In some embodiments, $R^{3'}$ is

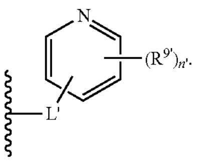

In some embodiments, $R^{3'}$ is

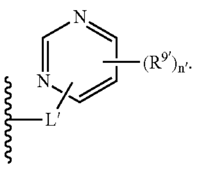

In some embodiments, $R^{3'}$ is

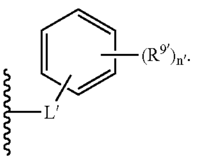

In some embodiments, $R^{3'}$ is

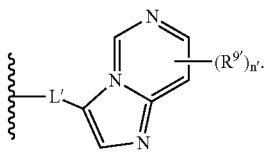

In some embodiments, $R^{3'}$ is hydrogen. In some embodiments, $R^{3'}$ is deuterium. In some embodiments, $R^{3'}$ is $—CH_3$. In some embodiments, $R^{3'}$ is $—CD_3$. In some embodiments, $R^{3'}$ is

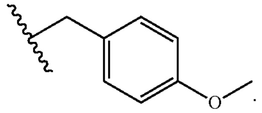 [SMILES: *Cc1ccc(OC)cc1]

In some embodiments, $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur.

In some embodiments, $R^{2'}$ and $R^{3'}$ together with the carbon form an optionally substituted 3-7 membered saturated carbocyclic ring.

In some embodiments, $R^{2'}$ and $R^{3'}$ together with the carbon form an optionally substituted 5-6 membered monocyclic heteroaryl ring having 1-4 heteroatoms independently selected from nitrogen, oxygen, and sulfur.

In some embodiments, $R^{2'}$ and $R^{3'}$ together with the carbon form an optionally substituted 3-7 membered saturated or a partially unsaturated monocyclic heterocyclic ring having 1-2 heteroatoms independently selected from nitrogen, oxygen, and sulfur.

In some embodiments, $R^{2'}$ and $R^{3'}$ together with the carbon form

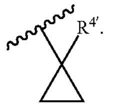

In some embodiments, $R^{2'}$ and $R^{3'}$ together with the carbon form

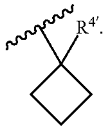

In some embodiments, $R^{2'}$ and $R^{3'}$ together with the carbon form

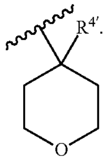

In some embodiments, $R^{2'}$ and $R^{3'}$ together with the carbon form

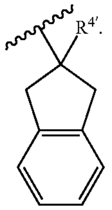

In some embodiments, $R^{4'}$ is hydrogen. In some embodiments, $R^{4'}$ is halogen. In some embodiments, $R^{4'}$ is —R'. In some embodiments, $R^{4'}$ is —CN. In some embodiments, $R^{4'}$ is —$NO_2$. In some embodiments, $R^{4'}$ is —OH. In some embodiments, $R^{4'}$ is —OR'. In some embodiments, $R^{4'}$ is —$NR'_2$. In some embodiments, $R^{4'}$ is —NHR'. In some embodiments, $R^{4'}$ is —$NH_2$. In some embodiments, $R^{4'}$ is —$CF_3$.

In some embodiments, $R^{4'}$ is

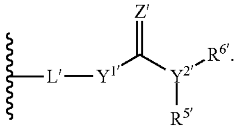

In some embodiments, $R^{4'}$ is

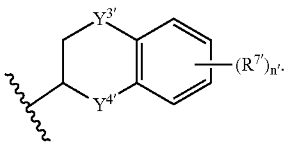

In some embodiments, $R^{4'}$ is

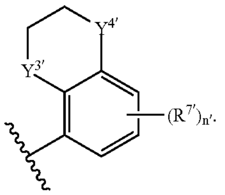

In some embodiments, $R^{4'}$ is

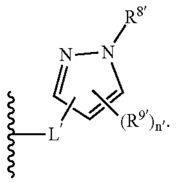

In some embodiments, $R^{4'}$ is

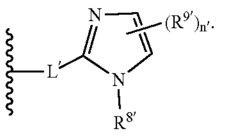

In some embodiments, $R^{4'}$ is

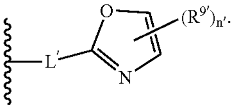

In some embodiments, $R^{4'}$ is

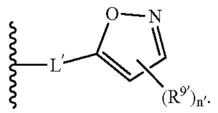

In some embodiments, $R^{4'}$ is

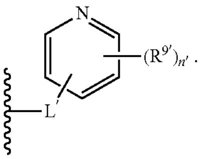

In some embodiments, $R^{4'}$ is

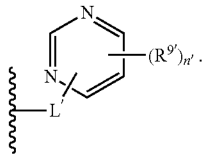

In some embodiments, $R^{4'}$ is

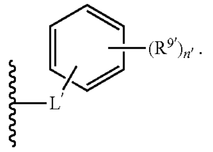

In some embodiments, $R^{4'}$ is

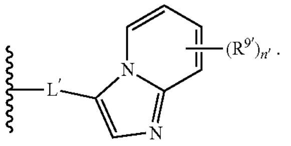

In some embodiments, $R^{4'}$ is hydrogen. In some embodiments, $R^{4'}$ is deuterium. In some embodiments, $R^{4'}$ is —$CH_3$. In some embodiments, $R^{4'}$ is —$CD_3$. some embodiments, $R^{4'}$ is

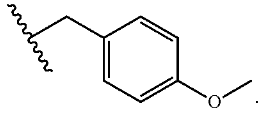 [SMILES: *Cc1ccc(OC)cc1]

In some embodiments, $R^{2'}$, $R^{3'}$, and $R^{4'}$, are each selected from those depicted in Table 1, below.

As defined above, L' is optionally substituted $C_{1-5}$ alkylene.

In some embodiments, L' is —$CH_2$—.

In some embodiments, L' is selected from those depicted in Table 1, below.

As defined above, $Y^{1'}$, $Y^{2'}$, $Y^{3'}$, and $Y^{4'}$ are each independently a covalent bond, a carbon, an oxygen; or a nitrogen, optionally substituted with hydrogen, an optionally substituted $C_{1-6}$ alkyl, or an optionally substituted 3-7 membered saturated carbocyclic ring.

In some embodiments, $Y^{1'}$ is a covalent bond. In some embodiments, $Y^{1'}$ is a carbon. In some embodiments, $Y^{1'}$ is an oxygen. In some embodiments, $Y^{1'}$ is a nitrogen, optionally substituted with hydrogen, an optionally substituted $C_{1-6}$ alkyl, or an optionally substituted 3-7 membered saturated carbocyclic ring.

In some embodiments, $Y^{2'}$ is a covalent bond. In some embodiments, $Y^{2'}$ is a carbon. In some embodiments, $Y^{2'}$ is an oxygen. In some embodiments, $Y^{2'}$ is a nitrogen, optionally substituted with hydrogen, an optionally substituted $C_{1-6}$ alkyl, or an optionally substituted 3-7 membered saturated carbocyclic ring.

In some embodiments, $Y^{3'}$ is a covalent bond. In some embodiments, $Y^{3'}$ is a carbon. In some embodiments, $Y^{3'}$ is an oxygen. In some embodiments, $Y^{3'}$ is a nitrogen, optionally substituted with hydrogen, an optionally substituted $C_{1-6}$ alkyl, or an optionally substituted 3-7 membered saturated carbocyclic ring.

In some embodiments, $Y^{3'}$ is a covalent bond. In some embodiments, $Y^{3'}$ is a carbon.

In some embodiments, $Y^{4'}$ is a covalent bond. In some embodiments, $Y^{4'}$ is a carbon. In some embodiments, $Y^{4'}$ is an oxygen. In some embodiments, $Y^{4'}$ is a nitrogen, optionally substituted with hydrogen, an optionally substituted $C_{1-6}$ alkyl, or an optionally substituted 3-7 membered saturated carbocyclic ring.

In some embodiments, $Y^{4'}$ is a covalent bond. In some embodiments, $Y^{4'}$ is a carbon.

In some embodiments, $Y^{1'}$, $Y^{2'}$ $Y^{3'}$, and $Y^{4'}$ are each selected from those depicted in Table 1, below.

As defined above, Z' is O or S.

In some embodiments, Z' is O. In some embodiments, Z' is S.

In some embodiments, Z' is selected from those depicted in Table 1, below.

As defined above, $R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur.

In some embodiments, $R^{5'}$ is hydrogen. In some embodiments, $R^{5'}$ is an optionally substituted $C_{1-6}$ alkyl.

In some embodiments, $R^{6'}$ is hydrogen. In some embodiments, $R^{6'}$ is an optionally substituted $C_{1-6}$ alkyl.

In some embodiments, $R^{5'}$ and $R^{6'}$ are cyclically linked and together with $Y^{2'}$ form an optionally substituted 3-7 membered saturated carbocyclic ring.

In some embodiments, $R^{5'}$ and $R^{6'}$ are cyclically linked and together with $Y^{2'}$ form an optionally substituted 5-6 membered monocyclic heteroaryl ring having 1-4 heteroatoms independently selected from nitrogen, oxygen, and sulfur.

In some embodiments, $R^{5'}$ and $R^{6'}$ are cyclically linked and together with $Y^{2'}$ form an optionally substituted 3-7 membered saturated or partially unsaturated monocyclic heterocyclic ring having 1-2 heteroatoms independently selected from nitrogen, oxygen, and sulfur.

In some embodiments, $R^{5'}$ and $R^{6'}$ are cyclically linked and together with $Y^{2'}$ form an optionally substituted 7-12 membered saturated or partially unsaturated bicyclic heterocyclic ring having 1-4 heteroatoms independently selected from nitrogen, oxygen, and sulfur.

In some embodiments, $R^{5'}$ and $R^{6'}$ are each selected from those depicted in Table 1, below.

As defined above, each $R^{7'}$ is independently —R', halogen, —CN, —$NO_2$, —OH, —$NR'_2$, —NHR', —$NH_2$, or —OR'.

In some embodiments, $R^{7'}$ is hydrogen. In some embodiments, $R^{7'}$ is halogen. In some embodiments, $R^{7'}$ is —CN. In some embodiments, $R^{7'}$ is —$NO_2$. In some embodiments, $R^{7'}$ is —OH. In some embodiments, $R^{7'}$ is —$NR'_2$. In some embodiments, $R^{7'}$ is —NHR'. In some embodiments, $R^{7'}$ is —$NH_2$. In some embodiments, $R^{7'}$ is —OR'.

In some embodiments, each $R^{7'}$ is independently selected from those depicted in Table 1, below.

As defined above, n' is an integer selected from 0 to 4.

In some embodiments, n' is 0. In some embodiments, n' is 1. In some embodiments, n' is 2. In some embodiments, n' is 3. In some embodiments, n' is 4.

As defined above, $R^{8'}$ is hydrogen, —CN, optionally substituted alkyl, or an optionally substituted aryl ring.

In some embodiments, $R^{8'}$ is hydrogen. In some embodiments, $R^{8'}$ is —CN. In some embodiments, $R^{8'}$ is an optionally substituted $C_{1-6}$ alkyl. In some embodiments, $R^{8'}$ is an optionally substituted aryl ring.

In some embodiments, $R^{8'}$ is selected from those depicted in Table 1, below.

As defined above, each $R^{9'}$ is independently hydrogen, halogen, —CN, —$OR^x$, —$NR'_2$, or optionally substituted alkyl.

In some embodiments, $R^{9'}$ is hydrogen. In some embodiments, $R^{9'}$ is halogen. In some embodiments, $R^{9'}$ is —CN. In some embodiments, $R^{9'}$ is —$OR^x$. In some embodiments, $R^{9'}$ is —$NR'_2$. In some embodiments, $R^{9'}$ is —NHR'. In some embodiments, $R^{9'}$ is —$NH_2$. In some embodiments, $R^{9'}$ is an optionally substituted $C_{1-6}$ alkyl.

In some embodiments, $R^{9'}$ is selected from those depicted in Table 1, below.

As defined above, $R^{10'}$ and $R^{11'}$ are each independently hydrogen or optionally substituted $C_{1-2}$ aliphatic. In some embodiments, $R^{10'}$ and $R^{11'}$ are each independently hydrogen, methyl, or ethyl.

In some embodiments, $R^{10'}$ is hydrogen. In some embodiment, $R^{10'}$ is an optionally substituted $C_1$ aliphatic. In some embodiment, $R^{10'}$ is methyl. In some embodiment, $R^{10'}$ is an optionally substituted $C_2$ aliphatic. In some embodiment, $R^{10'}$ is ethyl.

In some embodiments, $R^{10'}$ is selected from those depicted in Table 1, below.

In some embodiments, $R^{11'}$ is hydrogen. In some embodiment, $R^{11'}$ is an optionally substituted $C_1$ aliphatic. In some embodiment, $R^{11'}$ is methyl. In some embodiment, $R^{11'}$ is an optionally substituted $C_2$ aliphatic. In some embodiment, $R^{11'}$ is ethyl.

In some embodiments, $R^{11'}$ is selected from those depicted in Table 1, below.

Further disclosed herein is a β-agent compound according to Formula (II'):

Formula (II')

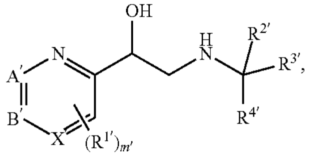

or a pharmaceutically acceptable salt thereof, wherein each of A', B', X', $R^{1'}$, $R^{2'}$, $R^{3'}$, $R^{4'}$, and m' is as defined above and as described in embodiments provided herein, both singly and in combination.

Further disclosed herein is a β-agent compound according to Formula (III'):

Formula (III')

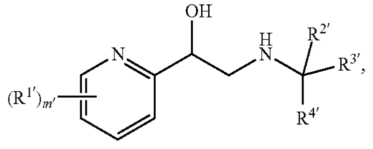

or a pharmaceutically acceptable salt thereof, wherein each of $R^1$, $R^{2'}$, $R^{3'}$, $R^{4'}$, and m' is as defined above and as described in embodiments provided herein, both singly and in combination.

Further disclosed herein is a β-agent compound according to Formula (IV'):

Formula (IV')

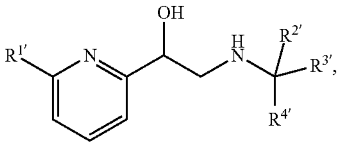

or a pharmaceutically acceptable salt thereof, wherein each of $R^{1'}$, $R^{2'}$, $R^{3'}$, and $R^{4'}$ is as defined above and as described in embodiments provided herein, both singly and in combination. In some such embodiments, $R^{1'}$ is —$CF_3$. In some such embodiments, $R^{1'}$ is —$CF_2H$. In some such embodiments, $R^{1'}$ is —$OCF_3$. In some such embodiments, $R^{1'}$ is —CN. In some such embodiments, $R^{1'}$ is —C(O)$NR'_2$. In some such embodiments, $R^{1'}$ is a cyclopropyl group. In some such embodiments, $R^{1'}$ is a tetrazole. In some such embodiments, $R^{1'}$ is phenyl. In some such embodiments, $R^{1'}$ is —Br. In some such embodiments, $R^{1'}$ is —$CH_3$.

Further disclosed herein is a β-agent compound according to Formula (V'):

Formula (V')

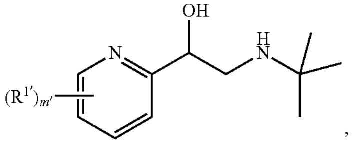

or a pharmaceutically acceptable salt thereof, wherein each of $R^{1'}$ and m' is as defined above and as described in embodiments provided herein, both singly and in combination.

Further disclosed herein is a β-agent compound according to Formula (VI'):

Formula (VI')

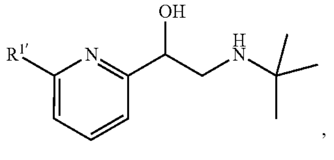

or a pharmaceutically acceptable salt thereof, wherein $R^{1'}$ is as defined above and as described in embodiments provided herein, both singly and in combination.

Further disclosed herein is a β-agent compound according to Formula (VII'):

Formula (VII')

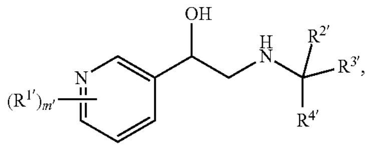

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a β-agent compound according to Formula (VIII'):

Formula (VIII')

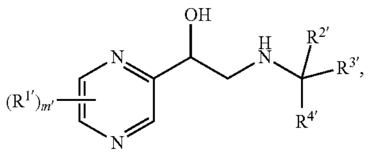

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a β-agent compound according to Formula (IX'):

Formula (IX')

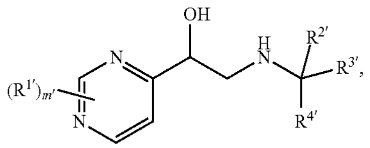

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a β-agent compound according to Formula (X'):

Formula (X'),

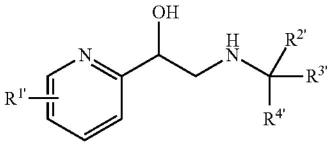

or a pharmaceutically acceptable salt thereof, wherein $R^{1'}$ is halogen, —$R^x$, —CN, —$NO_2$, —$SF_5$, —$OR^x$, —$SO_2R'$, or —C(O)R';

$R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring; and R' and $R^x$ are as defined above and as described in embodiments provided herein, both singly and in combination. In some such embodiments, $R^{1'}$ is —$CF_3$. In some such embodiments, $R^{1'}$ is —$CF_2H$. In some such embodiments, $R^{1'}$ is —$OCF_3$. In some such embodiments, $R^{1'}$ is —CN. In some such embodiments, $R^{1'}$ is —C(O)$NR'_2$. In some such embodiments, $R^{1'}$ is a cyclopropyl group. In some such embodiments, $R^{1'}$ is a tetrazole. In some such embodiments, $R^{1'}$ is phenyl. In some such embodiments, $R^{1'}$ is —Br. In some such embodiments, $R^{1'}$ is —$CH_3$.

Further disclosed herein is a β-agent compound according to Formula (XI'):

Formula (XI')

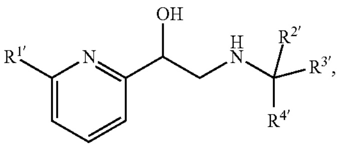

or a pharmaceutically acceptable salt thereof, wherein:

$R^{1'}$ is halogen, —R', —CN, —$NO_2$, —$SF_5$, —$OR^x$, —$SO_2R'$, or —C(O)R';

$R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring; and R' and $R^x$ are as defined above and as described in embodiments provided herein, both singly and in combination.

Further disclosed herein is a β-agent compound according to Formula (XII'):

Formula (XII')

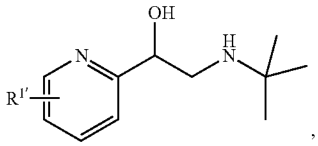

, or a pharmaceutically acceptable salt thereof, wherein:

$R^{1'}$ is halogen, —R', —CN, —$NO_2$, —$SF_5$, —$OR^x$, —$SO_2R'$, or —C(O)R'; and R' and $R^x$ are as defined above and as described in embodiments provided herein, both singly and in combination.

Further disclosed herein is a compound according to Formula (XIII'):

Formula (XIII')

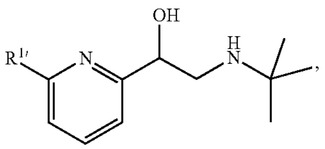

or a pharmaceutically acceptable salt thereof, wherein:

$R^{1'}$ is halogen, —R', —CN, —$NO_2$, —$SF_5$, —$OR^x$, —$SO_2R'$, or —C(O)R'; and R' and $R^x$ are as defined above and as described in embodiments provided herein, both singly and in combination.

Further disclosed herein is a β-agent compound according to Formula (XIV'):

Formula (XIV')

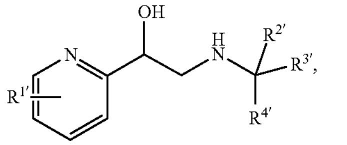

or a pharmaceutically acceptable salt thereof, wherein $R^{1'}$ is halogen, —R', —CN, or —$NO_2$;

$R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring; and R' is as defined above and as described in embodiments provided herein, both singly and in combination.

Further disclosed herein is a compound according to Formula (XV'):

Formula (XV')

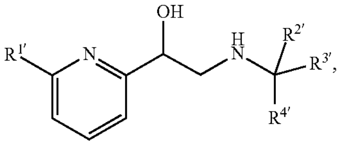

or a pharmaceutically acceptable salt thereof, wherein:

$R^{1'}$ is halogen, —R', —CN, or —$NO_2$;

$R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring; and R' is as defined above and as described in embodiments provided herein, both singly and in combination.

Further disclosed herein is a compound according to Formula (XVI'):

Formula (XVI')

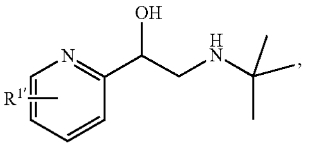

or a pharmaceutically acceptable salt thereof, wherein:

$R^{1'}$ is halogen, —R', —CN, or —$NO_2$; and

R' is as defined above and as described in embodiments provided herein, both singly and in combination.

Further disclosed herein is a compound according to Formula (XVII'):

Formula (XVII')

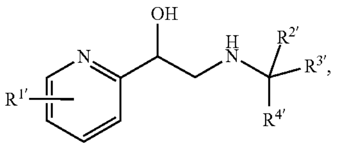

or a pharmaceutically acceptable salt thereof, wherein $R^{1'}$ is halogen, —R', —CN, or —$NO_2$;

each R' is an optionally substituted $C_{1-6}$ aliphatic; and $R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring.

Further disclosed herein is a compound according to Formula (XVIII'):

Formula (XVIII')

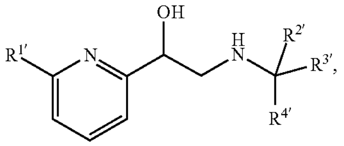

or a pharmaceutically acceptable salt thereof, wherein:

$R^{1'}$ is halogen, —R', —CN, or —$NO_2$;

each R' is an optionally substituted $C_{1-6}$ aliphatic; and $R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring.

Further disclosed herein is a compound according to Formula (XIX'):

Formula (XIX')

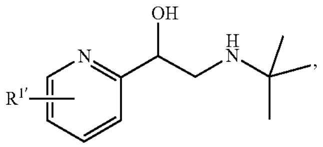

or a pharmaceutically acceptable salt thereof, wherein:

$R^{1'}$ is halogen, —R', —CN, or —$NO_2$; and

R' is optionally substituted $C_{1-6}$ aliphatic.

Further disclosed herein is a compound according to Formula (XX'):

Formula (XX')

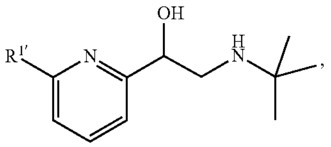

or a pharmaceutically acceptable salt thereof,
wherein:

$R^{1'}$ is halogen, —R', —CN, or —$NO_2$; and

R' is an optionally substituted $C_{1-6}$ aliphatic.

Further disclosed herein is a compound according to Formula (XXI'):

Formula (XXI')

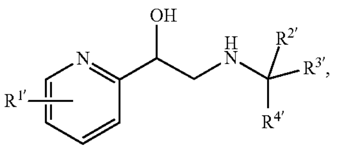

or a pharmaceutically acceptable salt thereof,
wherein $R^{1'}$ is halogen, —R', —CN, or —$NO_2$;

each R' is an optionally substituted $C_{1-6}$ aliphatic; and $R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring.

Further disclosed herein is a compound according to Formula (XXII'):

Formula (XXII')

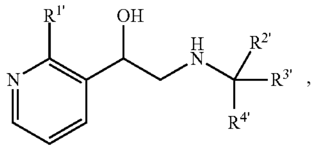

or a pharmaceutically acceptable salt thereof,
wherein:

$R^{1'}$ is halogen, —R', —CN, or —$NO_2$;

each R' is an optionally substituted $C_{1-6}$ aliphatic; and $R^{2'}$, $R^{3'}$, and $R^{4'}$ are each independently halogen, —R', —CN, —$NO_2$, —OR', or —$NR'_2$, or $R^{2'}$ and $R^{3'}$ together with the carbon form an optionally substituted 3-7 membered cycloalkyl or heterocycle ring.

Further disclosed herein is a compound according to Formula (XXIII'):

Formula (XXIII')

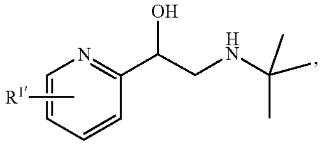

or a pharmaceutically acceptable salt thereof,
wherein:

$R^{1'}$ is halogen, —R', —CN, or —$NO_2$; and

R' is optionally substituted $C_{1-6}$ aliphatic.

Further disclosed herein is a compound according to Formula (XXIV'):

Formula (XXIV')

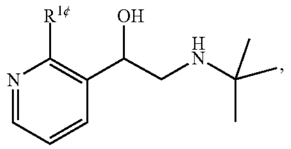

or a pharmaceutically acceptable salt thereof,
wherein:

$R^{1'}$ is halogen, —R', —CN, or —$NO_2$; and

R' is an optionally substituted $C_{1-6}$ aliphatic.

Further disclosed herein is a compound according to Formula (XXV'):

Formula (XXV')

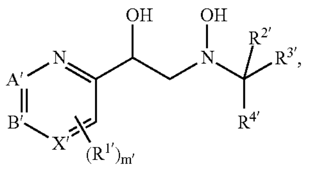

or a pharmaceutically acceptable salt thereof,
wherein each of A', B', X', $R^{1'}$, $R^{2'}$, $R^{3'}$, $R^{4'}$, and m' is as defined above and as described in embodiments provided herein, both singly and in combination.

| Compound No. | Chemical Structure | MS (m/z) (M + 1) |
|---|---|---|
| 03-1 | 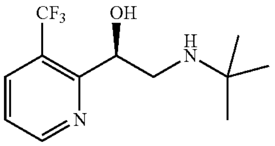 [SMILES: CC(C)(C)NC[C@H](O)c1ncccc1C(F)(F)F] | 263.2 |
| 03-2 | 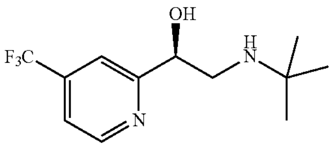 [SMILES: CC(C)(C)NC[C@H](O)c1cc(C(F)(F)F)ccn1] | 263.2 |

-continued
| Compound No. | Chemical Structure | MS (m/z) (M + 1) |
| --- | --- | --- |
| 03-3 | 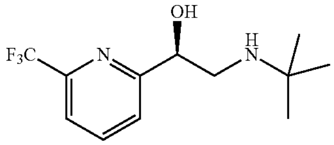 [SMILES: CC(C)(C)NC[C@H](O)c1cccc(C(F)(F)F)n1] | 263.2 |
| 03-4 | 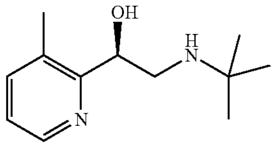 | 209.2 |
| 03-5 | 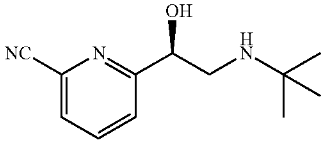 [SMILES: CC(C)(C)NC[C@H](O)c1cccc(C#N)n1] | 220.24 |
| 03-6 | 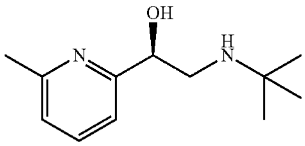 | 209.32 |
| 03-7 | 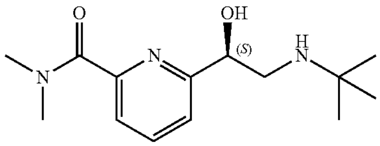 | 266.1 |
| 03-8 | 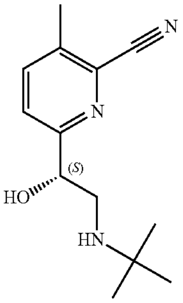 | 234.23 |
| 03-9 | 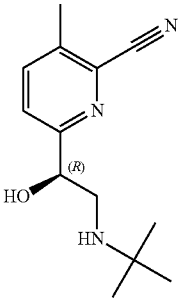 | 234.23 |
| 03-10 | 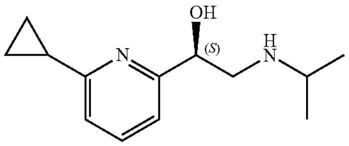 | 221.1 |

-continued
| Compound No. | Chemical Structure | MS (m/z) (M + 1) |
| --- | --- | --- |
| 03-11 | 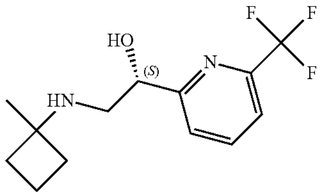 | 275.17 |
| 03-12 | 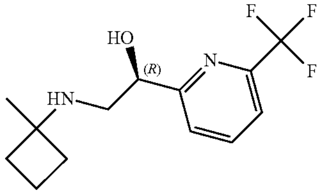 | 275.17 |
| 03-13 | 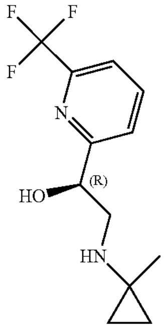 | 261.14 |
| 03-14 | 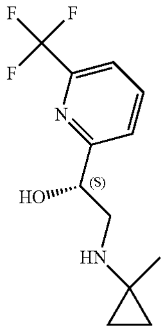 | 261.14 |
| 03-15 | 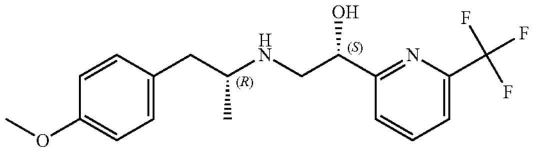 | 355.32 |
| 03-16 | 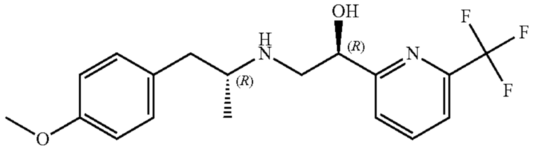 | 355.32 |
| 03-17 | 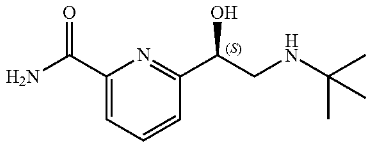 | 238.1 |

-continued
| Compound No. | Chemical Structure | MS (m/z) (M + 1) |
|---|---|---|
| 03-18 | 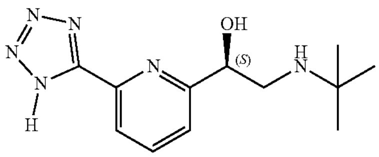 | 263.2 |
| 03-19 | 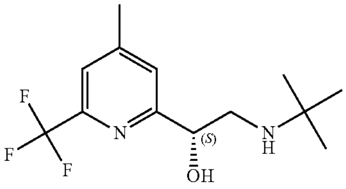 | 277.1 |
| 03-20 | 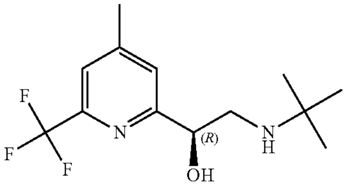 | 277.1 |
| 03-21 | 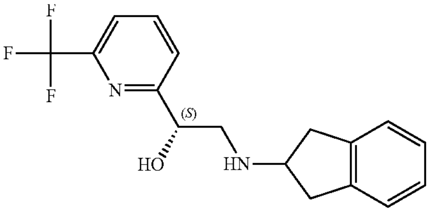 | 323.27 |
| 03-22 | 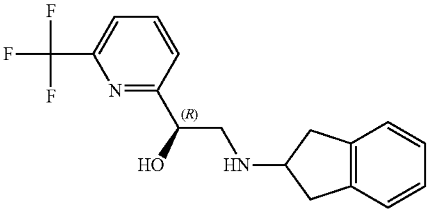 | 323.27 |
| 03-23 | 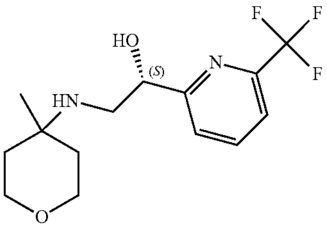 | 305.25 |
| 03-24 | 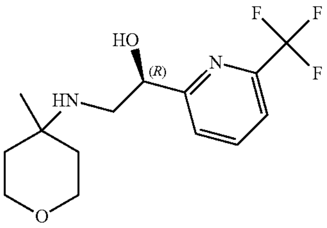 | 305.25 |

-continued
| Compound No. | Chemical Structure | MS (m/z) (M + 1) |
|---|---|---|
| 03-25 | 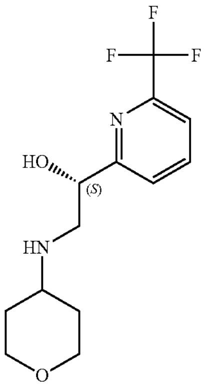 | 291.18 |
| 03-26 | 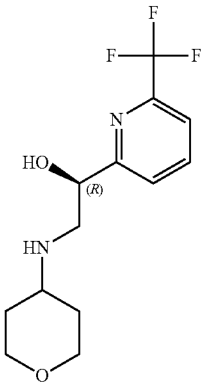 | 291.18 |
| 03-28 | 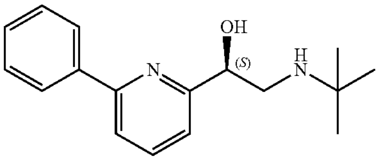 | 271.1 |
| 03-29 | 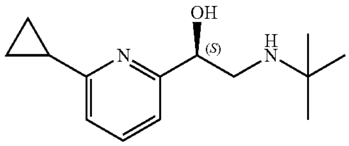 | 253.2 |
| 03-30 | 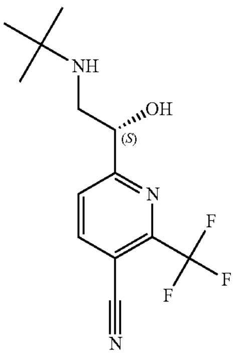 | 288.25 |

-continued
| Compound No. | Chemical Structure | MS (m/z) (M + 1) |
|---|---|---|
| 03-31 | 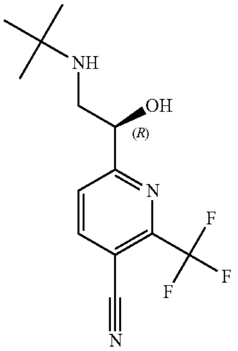 | 288.25 |
| 03-32 | 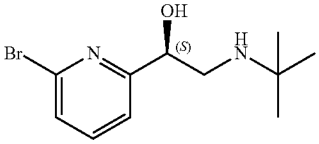 | 273.1 |
| 03-33 | 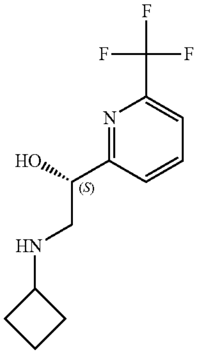 | 261.24 |
| 03-34 | 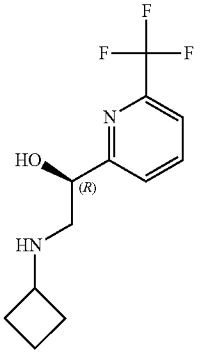 | 261.24 |
| 03-35 | 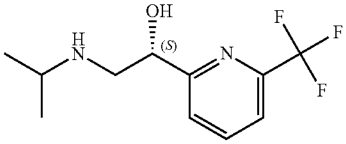 | 249.17 |
| 03-36 | 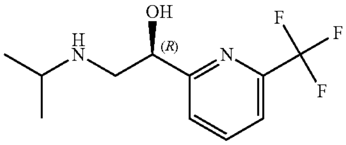 | 249.17 |

-continued
| Compound No. | Chemical Structure | MS (m/z) (M + 1) |
|---|---|---|
| 03-37 | 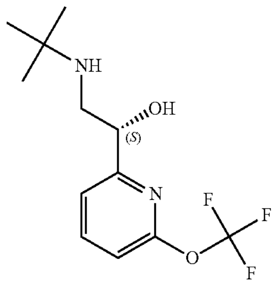 | 279.17 |
| 03-38 | 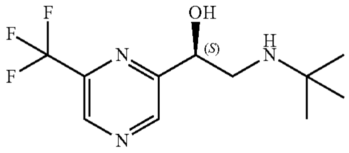 | 264.1 |
| 03-43 | 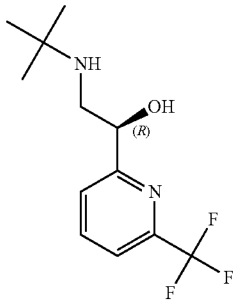 | 263.2 |
| 03-44 | 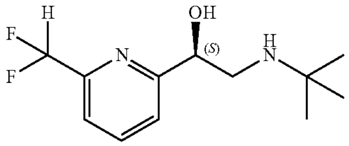 | 245.1 |
| 03-45 | 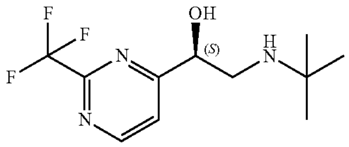 | 264.1 |
| 03-46 | 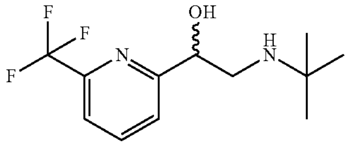 [SMILES: CC(C)(C)NCC(O)c1cccc(C(F)(F)F)n1] | 263.1 |
| 03-47 | 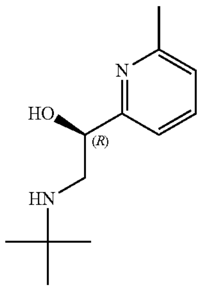 | 209.32 |

-continued
| Compound No. | Chemical Structure | MS (m/z) (M + 1) |
|---|---|---|
| 03-48 | 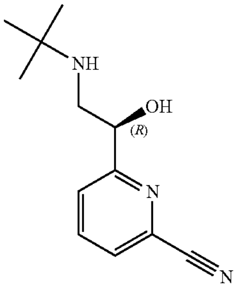 | 220.25 |
| 03-49 | 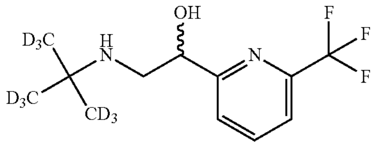 [SMILES: [2H]C([2H])([2H])C(NCC(O)c1cccc(C(F)(F)F)n1)(C([2H])([2H])[2H])C([2H])([2H])[2H]] | 272.1 |
| 03-50 | 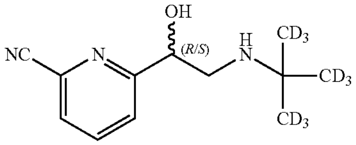 [SMILES: [2H]C([2H])([2H])C(NCC(O)c1cccc(C#N)n1)(C([2H])([2H])[2H])C([2H])([2H])[2H]] | 229.2 |
| 03-51 | 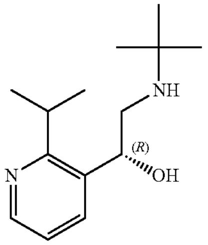 | 237.2 |
| 03-52 | 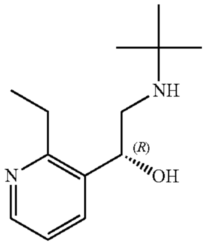 | 223.2 |
| 03-53 | 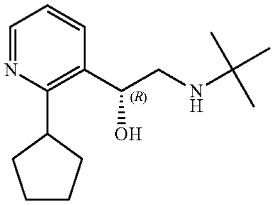 | 263.2 |
| 03-54 | 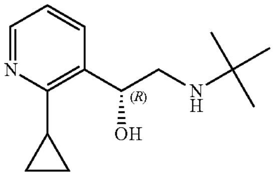 | 235.3 |

-continued
| Compound No. | Chemical Structure | MS (m/z) (M + 1) |
|---|---|---|
| 03-55 | 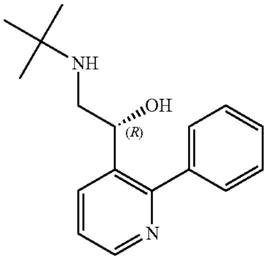 | 271.4 |
| 03-56 | 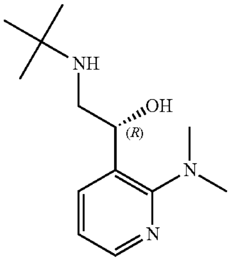 | 238.2 |
| 03-57 | 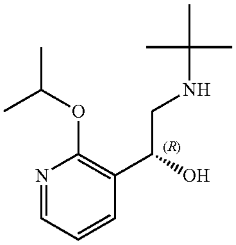 | 253.2 |
| 03-58 | 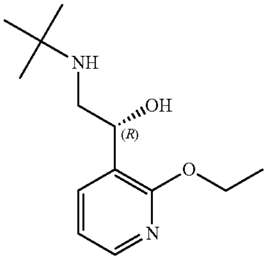 | 239.2 |
| 03-59 | 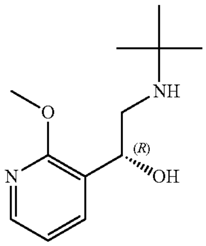 | 225.2 |
| 03-60 | 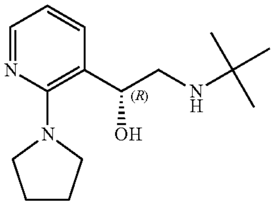 | 264.2 |

-continued
| Compound No. | Chemical Structure | MS (m/z) (M + 1) |
| --- | --- | --- |
| 03-61 | 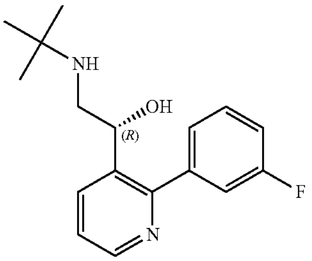 | 289.3 |
| 03-62 | 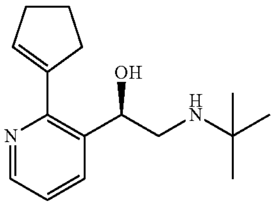 [SMILES: CC(C)(C)NC[C@H](O)c1cccnc1C1=CCCC1] | 261.4 |
| 03-63 | 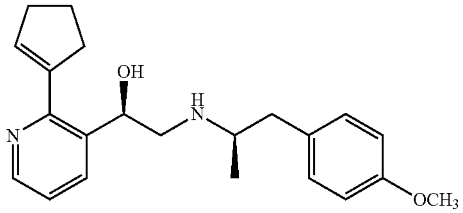 [SMILES: COc1ccc(C[C@@H](C)NC[C@H](O)c2cccnc2C2=CCCC2)cc1] | 353.5 |
| 03-64 | 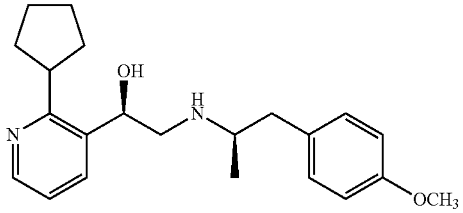 [SMILES: COc1ccc(C[C@@H](C)NC[C@H](O)c2cccnc2C2CCCC2)cc1] | 355.5 |
| 03-65 | 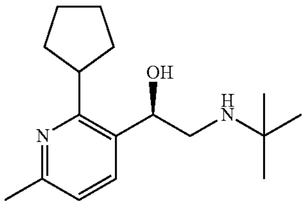 [SMILES: Cc1ccc([C@@H](O)CNC(C)(C)C)c(C2CCCC2)n1] | 277.4 |
| 03-66 | 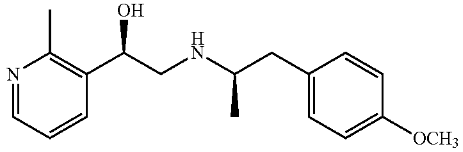 [SMILES: COc1ccc(C[C@@H](C)NC[C@H](O)c2cccnc2C)cc1] | 301.3 |
| 03-67 | 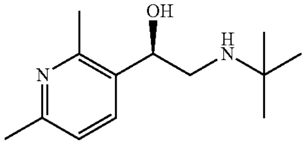 [SMILES: Cc1ccc([C@@H](O)CNC(C)(C)C)c(C)n1] | 223.3 |

-continued
| Compound No. | Chemical Structure | MS (m/z) (M + 1) |
|---|---|---|
| 03-68 | 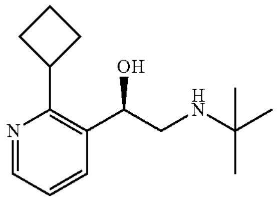 [SMILES: CC(C)(C)NC[C@H](O)c1cccnc1C1CCC1] | 249.3 |
| 03-70 | 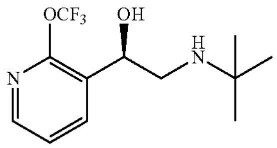 [SMILES: CC(C)(C)NC[C@H](O)c1cccnc1OC(F)(F)F] | 279.3 |
| 03-71 | 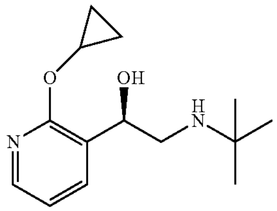 [SMILES: CC(C)(C)NC[C@H](O)c1cccnc1OC1CC1] | 251.3 |
| 03-72 | 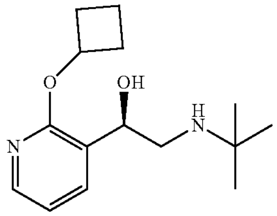 [SMILES: CC(C)(C)NC[C@H](O)c1cccnc1OC1CCC1] | 265.3 |
| 03-73 | 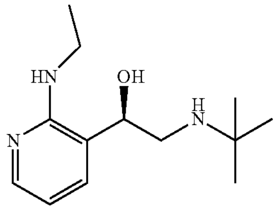 [SMILES: CCNc1ncccc1[C@@H](O)CNC(C)(C)C] | 238.4 |
| 03-74 | 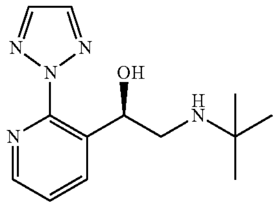 [SMILES: CC(C)(C)NC[C@H](O)c1cccnc1-n1nccn1] | 262.2 |
| 03-75 | 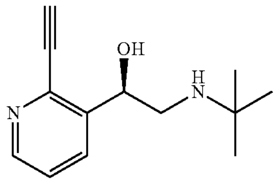 [SMILES: C#Cc1ncccc1[C@@H](O)CNC(C)(C)C] | 219.3 |

-continued
| Compound No. | Chemical Structure | MS (m/z) (M + 1) |
|---|---|---|
| 03-76 | 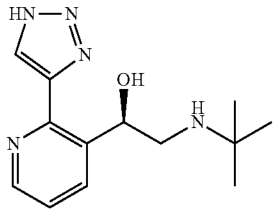 [SMILES: CC(C)(C)NC[C@H](O)c1cccnc1-c1c[nH]nn1] | 262.3 |
| 03-77 | 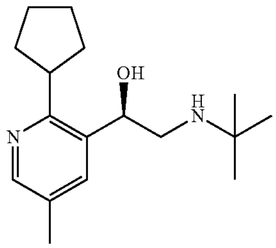 [SMILES: Cc1cnc(C2CCCC2)c([C@@H](O)CNC(C)(C)C)c1] | 277.4 |
| 03-78 | 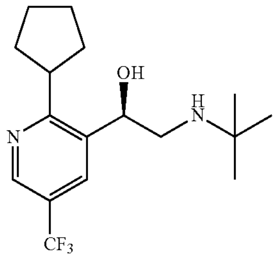 [SMILES: CC(C)(C)NC[C@H](O)c1cc(C(F)(F)F)cnc1C1CCCC1] | 331.3 |
| 03-79 | 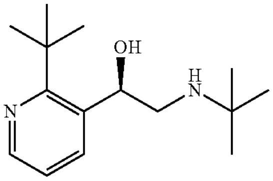 [SMILES: CC(C)(C)NC[C@H](O)c1cccnc1C(C)(C)C] | 251.4 |
| 03-80 | 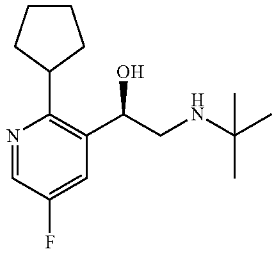 [SMILES: CC(C)(C)NC[C@H](O)c1cc(F)cnc1C1CCCC1] | 281.4 |
| 03-81 | 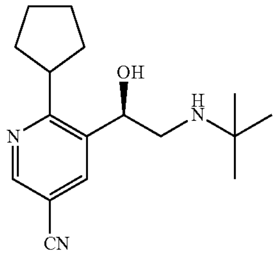 [SMILES: CC(C)(C)NC[C@H](O)c1cc(C#N)cnc1C1CCCC1] | |

-continued
| Compound No. | Chemical Structure | MS (m/z) (M + 1) |
|---|---|---|
| 03-82 | 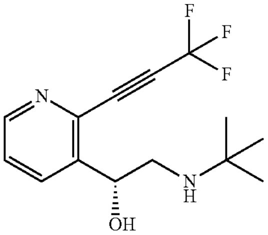 [SMILES: CC(C)(C)NC[C@H](O)c1cccnc1C#CC(F)(F)F] | |
| 03-83 | 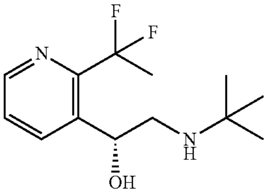 [SMILES: CC(C)(C)NC[C@H](O)c1cccnc1C(C)(F)F] | 259.3 |
| 03-84 | 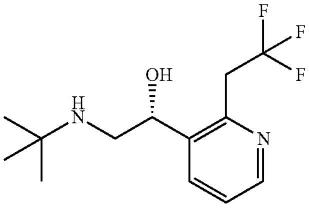 [SMILES: CC(C)(C)NC[C@H](O)c1cccnc1CC(F)(F)F] | 277.3 |
| 03-85 | 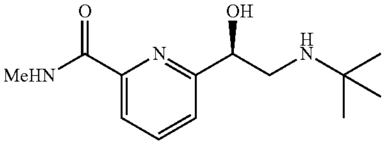 [SMILES: CNC(=O)c1cccc([C@@H](O)CNC(C)(C)C)n1] | 252.2 |
| 03-86 | 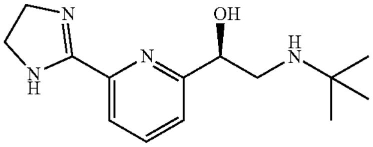 [SMILES: CC(C)(C)NC[C@H](O)c1cccc(C2=NCCN2)n1] | 263.1 |
| 03-87 | 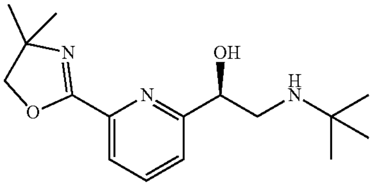 [SMILES: CC1(C)COC(c2cccc([C@@H](O)CNC(C)(C)C)n2)=N1] | |
| 03-88 | 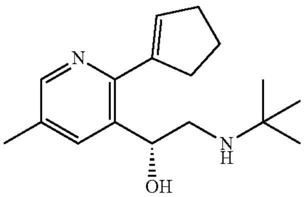 [SMILES: Cc1cnc(C2=CCCC2)c([C@@H](O)CNC(C)(C)C)c1] | 275.3 |
| 03-89 | 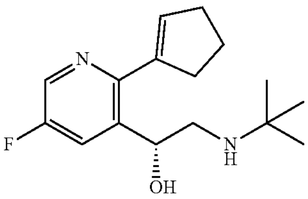 [SMILES: CC(C)(C)NC[C@H](O)c1cc(F)cnc1C1=CCCC1] | 279.4 |

-continued
| Compound No. | Chemical Structure | MS (m/z) (M + 1) |
|---|---|---|
| 03-90 | 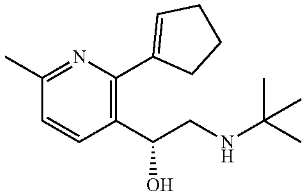 [SMILES: Cc1ccc([C@@H](O)CNC(C)(C)C)c(C2=CCCC2)n1] | 275.4 |
| 03-91 | 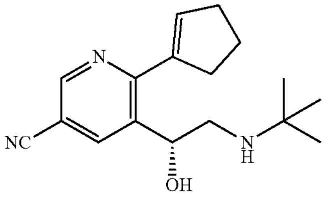 [SMILES: CC(C)(C)NC[C@H](O)c1cc(C#N)cnc1C1=CCCC1] | |
| 03-92 | 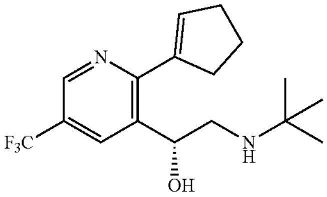 [SMILES: CC(C)(C)NC[C@H](O)c1cc(C(F)(F)F)cnc1C1=CCCC1] | 329.4 |
| 03-93 | 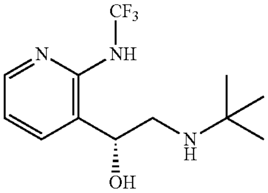 [SMILES: CC(C)(C)NC[C@H](O)c1cccnc1NC(F)(F)F] | |
| 03-94 | 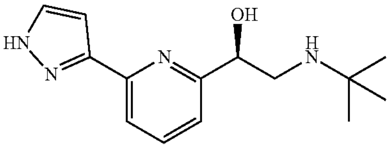 [SMILES: CC(C)(C)NC[C@H](O)c1cccc(-c2cc[nH]n2)n1] | |
| 03-95 | 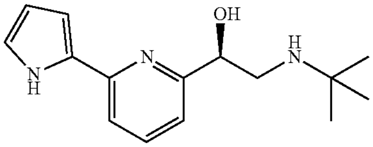 [SMILES: CC(C)(C)NC[C@H](O)c1cccc(-c2ccc[nH]2)n1] | 260.2 |
| 03-96 | 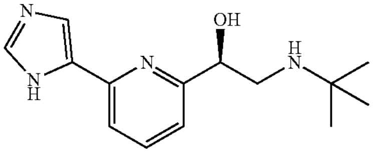 [SMILES: CC(C)(C)NC[C@H](O)c1cccc(-c2cnc[nH]2)n1] | |
| 03-97 | 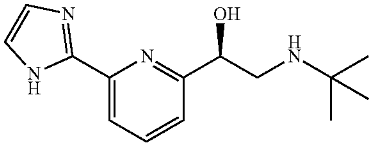 [SMILES: CC(C)(C)NC[C@H](O)c1cccc(-c2ncc[nH]2)n1] | |

-continued
| Compound No. | Chemical Structure | MS (m/z) (M + 1) |
|---|---|---|
| 03-98 | 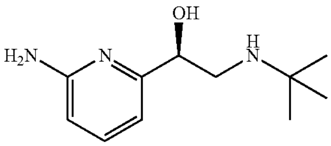 | 210.1 |
| 03-99 | 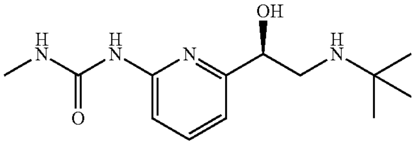 [SMILES: CNC(=O)Nc1cccc([C@@H](O)CNC(C)(C)C)n1] | |
| 03-100 | 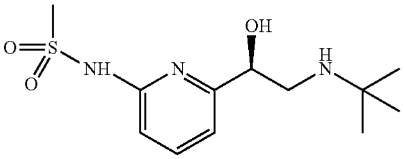 [SMILES: CC(C)(C)NC[C@H](O)c1cccc(NS(C)(=O)=O)n1] | |
| 03-101 | 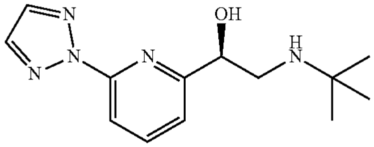 [SMILES: CC(C)(C)NC[C@H](O)c1cccc(-n2nccn2)n1] | 262.2 |
| 03-102 | 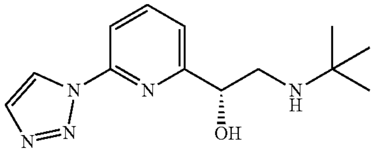 [SMILES: CC(C)(C)NC[C@H](O)c1cccc(-n2ccnn2)n1] | 262.2 |
| 03-103 | 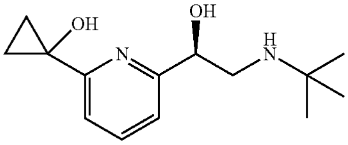 [SMILES: CC(C)(C)NC[C@H](O)c1cccc(C2(O)CC2)n1] | |
| 03-104 | 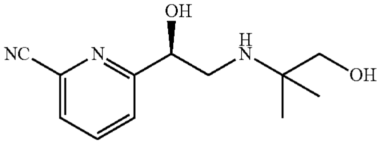 [SMILES: CC(C)(CO)NC[C@H](O)c1cccc(C#N)n1] | 236.2 |
| 03-105 | 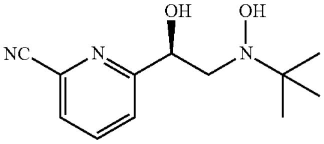 [SMILES: CC(C)(C)N(O)C[C@H](O)c1cccc(C#N)n1] | |
| 03-106 | 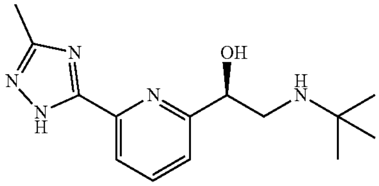 [SMILES: Cc1n[nH]c(-c2cccc([C@@H](O)CNC(C)(C)C)n2)n1] | |

-continued
| Compound No. | Chemical Structure | MS (m/z) (M + 1) |
| --- | --- | --- |
| 03-107 | 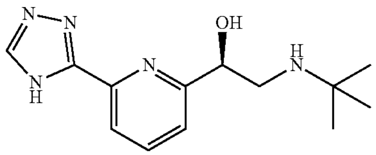 [SMILES: CC(C)(C)NC[C@H](O)c1cccc(-c2nnc[nH]2)n1] | |
| 03-108 | 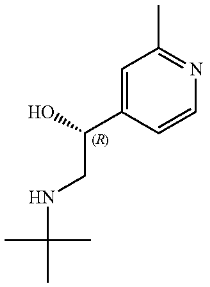 | 209.2 |
| 03-109 | 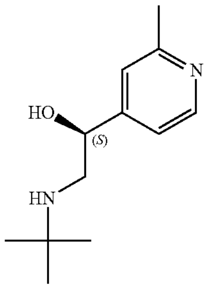 | 209.2 |
| 03-110 | 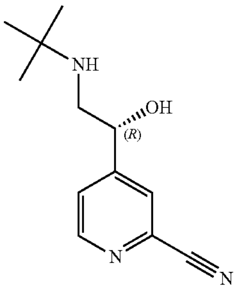 | 220.2 |
| 03-111 | 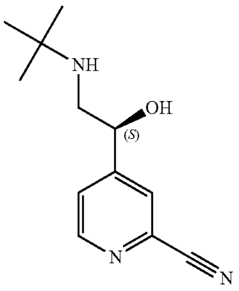 | 220.2 |

-continued
| Compound No. | Chemical Structure | MS (m/z) (M + 1) |
| --- | --- | --- |
| 03-112 | 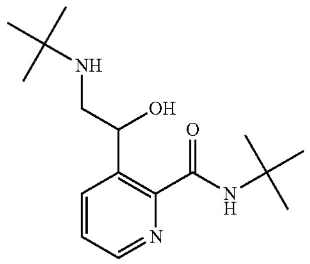 [SMILES: CC(C)(C)NCC(O)c1cccnc1C(=O)NC(C)(C)C] | 294.2 |
| 03-113 | 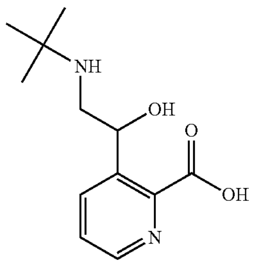 [SMILES: CC(C)(C)NCC(O)c1cccnc1C(=O)O] | 239.23 |
| 03-114 | 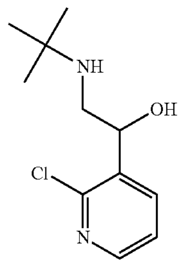 | 229.1 |
| 03-115 | 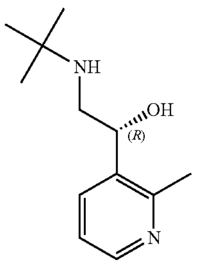 | 209.2 |
| 03-116 | 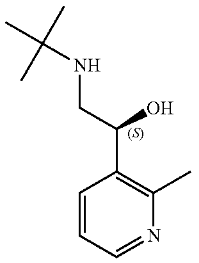 | 209.2 |

-continued
| Compound No. | Chemical Structure | MS (m/z) (M + 1) |
|---|---|---|
| 03-117 | 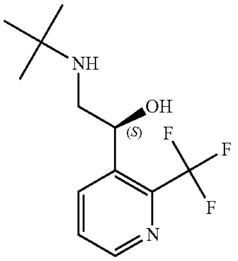 | 263.2 |
| 03-118 | 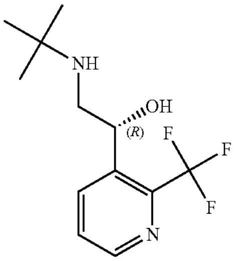 | 263.2 |
| 03-119 | 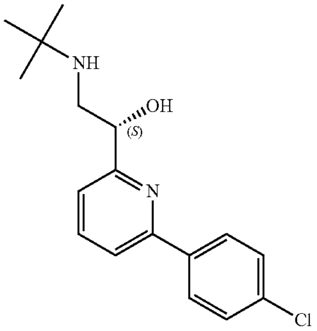 | 305.37 |
| 03-120 | 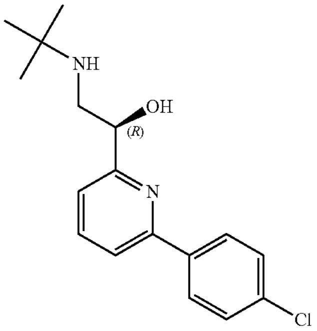 | 305.37 |
| 03-121 | 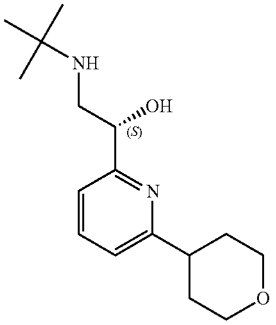 | 279.3 |

-continued
| Compound No. | Chemical Structure | MS (m/z) (M + 1) |
|---|---|---|
| 03-122 | 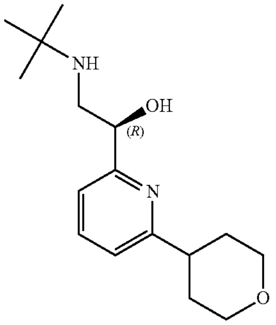 | 279.3 |
| 03-123 | 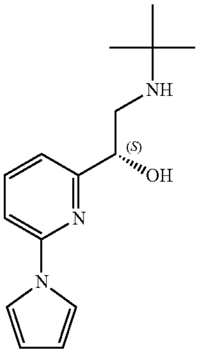 | 260.27 |
| 03-124 | 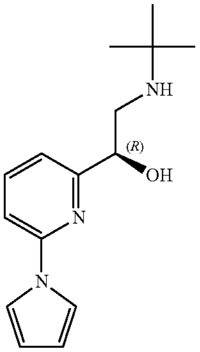 | 260.23 |
| 03-125 | 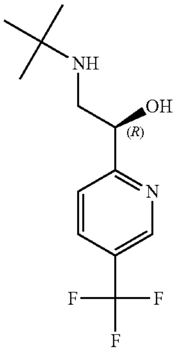 | 263.1 |

-continued
| Compound No. | Chemical Structure | MS (m/z) (M + 1) |
|---|---|---|
| 03-126 | 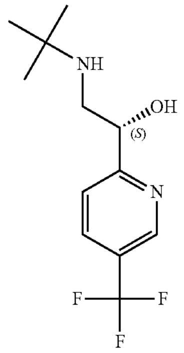 | 263.1 |
| 03-127 | 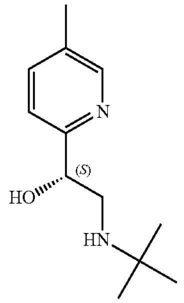 | 209.1 |
| 03-128 | 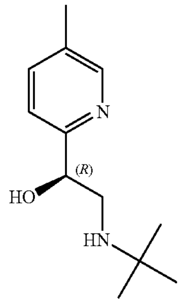 | 209.1 |
| 03-129 | 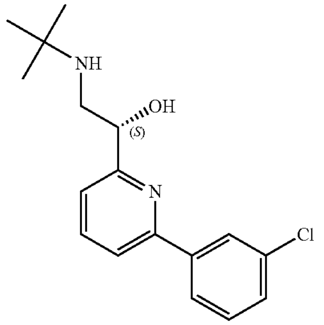 | 305.32 |

-continued
| Compound No. | Chemical Structure | MS (m/z) (M + 1) |
|---|---|---|
| 03-130 | 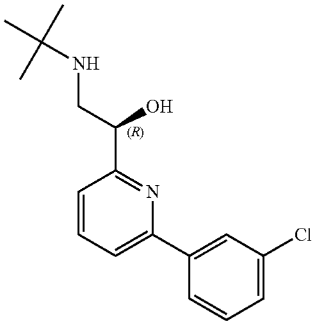 | 305.35 |
| 03-131 | 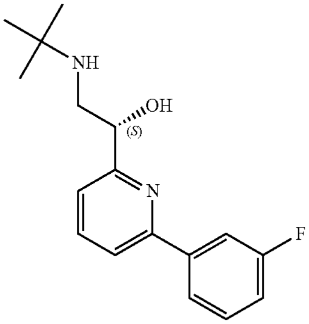 | 289.35 |
| 03-132 | 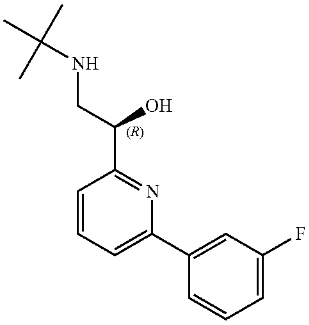 | 289.32 |
| 03-133 | 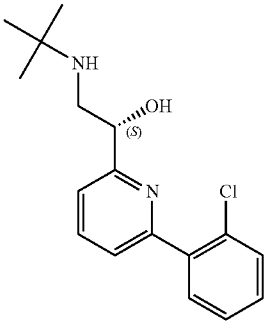 | 305.28 |

-continued
| Compound No. | Chemical Structure | MS (m/z) (M + 1) |
|---|---|---|
| 03-134 | 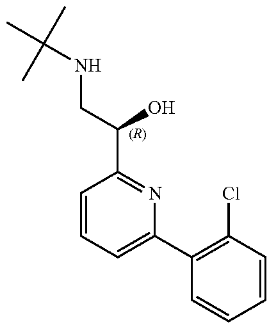 | 305.28 |
| 03-135 | 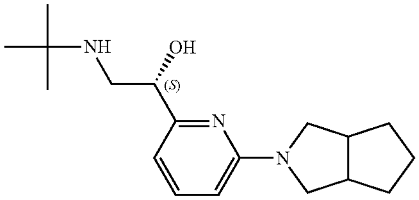 | 304.4 |
| 03-136 | 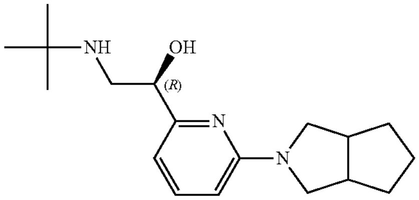 | 304.4 |
| 03-137 | 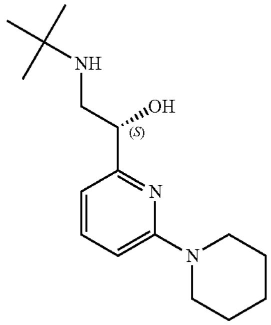 | 278.41 |
| 03-138 | 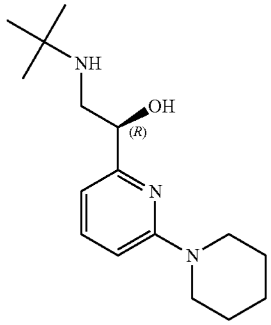 | 278.41 |

-continued
| Compound No. | Chemical Structure | MS (m/z) (M + 1) |
| --- | --- | --- |
| 03-139 | 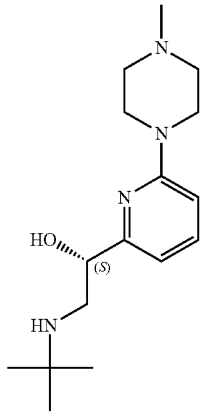 | 293.42 |
| 03-140 | 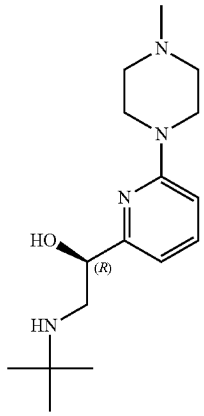 | 293.42 |
| 03-141 | 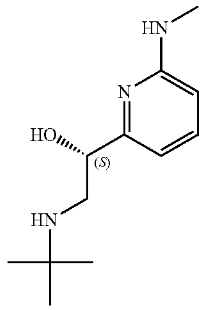 | 224.25 |
| 03-142 | 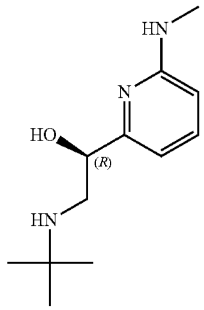 | 224.25 |

-continued
| Compound No. | Chemical Structure | MS (m/z) (M + 1) |
|---|---|---|
| 03-143 | 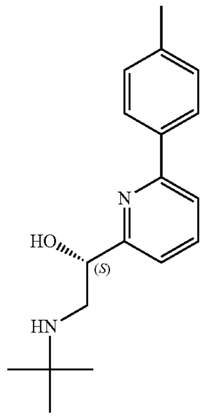 | 285.22 |
| 03-144 | 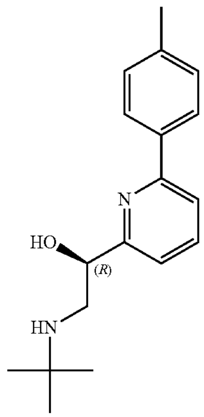 | 285.22 |
| 03-145 | 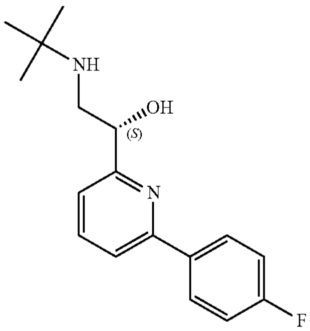 | 289.38 |
| 03-146 | 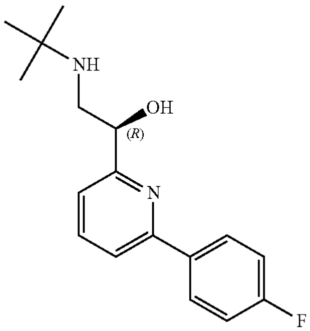 | 289.38 |

-continued
| Compound No. | Chemical Structure | MS (m/z) (M + 1) |
| --- | --- | --- |
| 03-147 | 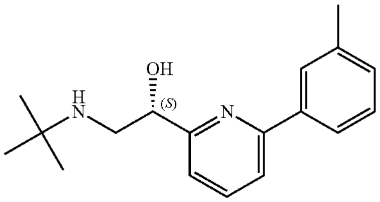 | 285.35 |
| 03-148 | 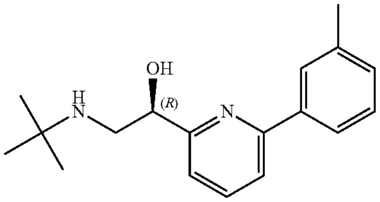 | 285.35 |
| 03-149 | 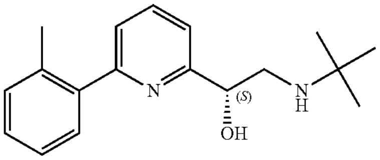 | 285.33 |
| 03-150 | 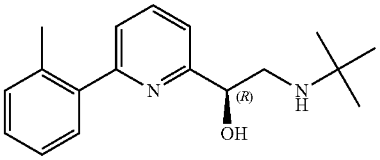 | 285.33 |
| 03-151 | 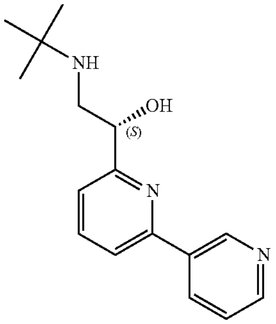 | 272.33 |
| 03-152 | 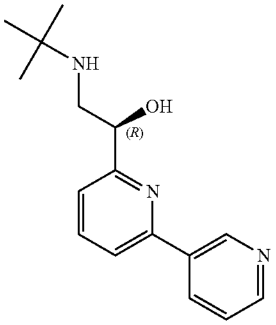 | 272.33 |

-continued
| Compound No. | Chemical Structure | MS (m/z) (M + 1) |
|---|---|---|
| 03-153 | 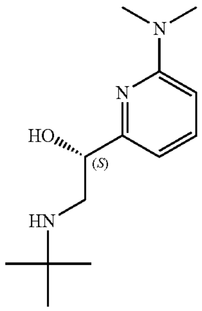 | 238.1 |
| 03-154 | 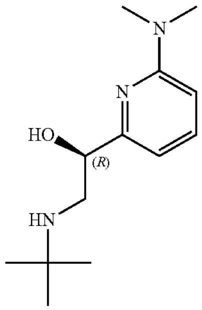 | 238.1 |
| 03-155 | 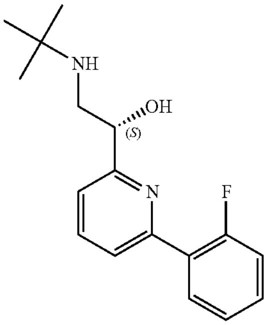 | 289.29 |
| 03-156 | 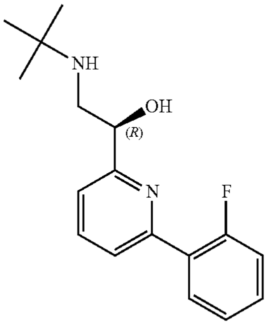 | 289.29 |

-continued
| Compound No. | Chemical Structure | MS (m/z) (M + 1) |
|---|---|---|
| 03-157 | 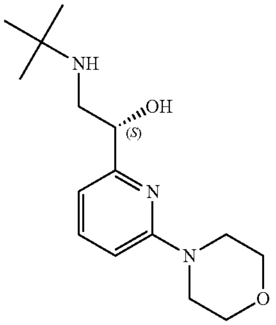 | 280.32 |
| 03-158 | 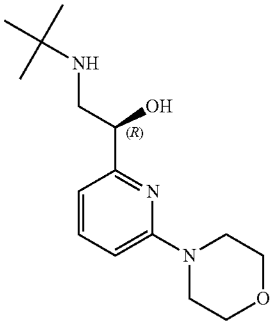 | 280.32 |
| 03-159 | 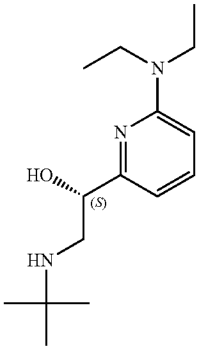 | 266.32 |
| 03-160 | 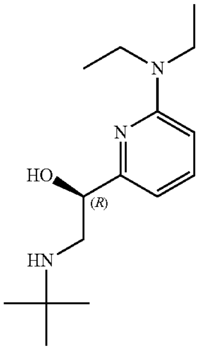 | 266.32 |

-continued
| Compound No. | Chemical Structure | MS (m/z) (M + 1) |
| --- | --- | --- |
| 03-161 | 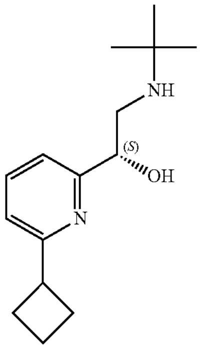 | 249.18 |
| 03-162 | 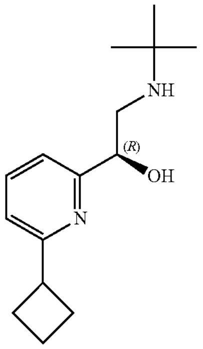 | 249.18 |
| 03-163 | 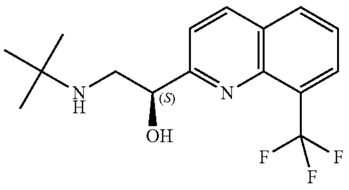 | 313.26 |
| 03-164 | 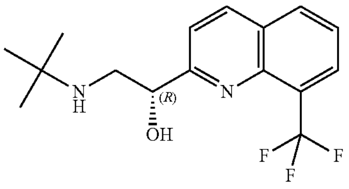 | 313.26 |
| 03-165 | 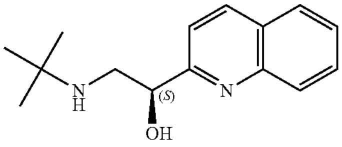 | 245.1 |
| 03-166 | 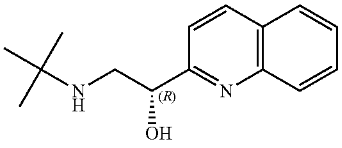 | 245.1 |

-continued
| Compound No. | Chemical Structure | MS (m/z) (M + 1) |
|---|---|---|
| 03-167 | 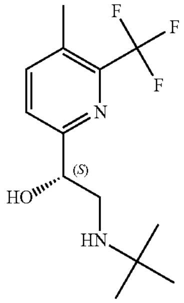 | 277.1 |
| 03-168 | 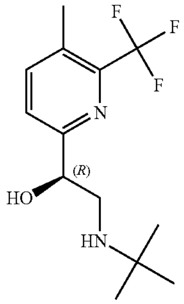 | 277.1 |
| 03-169 | 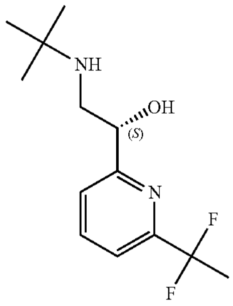 | 259.13 |
| 03-170 | 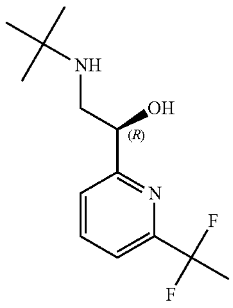 | 259.13 |
| 03-171 | 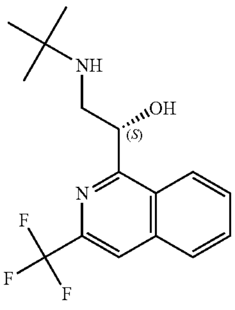 | 313.28 |

-continued
| Compound No. | Chemical Structure | MS (m/z) (M + 1) |
| --- | --- | --- |
| 03-172 | 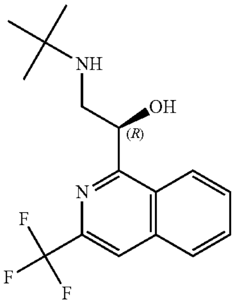 | 313.28 |
| 03-173 | 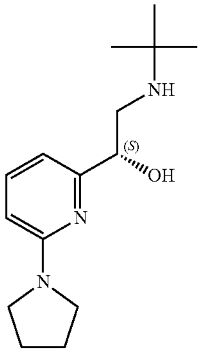 | 264.3 |
| 03-174 | 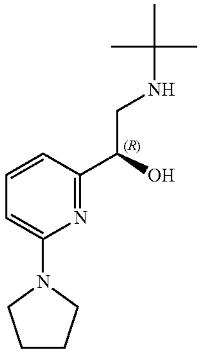 | 264.3 |
| 03-175 | 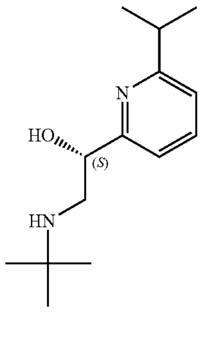 | 237.28 |

-continued
| Compound No. | Chemical Structure | MS (m/z) (M + 1) |
| --- | --- | --- |
| 03-176 | 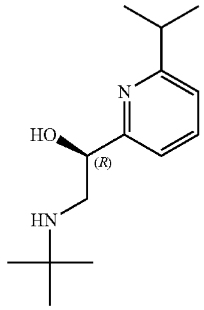 | 237.28 |
| 03-177 | 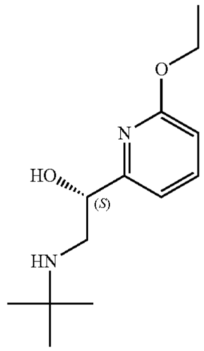 | 239.26 |
| 03-178 | 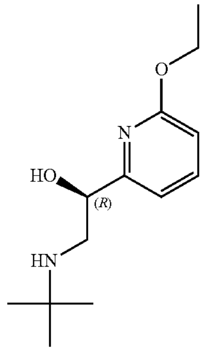 | 239.26 |
| 03-179 | 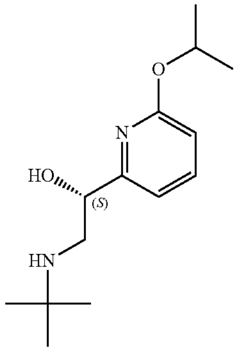 | 253.2 |

-continued
| Compound No. | Chemical Structure | MS (m/z) (M + 1) |
| --- | --- | --- |
| 03-180 | 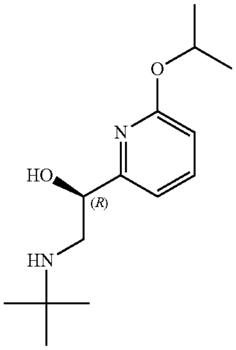 | 253.2 |
| 03-181 | 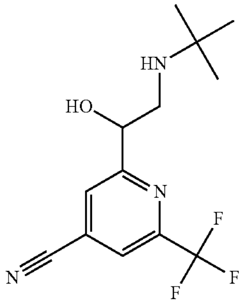 [SMILES: CC(C)(C)NCC(O)c1cc(C#N)cc(C(F)(F)F)n1] | 288.23 |
| 03-182 | 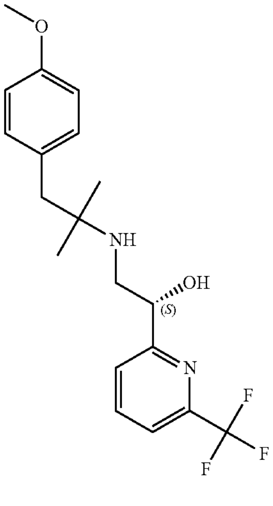 | 369.26 |

-continued
| Compound No. | Chemical Structure | MS (m/z) (M + 1) |
|---|---|---|
| 03-183 | 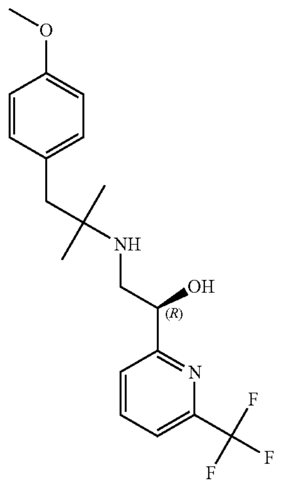 | 369.26 |
| 03-184 | 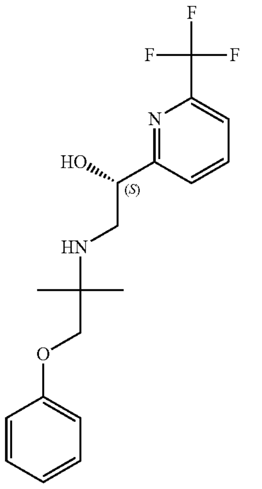 | 355.32 |
| 03-185 | 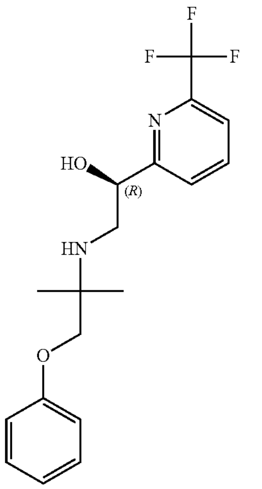 | 355.32 |

-continued
| Compound No. | Chemical Structure | MS (m/z) (M + 1) |
|---|---|---|
| 03-186 | 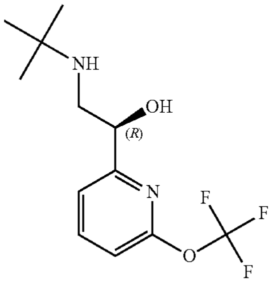 | 279.17 |
| 03-187 | 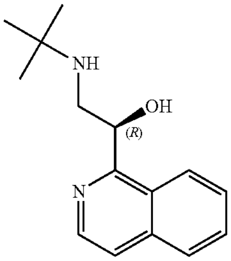 | 245.1 |
| 03-188 | 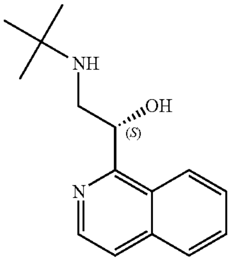 | 245.1 |
| 03-189 | 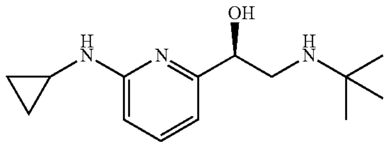 [SMILES: CC(C)(C)NC[C@H](O)c1cccc(NC2CC2)n1] | 250.2 |
| 03-190 | 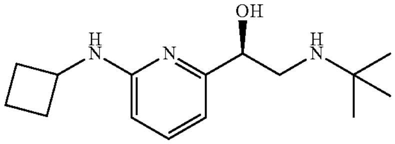 [SMILES: CC(C)(C)NC[C@H](O)c1cccc(NC2CCC2)n1] | 264.3 |
| 03-191 | 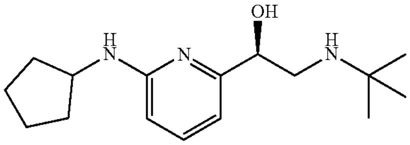 [SMILES: CC(C)(C)NC[C@H](O)c1cccc(NC2CCCC2)n1] | 278.4 |
| 03-192 | 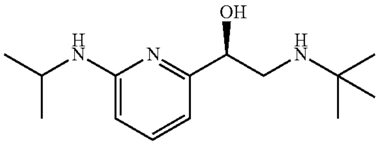 [SMILES: CC(C)Nc1cccc([C@@H](O)CNC(C)(C)C)n1] | 252.3 |
| 03-193 | 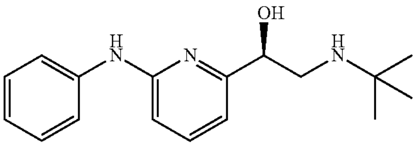 [SMILES: CC(C)(C)NC[C@H](O)c1cccc(Nc2ccccc2)n1] | 286.3 |

-continued
| Compound No. | Chemical Structure | MS (m/z) (M + 1) |
|---|---|---|
| 03-194 | 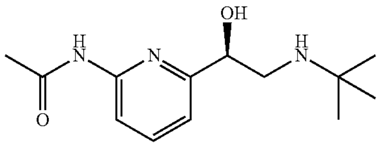 [SMILES: CC(=O)Nc1cccc([C@@H](O)CNC(C)(C)C)n1] | 252.3 |
| 03-195 | 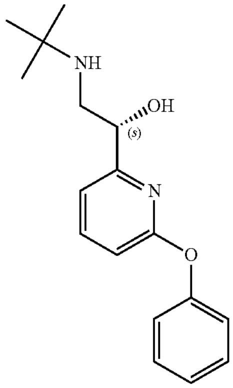 | 287.2 |
| 03-196 | 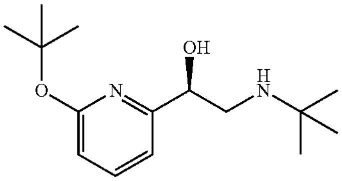 [SMILES: CC(C)(C)NC[C@H](O)c1cccc(OC(C)(C)C)n1] | 267.2 |
| 03-197 | 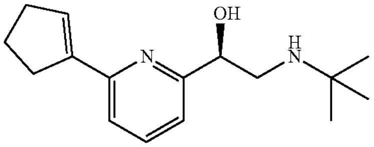 [SMILES: CC(C)(C)NC[C@H](O)c1cccc(C2=CCCC2)n1] | 261.3 |
| 03-198 | 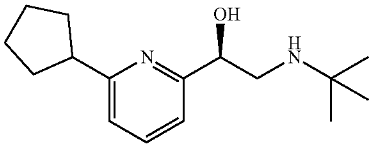 [SMILES: CC(C)(C)NC[C@H](O)c1cccc(C2CCCC2)n1] | 263.3 |
| 03-199 | 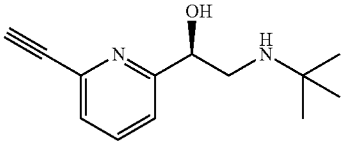 [SMILES: C#Cc1cccc([C@@H](O)CNC(C)(C)C)n1] | 219.2 |
| 03-200 | 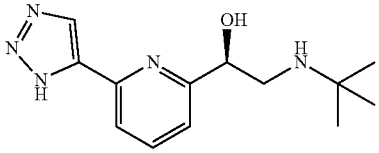 [SMILES: CC(C)(C)NC[C@H](O)c1cccc(-c2cnn[nH]2)n1] | 262.2 |
| 03-201 | 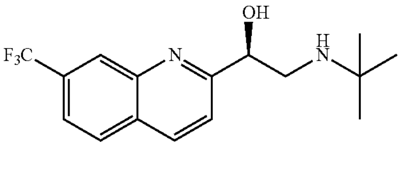 [SMILES: CC(C)(C)NC[C@H](O)c1ccc2ccc(C(F)(F)F)cc2n1] | |

-continued
| Compound No. | Chemical Structure | MS (m/z) (M + 1) |
|---|---|---|
| 03-202 | 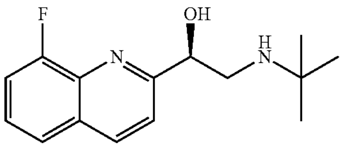 [SMILES: CC(C)(C)NC[C@H](O)c1ccc2cccc(F)c2n1] | |
| 03-203 | 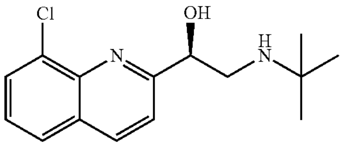 | |
| 03-204 | 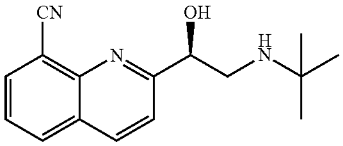 [SMILES: CC(C)(C)NC[C@H](O)c1ccc2cccc(C#N)c2n1] | |
| 03-205 | 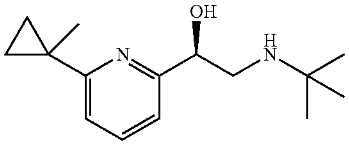 [SMILES: CC(C)(C)NC[C@H](O)c1cccc(C2(C)CC2)n1] | |
| 03-206 | 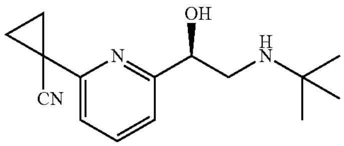 [SMILES: CC(C)(C)NC[C@H](O)c1cccc(C2(C#N)CC2)n1] | 260.4 |
| 03-207 | 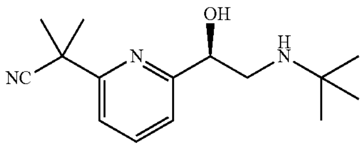 [SMILES: CC(C)(C)NC[C@H](O)c1cccc(C(C)(C)C#N)n1] | 262.3 |
| 03-208 | 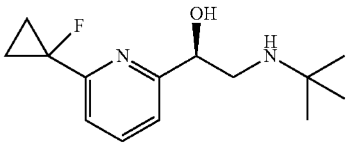 [SMILES: CC(C)(C)NC[C@H](O)c1cccc(C2(F)CC2)n1] | |
| 03-209 | 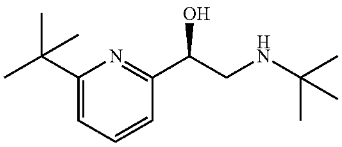 [SMILES: CC(C)(C)NC[C@H](O)c1cccc(C(C)(C)C)n1] | 251.2 |
| 03-210 | 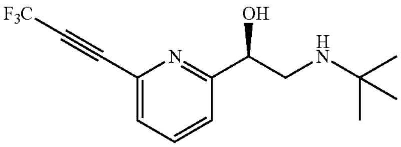 [SMILES: CC(C)(C)NC[C@H](O)c1cccc(C#CC(F)(F)F)n1] | |

-continued
| Compound No. | Chemical Structure | MS (m/z) (M + 1) |
|---|---|---|
| 03-211 | 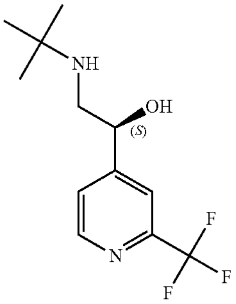 | 263.2 |
| 03-212 | 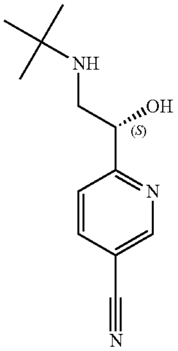 | 220.2 |
| 03-213 | 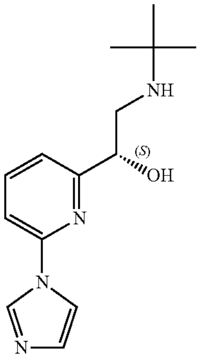 | 261.3 |
| 03-214 | 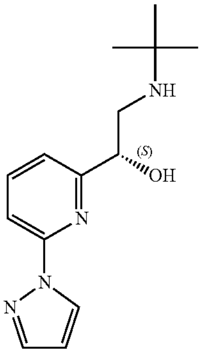 | 261.2 |

-continued
| Compound No. | Chemical Structure | MS (m/z) (M + 1) |
|---|---|---|
| 03-215 | 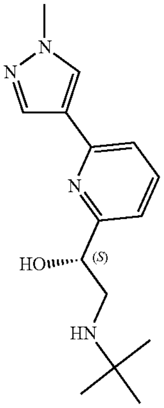 | 275.3 |
| 03-216 | 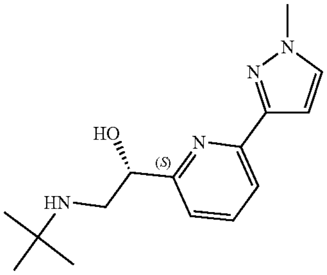 | 275.3 |
| 03-217 | 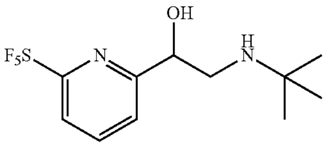 | |
| 03-218 | 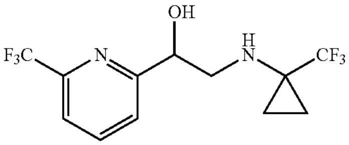 [SMILES: OC(CNC1(C(F)(F)F)CC1)c1cccc(C(F)(F)F)n1] | 315.2 |
| 03-219 | 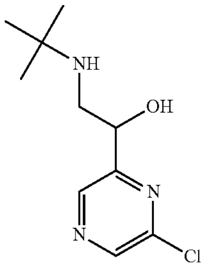 | 230.4 |

-continued
| Compound No. | Chemical Structure | MS (m/z) (M + 1) |
|---|---|---|
| 03-220 | 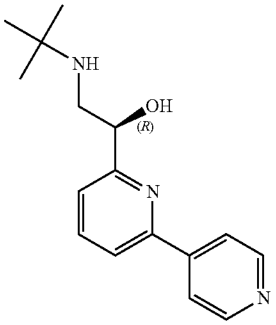 | 272.5 |
| 03-221 | 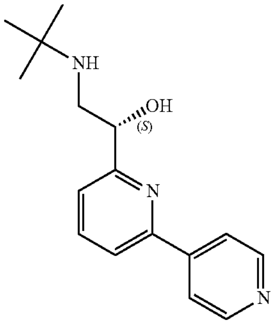 | 272.5 |
| 03-222 | 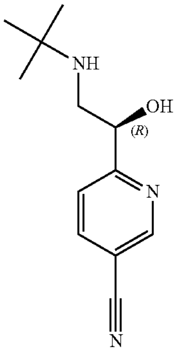 | 220.2 |
| 03-224 | 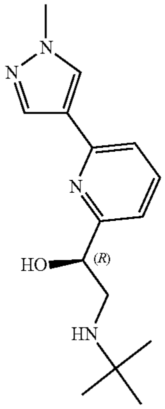 | 275.3 |

-continued
| Compound No. | Chemical Structure | MS (m/z) (M + 1) |
|---|---|---|
| 03-225 | 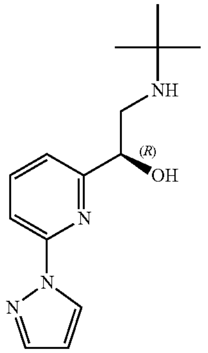 | 261.2 |
| 03-226 | 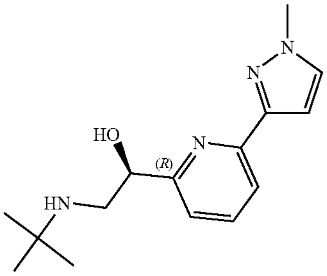 | 275.3 |
| 03-227 | 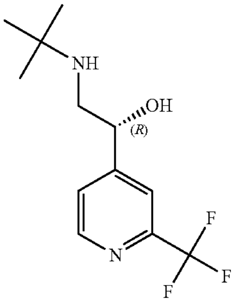 | 263.2 |
| 03-228 | 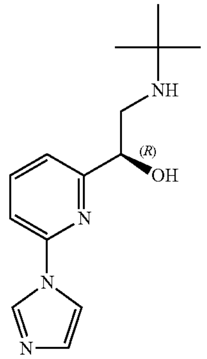 | 261.3 |

-continued
| Compound No. | Chemical Structure | MS (m/z) (M + 1) |
|---|---|---|
| 03-229 | 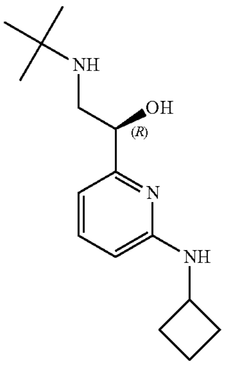 | 264.3 |
| 03-230 | 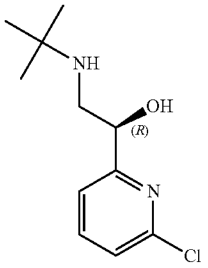 | 229.5 |
| 03-231 | 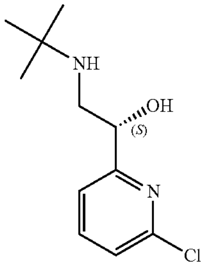 | 229.5 |
| 03-232 | 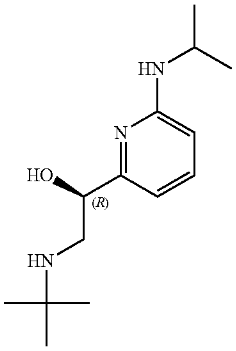 | 252.3 |

-continued
| Compound No. | Chemical Structure | MS (m/z) (M + 1) |
|---|---|---|
| 03-233 | 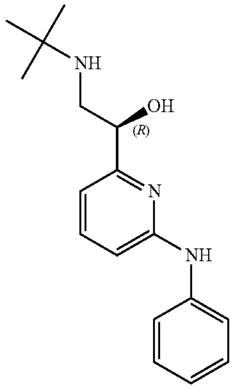 | 286.3 |
| 03-234 | 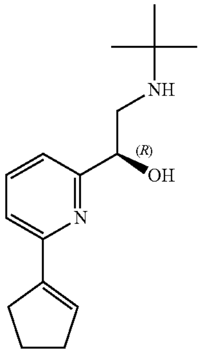 | 261.3 |
| 03-235 | 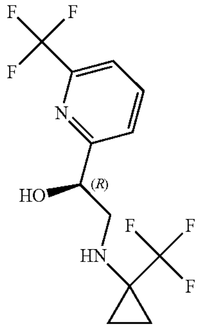 | 315.2 |
| 03-236 | 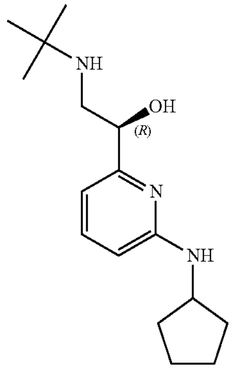 | 278.4 |

-continued
| Compound No. | Chemical Structure | MS (m/z) (M + 1) |
|---|---|---|
| 03-237 | 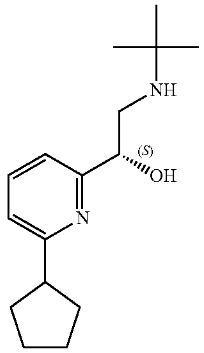 | 263.2 |
| 03-238 | 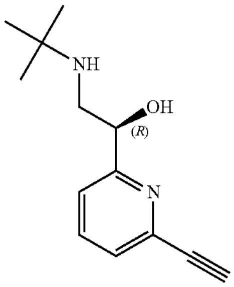 | 219.2 |
| 03-239 | 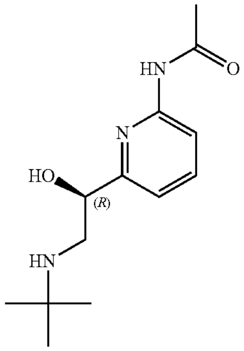 | 252.3 |
| 03-240 | 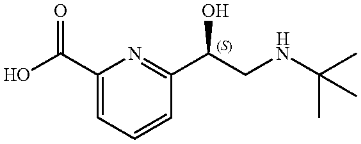 | 239.1 |
| 03-241 | 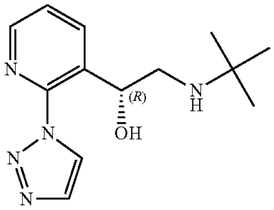 | 262.3 |

-continued
| Compound No. | Chemical Structure | MS (m/z) (M + 1) |
|---|---|---|
| 03-242 | 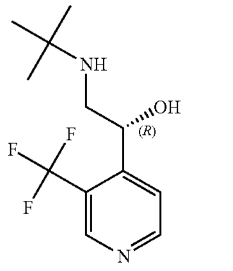 | 263.2 |
| 03-243 | 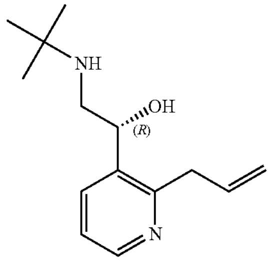 | 235.3 |
| 03-244 | 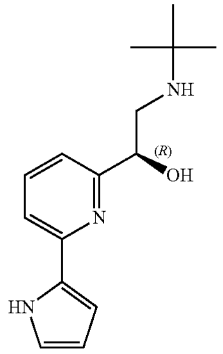 | 260.2 |
| 03-245 | 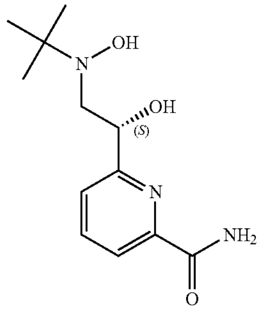 | 254.1 |
| 03-246 | 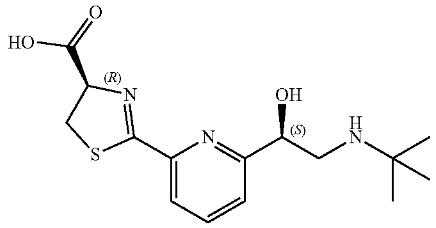 | 324.1 |

-continued
| Compound No. | Chemical Structure | MS (m/z) (M + 1) |
|---|---|---|
| 03-247 | 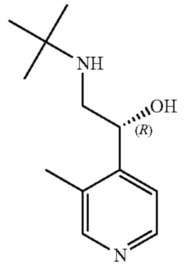 | 209.1 |
| 03-248 | 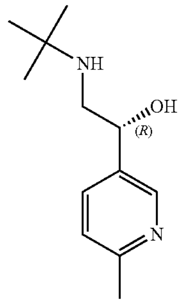 | 209.1 |
| 03-249 | 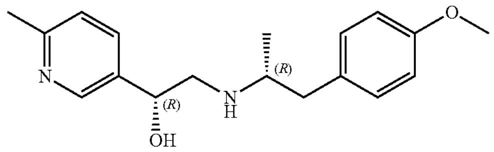 | 301.4 |
| 03-250 | 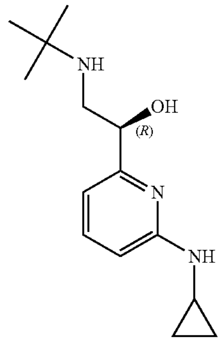 | 250.2 |
| 03-252 | 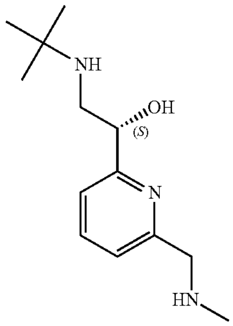 | 238.3 |
| 03-253 | 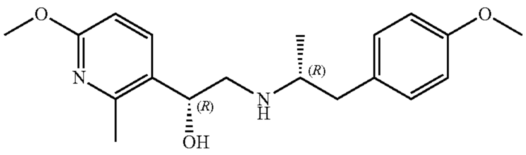 | 331.3 |

-continued
| Compound No. | Chemical Structure | MS (m/z) (M + 1) |
|---|---|---|
| 03-254 | 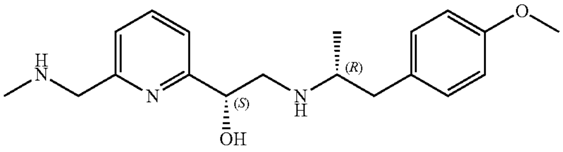 | 330.4 |
| 03-257 | 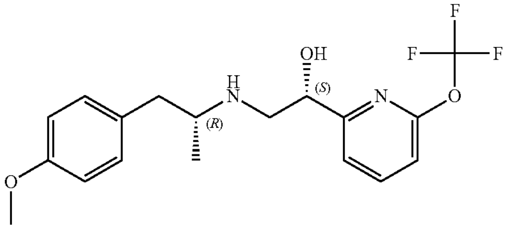 | 371.3 |
| 03-258 | 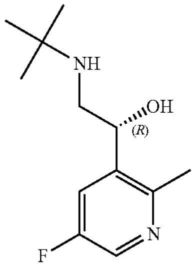 | 227.3 |
| 03-259 | 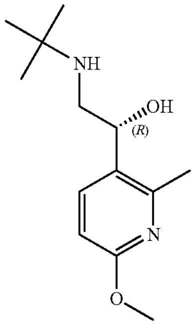 | 239.2 |
| 03-260 | 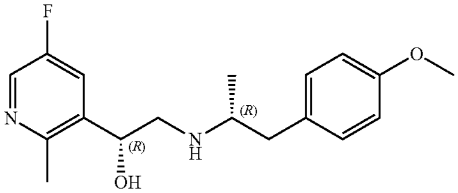 | 319.4 |
| 03-261 | 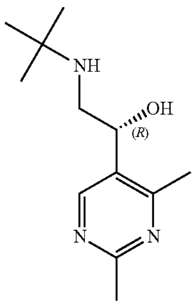 | 224.3 |

-continued
| Compound No. | Chemical Structure | MS (m/z) (M + 1) |
|---|---|---|
| 03-262 | 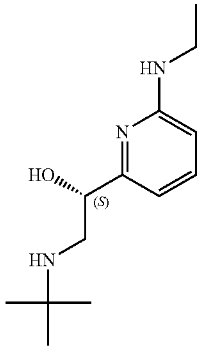 | 238.3 |
| 03-263 | 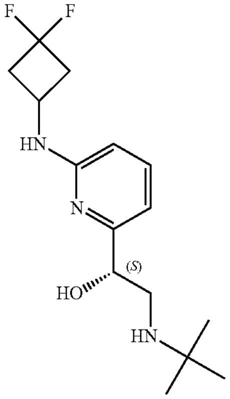 | 300.3 |
| 03-264 | 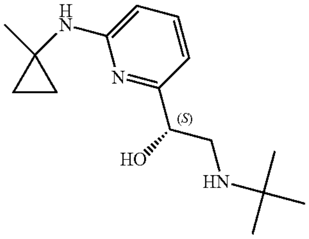 | 264.3 |
| 03-265 | 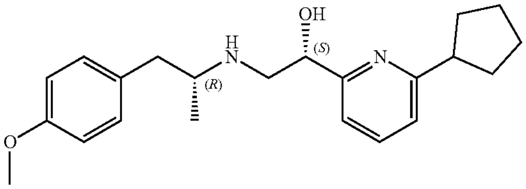 | 355.5 |
| 03-266 | 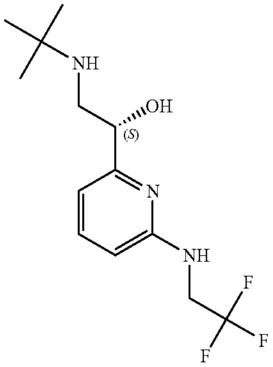 | 292.3 |

-continued
| Compound No. | Chemical Structure | MS (m/z) (M + 1) |
|---|---|---|
| 03-267 | 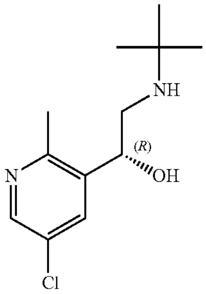 | 243.6 |
| 03-268 | 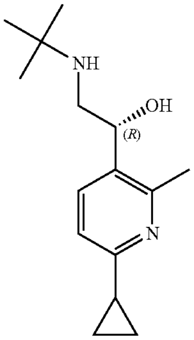 | 249.3 |
| 03-269 | 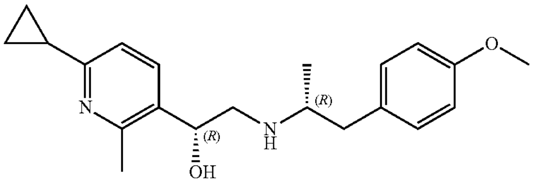 | 341.5 |
| 03-270 | 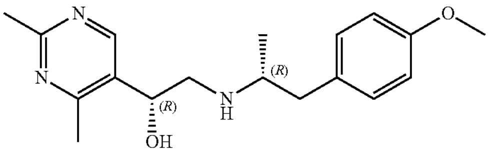 | 316.4 |
| 03-271 | 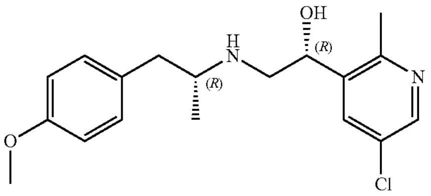 | 335.8 |

-continued
| Compound No. | Chemical Structure | MS (m/z) (M + 1) |
|---|---|---|
| 03-272 | 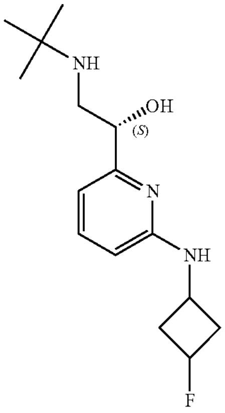 | 282.2 |
| 03-273 | 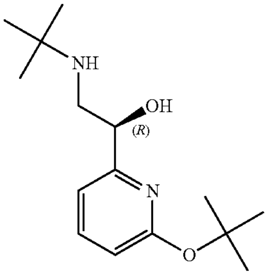 | 267.2 |
| 03-274 | 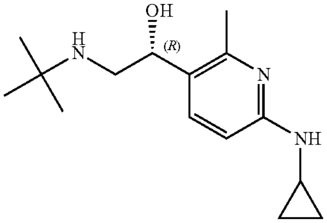 | 264.3 |
| 03-275 | 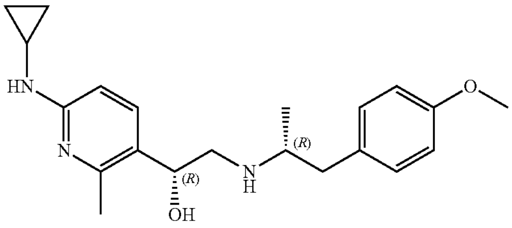 | 356.4 |
| 03-276 | 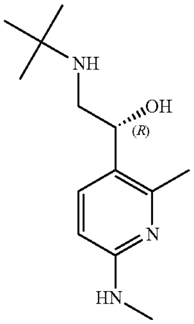 | 238.3 |

-continued
| Compound No. | Chemical Structure | MS (m/z) (M + 1) |
|---|---|---|
| 03-277 | 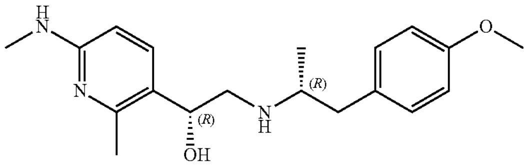 | 330.4 |
| 03-278 | 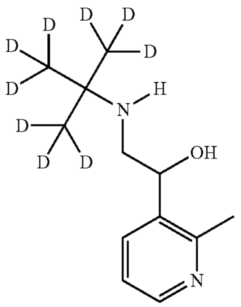 [SMILES: [2H]C([2H])([2H])C(NCC(O)c1cccnc1C)(C([2H])([2H])[2H])C([2H])([2H])[2H]] | 218.3 |
| 03-279 | 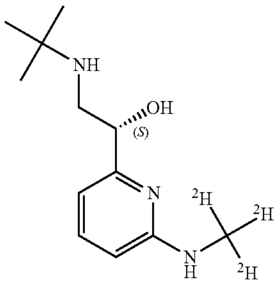 | 227.2 |
| 03-280 | 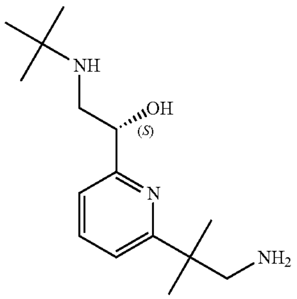 | 266.3 |
| 03-281 | 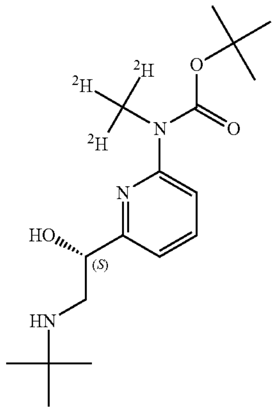 | 327.3 |
In some embodiments, a β-agent is an optically pure stereoisomer, pharmaceutically acceptable salt, solvate, or prodrug of a compound of Table 1.
Human Models/Tests
There are many contextual learning tests used that are acknowledged and/or accepted in the art that in various embodiments may be used in conjunction with the compositions and methods disclosed herein to assess baseline cognitive function and/or to measure or quantify improved cognitive function in human subjects. For example, the contextual learning test used may be based upon single task learning, multiple task learning or spatial contextual memory. Contextual learning test evaluations based upon spatial contextual memory may be advantageous in assessing, for example, how well an individual is able to navigate a shopping mall, his or her neighborhood or a city transit or subway system as well as assessing any improvements in the ability to execute these tasks resulting from the treatment methods described herein.

An example of a simple spatial contextual learning test is contextual cuing, where humans learn to use repeated spatial configurations to facilitate a target search. A higher order spatial contextual learning test is serial learning, where humans learn to use subtle sequence regularities to respond more quickly and accurately to a series of events. See, for example, J. H. Howard Jr., et al., Neuropsychology, Vol. 18(1), January 2004, 124-134.

In some embodiments, cognition may be evaluated using the Mini-Mental State Examination (MMSE) and/or the Montreal Cognitive Assessment (MOCA).

Arizona Cognitive Test Battery (ACTB). A testing protocol that may be used in various embodiments is the Arizona Cognitive Test Battery (ACTB). See Edgin, J., et al. J. Neurodevelop. Disord. (2010) 2: 149-164. The ACTB has been developed specifically to assess the cognitive phenotype in DS, and includes various tests with various task demands and links with brain function. In more detail, tests are included for: 1) benchmarks, such as KBIT II verbal subscale and KBIT II non-verbal subscale IQ tests, 2) hippocampal function, 3) prefrontal function, 4) cerebellar function, 5) Finger sequencing tasks, 6) NEPSY visuomotor precision and 7) simple reaction time.

In some embodiments, cognition may be evaluated using the Cambridge Neuropsychological Test Automated Battery (CANTAB) assessment (see, for example, Sahakian, et al., (1988). *Brain.* 111 (3): 695-718). Cognitive domains, such as attention, visuospatial working memory, episodic memory, speed of process and executive function can be assessed using the CANTAB Battery Test, which includes the following:

Reaction Time (RTI),

Paired Associates Learning (PAL),

Verbal Recognition Memory (VRM) Immediate Free Recall,

Rapid Visual Information Processing (RVP),

Spatial Working Memory (SWM),

Adaptive Tracking, and

VRM Delayed Free recall and Forced-Choice Recognition.

A correlation of domain/test, test description and certain primary abilities assessed in accordance with the ACTB is provided below:

| Domain/Test | Description | Primary Ability Assessed |
|---|---|---|
| 1) Benchmark KBIT-II verbal subscale KBIT-II nonverbal subscale | Points to pictures based on word or phrase Semantic or visuo-spatial pattern completion | Verbal comprehension Problem solving |
| 2) CANTAB spatial span | Touching boxes in order of changing color on screen | Immediate memory for spatial-temporal sequence |
| 3) Prefrontal Modified dots task | Press button below a cat, shifts to new rule, press across screen for a frog, etc. | Inhibitory control working memory |
| 4) CANTAB IED | Forced-choice discrimination task with change in relevant dimension | Set-shifting |
| 5) Hippocampal CANTAB paired associates | Recall for hidden abstract patterns | Spatial associative memory |
| 6) Virtual computer-generated arena | Navigation of a virtual arena(via oystick) to find a hidden target | Spatial memory |
| 7) Cerebellar Finger-sequencing task | Sequences generated by tapping a number of fingers (1, 2, 3, 4) to a lever in succession | Motor sequencing |
| 8) NEPSY visuo-motor precision | Follows two tracks with a pen | Visuo-motor tracking, hand-eye coord. |
| 9) CANTAB simple reaction time | Participants press button in response to a box presented on a screen | Motor response time and attention |

The above battery of tests in some embodiments may all be performed in order to assess all major cognitive processes balanced by the practical need for testing under time constraints. The cognitive tests herein may in certain embodiments be used in patients receiving treatment herein to monitor the patient's cognitive status and progression.

In some embodiments, the battery of tests may be conducted with a test group of individuals, and a control group individuals to demonstrate the effectiveness of various aspects and embodiments of the compositions and methods described herein. The test group may be treated with any of the treatment regimens described herein, and the control group is treated with placebo, such as a dextrose 5% saline solution by intranasal administration.

An improvement in cognitive function as defined herein as being at least a 10%, and preferably at least a 20% score improvement, on at least one, and preferably two or more, of the tests listed in the ATCB, for example. Anyone of the domain/tests listed for the ATCB above may be included in assessing whether an improvement occurred. Testing may be conducted after treatment or during treatment to ascertain whether modifications in dosage or frequency of treatment is warranted.

Brain Imaging. Generally, any non-invasive procedure many be used to both establish a baseline of brain pathology (existent or non-existent) from which baseline a treatment protocol is established. However, magnetic resonance imaging (MRI) may in some embodiments be preferred for neuroimaging examination because it allows for accurate measurement of the 3-dimensional (3D) volume of brain structures, especially the hippocampus and related regions. Such techniques are well known as described in U.S. Pat. No. 6,490,472, which patent is incorporated herein in the entirety.

Moreover, non-invasive optical imaging systems may also be used for monitoring neurological pathological events. See, for example, U.S. patent publication 2011/0286932, which is incorporated herein in the entirety. The technique described therein entails administration of a fluorescent marker to a human for staining Aβ peptides, imaging the retina of the DS human with an optical imaging system, and examining the images for stained Aβ peptides in order to determine whether onset of brain pathology (such as AD brain pathology) has occurred.

In certain embodiments, fluorodeoxyglucose positron emission tomography (FDG-PET) may be used for neuroimaging to determine cognitive function and/or identify a neurodegenerative disease in accordance with the compositions and methods described herein. The use of FDG-PET for monitoring cognitive function and/or diagnosing cognitive impairments or neurodegenerative diseases, and/or identifying patients in need of or desiring a treatment to improve cognitive function is described in, for example Brown et al., RadioGraphics, (2014) 34:684-701, and Shivamurthy et al., AJR, (2015) 204:W76-W85; both hereby incorporated by reference in their entirety. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

Alzheimer's Disease

AD brain pathology refers to the accumulation of highly degradation-resistant amyloid fibers that cause lesions in areas of the brain proximate thereto. Accumulation of these amyloid fibers to neurotoxic levels leads to destruction of nerve fibers, which, in turn, leads to the observed behavior associated with Alzheimer's dementia. Observed behavioral symptoms, which become progressively more severe with progression of the disease, often include loss of vocabulary, incorrect word substitutions (paraphasias), loss of reading and writing skills, increased risk of falling, wandering, loss of speech, apathy and even loss of muscle mass.

Down Syndrome

Creation of several trisomic mouse models has greatly facilitated progress in the understanding the neurobiological basis of cognitive dysfunction in DS. Among the mouse models, the Ts65Dn mouse is best characterized. It has an extra copy of approximately 140 mouse genes on chromosome 16, orthologous to those on human chromosome 21 (HSA21). Almost all genes in HSA21 with potential role in nervous system abnormalities are also found in Ts65Dn mice. Similar to DS, alterations in the structure and function of the hippocampus and failure in the induction of long-term potentiation (LTP) have been extensively reported in Ts65Dn mice. Ts65Dn mice are the most widely used in DS research, and are considered to be an art-accepted model for investigations regarding DS in humans. Olson, L. E., et al., Dev. Dyn. 2004 July; 230(3):581-9.

DS is characterized by degeneration and dysfunction of multiple neuronal populations in the central nervous system (CNS). Among them, the hippocampal formation, i.e. the primary site for processing contextual learning shows significant abnormalities in DS. As a result, failure in contextual learning is a common finding in people with DS. To uncover the neurobiological basis of failed contextual learning in DS, the integrity of subcortical regions extensively projecting to the hippocampal formation have been examined. Through extensive innervation, these subcortical regions impose strong modulatory influence on hippocampal neurons. Among these subcortical regions, LC is of particular importance. LC neurons in the brainstem are the sole supplier of massive norepinephrine (NE)-ergic terminals for the hippocampus and play a significant role in wakefulness, attention, and navigational memory. Significant age-related degeneration of NE-ergic neurons of LC in Ts65Dn mice was found. Interestingly, the loss of LC terminals in Ts65Dn mice leads to further deterioration of cognitive dysfunction in these mice. Similarly, LC neurons undergo extensive age-dependent degeneration in DS. The critical role of NE-ergic system dysfunction in cognitive dysfunction in Ts65Dn has been supported by the fact that increasing brain NE levels with L-threo-3, 4-dihydroxyphenylserine (L-DOPS), i.e. a NE prodrug, restored contextual learning in Ts65Dn mice. Although L-DOPS is in phase III clinical trial for the treatment of primary autonomic failure associated with Parkinson's disease, it is yet to be approved by the FDA and its long-term effects particularly in children have yet to be explored.

With respect to the agents described herein, the terms "modulate" and "modulation" refers to the upregulation (i.e., activation or stimulation) or downregulation (i.e., inhibition or suppression) of a response. A "modulator" is an agent, compound, or molecule that modulates, and may be, for example, an agonist, antagonist, activator, stimulator, suppressor, or inhibitor. The terms "inhibit", "reduce", remove as used herein refer to any inhibition, reduction, decrease, suppression, downregulation, or prevention in expression, activity or symptom and include partial or complete inhibition of activity or symptom. Partial inhibition can imply a level of expression, activity or symptom that is, for example, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the uninhibited expression, activity or symptom. The terms "eliminate" or "eradicate" indicate a complete reduction of activity or symptom.

As used herein, the term "a disorder" or "a disease" refers to any derangement or abnormality of function; a morbid physical or mental state. See Dorland's Illustrated Medical Dictionary, (W.B. Saunders Co. 27th ed. 1988).

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

In some embodiments, optically pure (S)-β agonist is used to the extent the $β_2$ agonist has a stereocenter, which is substantially free of (R)-β agonist. In some embodiments, optically pure (R)-β agonist is used, which is substantially free of (S)-β agonist. The term "pure", as used herein, refers to substances that have been separated from at least some or most of the components with which they are associated in nature or when originally generated or with which they were associated prior to purification. In general, such purification involves action of the hand of man. Pure agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity.

In some embodiments, contemplated methods may include for example, administering prodrugs of the compounds described herein, or a pharmaceutical composition thereof. The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). In some embodiments, the prodrug structures are constructed according to the disclosure in U.S. Pat. No. 9,849,134, which is incorporated by reference herein in the entirety.

For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxy)methyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl α-aminoalkylcarbonyl, where each α-aminoalkylcarbonyl group is independently selected from the naturally occurring L-amino acids, $P(O)(OH)_2$, —P(O)(O$(C_{1-6})$alkyl$)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., Molecules 2008, 13, 519 and references therein.

"Therapeutically effective amount" as used herein means the amount of a compound or composition (such as described herein) that causes at least one desirable change in a cell, population of cells, tissue, individual, patient or the like. In some embodiments a therapeutically effective amount as used herein means the amount of a compound or composition (such as described herein) that prevents or provides a clinically significant change in a disease or condition (e.g., reduce by at least about 30 percent, at least about 50 percent, or at least about 90 percent) or in one or more features of a disease or condition described herein. In some embodiments, the term "therapeutically effective amount" means an amount of a compound or composition as described herein effective or sufficient to improve cognition and/or treat a neurodegenerative disease in a patient. The term "frequency" as related thereto means the number of times a treatment is administered to a patient in order to obtain the result of improved cognition and/or treating a neurodegenerative disease in a patient.

Diagnostics and Assessment of Treatment

In various aspects, the methods of the disclosure include diagnosing or otherwise identifying whether a patient is in need of or desiring improvement of cognitive function and/or treatment of a neurodegenerative disease. As discussed herein, this may be performed in a variety of ways as discussed herein and generally known in the art. For example, a patient diagnosis may be made by brain imaging. In various embodiments, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used. Alternatively, MRI, including MRI-BOLD and MRI-ASL, may be used alone or in combination, and optionally with CT.

Along with identifying suitable patients for treatment, diagnosis allows further determinations to be made regarding various aspects of the type and mode of treatment to be administered. For example, depending on the diagnosis, determinations may be made regarding the pharmaceutical active to be administered, the dosage of such actives as well as the timing schedule of administration.

A diagnostic method utilized with the methods of the disclosure may make use of a detectable label to diagnose or otherwise identify a patient that is in need of or desiring improvement of cognitive function and/or treatment of a neurodegenerative disease. The term "label" (also referred to as "detectable label") refers to any moiety that facilitates detection and, optionally, quantification, of an entity that comprises it or to which it is attached. The label can be conjugated to or otherwise attached to a variety of entities, biological or otherwise. In general, a label may be detectable by, e.g., spectroscopic, photochemical, biochemical, immunochemical, electrical, optical, chemical or other means. In some embodiments a detectable label produces an optically detectable signal (e.g., emission and/or absorption of light), which can be detected e.g., visually or using suitable instrumentation such as a light microscope, a spectrophotometer, a fluorescence microscope, a fluorescent sample reader, a fluorescence activated cell sorter, a camera, or any device containing a photodetector. Labels that may be used in various embodiments include, e.g., organic materials (including organic small molecule fluorophores (sometimes termed "dyes"), quenchers (e.g., dark quenchers), polymers, fluorescent proteins); enzymes; inorganic materials such as metal chelates, metal particles, colloidal metal, metal and semiconductor nanocrystals (e.g., quantum dots); compounds that exhibit luminescence upon enzyme-catalyzed oxidation such as naturally occurring or synthetic luciferins (e.g., firefly luciferin or coelenterazine and structurally related compounds); haptens (e.g., biotin, dinitrophenyl, digoxigenin); radioactive atoms (e.g., radioisotopes such as $^{3}H$, $^{14}C$, $^{32}P$, $^{33}P$, $^{35}S$, $^{125}I$), stable isotopes (e.g., $^{13}C$, $^{2}H$); magnetic or paramagnetic molecules or particles, and the like. Fluorescent dyes include, e.g., acridine dyes; BODIPY, coumarins, cyanine dyes, napthalenes (e.g., dansyl chloride, dansyl amide), xanthene dyes (e.g., fluorescein, rhodamines), and derivatives of any of the foregoing. Examples of fluorescent dyes include Cy3, Cy3.5, Cy5, Cy5.5, Cy7, Alexa® Fluor dyes, DyLight® Fluor dyes, FITC, TAMRA, Oregon Green dyes, Texas Red, to name but a few. Fluorescent proteins include green fluorescent protein (GFP), blue, sapphire, yellow, red, orange, and cyan fluorescent proteins and fluorescent variants such as enhanced GFP (eGFP), mFruits such as mCherry, mTomato, mStrawberry; R-Phycoerythrin, and the like. Enzymes useful as labels include, e.g., enzymes that act on a substrate to produce a colored, fluorescent, or luminescent substance. Examples include luciferases, β-galactosidase, horseradish peroxidase, and alkaline phosphatase. Luciferases include those from various insects (e.g., fireflies, beetles) and marine organisms (e.g., cnidaria such as *Renilla* (e.g., *Renilla reniformis*, copepods such as *Gaussia* (e.g., *Gaussia princeps*) or *Metridia* (e.g., *Metridia longa, Metridia pacifica*), and modified versions of the naturally occurring proteins. A wide variety of systems for labeling and/or detecting labels or labeled entities are known in the art. Numerous detectable labels and methods for their use, detection, modification, and/or incorporation into or conjugation (e.g., covalent or noncovalent attachment) to biomolecules such as nucleic acids or proteins, and the like, are described in Iain Johnson, I., and Spence, M. T. Z. (Eds.), The Molecular Probes® Handbook—A Guide to Fluorescent Probes and Labeling Technologies. 11th edition (Life Technologies/Invitrogen Corp.) available online on the Life Technologies website at invitrogen.com/site/us/en/home/References/Molecular-Probes-The-Handbook.html and Hermanson, G T., Bioconjugate Techniques, $2^{nd}$ ed., Academic Press (2008). Many labels are available as derivatives that are attached to or incorporate a reactive functional group so that the label can be conveniently conjugated to a biomolecule or other entity of interest that comprises an appropriate second functional group (which second functional group may either occur naturally in the biomolecule or may be introduced during or after synthesis). For example, an active ester (e.g., a succinimidyl ester), carboxylate, isothiocyanate, or hydrazine group can be reacted with an amino group; a carbodiimide can be reacted with a carboxyl group; a maleimide, iodoacetamide, or alkyl bromide (e.g., methyl bromide) can be reacted with a thiol (sulfhydryl); an alkyne can be reacted with an azide (via a click chemistry reaction such as a copper-catalyzed or copper-free azide-alkyne cycloaddition). Thus, for example, an N-hydroxysuccinide (NHS)-functionalized derivative of a fluorophore or hapten (such as biotin) can be reacted with a primary amine such as that present in a lysine side chain in a protein or in an aminoallyl-modified nucleotide incorporated into a nucleic acid during synthesis. A label may be directly attached to an entity or may be attached to an entity via a spacer or linking group, e.g., an alkyl, alkylene, aminoallyl, aminoalkynyl, or oligo-ethylene glycol spacer or linking group, which may have a length of, e.g., between 1 and 4, 4-8, 8-12, 12-20 atoms, or more in various embodiments. A label or labeled entity may be directly detectable or indirectly detectable in various embodiments. A label or labeling moiety may be directly detectable (i.e., it does not require any further reaction or reagent to be detectable, e.g., a fluorophore is directly detectable) or it may be indirectly detectable (e.g., it is rendered detectable through reaction or binding with another entity that is detectable, e.g., a hapten is detectable by immunostaining after reaction with an appropriate antibody comprising a reporter such as a fluorophore or enzyme; an enzyme acts on a substrate to generate a directly detectable signal). A label may be used for a variety of purposes in addition to or instead of detecting a label or labeled entity. For example, a label can be used to isolate or purify a substance comprising the label or having the label attached thereto.

The term "labeled" is used herein to indicate that an entity (e.g., a molecule, such as a biological or small molecule, organic compound, probe, cell, tissue, and the like) comprises or is physically associated with (e.g., via a covalent bond or noncovalent association) a label, such that the entity can be detected. In some embodiments a detectable label is selected such that it generates a signal that can be measured and whose intensity is related to (e.g., proportional to) the amount of the label. In some embodiments two or more different labels or labeled entities are used or present in a composition. In some embodiments the labels may be selected to be distinguishable from each other. For example, they may absorb or emit light of different wavelengths. In some embodiments the labels may be selected to interact with each other. For example, a first label may be a donor molecule that transfers energy to a second label, which serves as an acceptor molecule through nonradiative dipole-coupling as in resonance energy transfer (RET), e.g., Forster resonance energy transfer (FRET, also commonly called fluorescence resonance energy transfer).

Nuclear imaging is one of the most important tools of diagnostic medicine wherein an estimated 12-14 million nuclear medicine procedures are performed each year in the United States alone. Diagnostic nuclear imaging is therefore crucial for studies which determine the cause of a medical problem based on organ function, in contrast to radiographic studies, which determine the presence of disease based on static structural appearance.

Diagnostic radiopharmaceuticals and radiotracers are often designed or selected capable of selective binding to specific receptors by means of a binding moiety, such as an antibody, a specific inhibitor or other target-specific ligand. These targeted markers can therefore concentrate more rapidly in areas of interest, such as inflamed tissues, tumors, malfunctioning organs or an organ undergoing heightened expression of certain proteins. Thus, a blood circulating radiopharmaceutical is picked up by a specific organ or pathological tissue to a different extent than by other or non-pathological tissue. For example, a highly vascularized tissue (e.g., of a growing tumor) may concentrate more of a radiopharmaceutical while an ischemic tissue may concentrate less of the radiopharmaceutical than the surrounding tissues. Nuclear imaging relies on these general phenomena of varied distribution of radiopharmaceutical according to different tissue as well as different pathologies. As a result, specific tissue types (e.g., tumor tissues) may be distinguished from other tissues in radioactive-emission imaging.

Radiopharmaceuticals, which may be used in the process of differential diagnosis of pathologies may be conjugated to targeting (recognition binding) moieties and include a wide range of radioisotopes as mentioned below. Such radiopharmaceuticals therefore include recognition moieties such as, for example, monoclonal antibodies (which bind to a highly specific pre-determined target), fibrinogen (which is converted into fibrin during blood clotting), glucose and other chemical moieties and agents. Commonly used diagnostic conjugated radiopharmaceuticals include, for example, 2-[$^{18}$F]fluoro-2-deoxy-D-glucose ($^{18}$FDG), $^{111}$In-Pentetreotide ([$^{111}$In-DTPA-D-Phe$^{1}$]-octreotide), L-3-[$^{123}$I]-Iodo-α-methyl-tyrosine (IMT), O-(2-[$^{18}$F]fluoroethyl)-L-tyrosine (L-[$^{18}$F]FET), $^{111}$In-Capromab Pendetide (CYT-356, Prostascint) and $^{111}$In-Satumomab Pendetide (Oncoscint).

Two basic techniques are widely used for nuclear imaging: positron emission tomography (PET) and single photon emission computed tomography (SPECT). PET detects photons generated through positron-electron annihilation of positrons from a diagnostic radiopharmaceutical tracer placed in the subject, e.g., patient, to be imaged, and analyzes the photon energy and trajectory to generate tomographic images of the patient. SPECT generates images by computer analysis of photon emission events from a diagnostic radiopharmaceutical tracer having gamma emitting isotopes. Both PET and SPECT require the detection and analysis of single photon events, which are characterized by low signal to noise ratio and scarcity relative to the background radiation. Other constraints on the PET and SPECT image qualities include the sensitivity, temporal and spatial resolution, dynamic range, response time and counting rate characteristics of the data acquisition probe devices, e.g., photomultipliers and the like.

Radioisotopes that emit both high energy γ and/or low energy γ, β and/or positron radiation and which can be used per se or as a part of a compound as radiopharmaceuticals, include, without limitation, technetium-99m ($^{99m}$Tc), gallium-67 ($^{67}$Ga), thallium-201 ($^{201}$Tl), 111indium-($^{111}$In), iodine-123 ($^{123}$I), iodine-125 ($^{125}$I), iodine-131 ($^{131}$I), xenon-133 ($^{133}$Xe), and fluorine-18 ($^{18}$F). All these isotopes, except $^{99m}$Tc, $^{131}$I and $^{133}$Xe, are produced in particle accelerators.

Non-limiting examples of commonly used radiotracers include $^{99m}$Tc-Arcitumomab (CEA-Scan™) which is a monoclonal antibody for imaging colorectal tissues afflicted with colorectal cancer, $^{99m}$Tc-sestamibi (Cardiolite™) and $^{99m}$Tc-tetrofosmin (Myoview™) for imaging the heart of a subject for myocardial perfusion, $^{111}$In-Capromab pendetide (ProstaScint™) which is a monoclonal antibody for imaging prostate tissues afflicted with prostate cancer, $^{99m}$Tc-Fanolesomab (NeutroSpec™) which is a monoclonal antibody for imaging inflamed and infectious tissues and $^{90}$Y/111In-Zevalin (Ibritumomab Tiuxetan) which is a monoclonal antibody directed against the CD20 antigen, whereby this antigen is found on the surface of normal and malignant B lymphocytes.

Any diagnostic radiopharmaceutical can be utilized in the kit of the present embodiments. Exemplary radiopharmaceuticals that can be utilized in this context of the present invention include, without limitation, $^{3}$H-water, $^{3}$H-inulin, $^{11}$C-carbonmonoxide, $^{13}$N-ammonia, $^{14}$C-inulin, $^{15}$O—$H_2$O, $^{15}$O—$O_2$, $^{18}$F-fluorodeoxyglucose, $^{18}$F-sodium fluoride, $^{51}$Cr-erythrocytes (RBC), $^{57}$Co-vitamin B12 (cyanocobalamin), $^{58}$Co-vitamin B12 (cyanocobalamin), $^{59}$Fe-citrate, $^{60}$Co-vitamin B12 (cyanocobalamin), $^{67}$Ga-citrate, $^{68}$Ga-citrate, $^{75}$Se-selenomethionine, $^{81m}$Kr-krypton for inhalation, oral administration or injections, $^{82}$Rb, $^{85}$Sr-nitrate, $^{90}$Y/$^{111}$In-ibritumomab tiuxetan ($^{90}$Y/$^{111}$In-Zevalin), $^{99m}$Tc-albumin microspheres, $^{99m}$ Tc-disofenin, lidofenin and mebrofenin, $^{99}$mTc-DMSA, $^{99m}$Tc-DTPA (injection), $^{99m}$Tc-DTPA (aerosol), $^{99m}$Tc-ECD (ethylene cystate dimer), $^{99m}$Tc-exametazime (HMPAO), $^{99m}$Tc-glucoheptonate, $^{99m}$Tc-HEDP, $^{99m}$Tc-HMDP, $^{99m}$Tc-HSA, $^{99m}$Tc-MAA, $^{99m}$Tc-MAG.sub.3 $^{99m}$Tc-MDP, $^{99m}$Tc-tetrofosmin (Myoview), $^{99m}$Tc-sestamibi (Cardiolite), $^{99m}$Tc-oral administrations, $^{99m}$Tc-pertechnetate, $^{99m}$Tc-pyrophosphate, $^{99m}$Tc—RBC in vitro and in vivo labeling, $^{99m}$Tc-sulfur colloid, $^{99m}$Tc-teboroxime, $^{99m}$Tc-white blood cells, $^{111}$In-ibritumomab tiuxetan ($^{111}$In-Zevalin), $^{111}$In-DTPA, $^{111}$In-platelets, $^{111}$In—RBC, $^{111}$In-white blood cells, $^{123}$I-hippuran, $^{123}$I-IMP, $^{123}$I-mIBG, $^{123}$I-sodium iodide, $^{124}$I-sodium iodide, $^{125}$I-fibrinogen, $^{125}$I-IMP, $^{125}$I-mIBG, $^{125}$I-sodium iodide, $^{126}$I-sodium iodide, $^{130}$I-sodium iodide, $^{131}$I-hippuran, $^{131}$I-HSA, $^{131}$-MAA, $^{131}$I-mIBG, $^{131}$I-Rose Bengal, $^{131}$I-sodium iodide, $^{127}$Xe-inhalation and injection, $^{133}$Xe-inhalation and injection, $^{197}$Hg-chlormerodrin, $^{198}$Au-colloid and $^{201}$Tl-chloride.

The diagnostic methods described herein may also but utilized to assess the effectiveness of a particular therapeutic regimen. For example, a patient that has been identified as being in need of or desiring improvement of cognitive function and/or treatment of a neurodegenerative disease and which is being treated, may be diagnosed or otherwise assessed to determine the effectiveness of the treatment regime. While the diagnosis or assessment may be performed by any method known in the art, cognitive testing or brain imaging may be used to determine improvement of cognitive function or amelioration of a disease. In embodiments, cognitive testing or brain imaging may be used alone or in combination. In embodiments where brain imaging is utilized, FDG-PET may be used alone or in combination with CT and/or MRI including MRI-ASL and/or MRI-BOLD. For example, FDG-PET and MRI-BOLD may be used, or FDG-PET and MRI-ASL may be used. Alternatively, FDG-PET, MRI-BOLD and MRI-ASL may be used.

Alternatively, MRI, including MRI-BOLD and MRI-ASL, may be used alone or in combination, and optionally with CT.

The assessment of treatment efficacy may be utilized to alter the treatment regime of a patient. For example, the assessment may be utilized to alter dosing, timing of administration, and/or the actives of the pharmaceutical composition. In embodiments, the dosage of a particular pharmaceutical agent being administered to the patient may be lowered by combining administration with a different agent. In this manner, treatment may be optimized by altering the pharmaceutical composition to include different combinations of β-agent, $\beta_1$-AR agonist, $\beta_2$-AR agonist, and peripherally acting β-blocker (PABRA). Dosing may also be altered depending on the timing of administration. For example, a shorter duration between each administration of the pharmaceutical composition may require a lower dose of active agent, while a longer duration between each administration of the pharmaceutical composition may require a higher dose of active agent, either of which may improve the treatment regime as determined by diagnosis or assessment of the patient.

In one embodiment, a patient may be assessed a single time during the course of treatment to optimize the treatment regime. Alternatively, the patient may be assessed multiple times over the course of treatment to continually optimize the treatment regime as directed by a medical professional.

Dosage, Administration and Pharmaceutical Formulation

The term "pharmaceutically-accepted salts" means acid addition salts that are commonly used in human or veterinary medicine and are deemed safe for use. Examples for the present disclosure include, but are not limited to, salts obtained from the following acids: acetic, ascorbic, benzenesulfonic, benzoic, camphosulfonic, citric, ethanesulfonic, edisylic, fumaric, gentisic, gluconic, glucoronic, glutamic, hippuric, hydrobromic, isethionic, lactic, nitric, phosphoric, succinic, sulfuric and tartaric, for example. Any hydrated forms of such salts are also included in this definition. Thus, for example, both fumarate and hemifumarate salts are specifically contemplated as well as any hydrates thereof. For example, fumarate dihydrate may be specifically mentioned.

The pharmaceutical preparation in some embodiments may be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. Preferably, the unit dosage form is a tablet. The composition can, if desired, also contain other compatible therapeutic agents. Preferred pharmaceutical preparations can deliver the compounds of the disclosure in a sustained release formulation.

For a binding agent, composition, or compound according to the present disclosure, the dosage form may optionally be a liquid dosage form. Solutions can be prepared in water suitably mixed with a surfactant such as hydroxypropylcellulose or an emulsifier such as polysorbate. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. Formulations optionally contain excipients including, but not limited to, a buffering agents, an anti-oxidant, a stabilizer, a carrier, a diluent, and an agent for pH adjustment. The pharmaceutical forms suitable for injectable use include sterile aqueous solutions or dispersion and sterile powders for the extemporaneous preparation of sterile injectable solutions or dispersions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

In various embodiments, the dose of an agent may be determined by the human patient's body weight. For example, an absolute dose of an agent of about 30 to 160 μg for a pediatric human patient of about 0 to about 5 kg (e.g. about 0, or about 1, or about 2, or about 3, or about 4, or about 5 kg); or about 30 to 160 μg for a pediatric human patient of about 6 to about 8 kg (e.g. about 6, or about 7, or about 8 kg), or about 30 to 160 μg for a pediatric human patient of about 9 to about 13 kg (e.g. 9, or about 10, or about 11, or about 12, or about 13 kg); or about 30 to 160 μg for a pediatric human patient of about 14 to about 20 kg (e.g. about 14, or about 16, or about 18, or about 20 kg), or about 30 to 160 μg for a pediatric human patient of about 21 to about 30 kg (e.g. about 21, or about 23, or about 25, or about 27, or about 30 kg), or about 30 to 160 μg for a pediatric human patient of about 31 to about 33 kg (e.g. about 31, or about 32, or about 33 kg), or about 30 to 160 μg for an adult human patient of about 34 to about 50 kg (e.g. about 34, or about 36, or about 38, or about 40, or about 42, or about 44, or about 46, or about 48, or about 50 kg), or 30 to 160 μg for an adult human patient of about 51 to about 75 kg (e.g. about 51, or about 55, or about 60, or about 65, or about 70, or about 75 kg), or about 30 to 160 μg for an adult human patient of greater than about 114 kg (e.g. about 114, or about 120, or about 130, or about 140, or about 150 kg).

In certain embodiments, an agent in accordance with the methods provided herein is administered orally, subcutaneously (s.c.), intravenously (i.v.), intramuscularly (i.m.), intranasally or topically. Administration of an agent described herein can, independently, be one to four times daily; or one or two times weekly; or one to four times per month; or one to six times per year or once every two, three, four or five years. Administration can be for the duration of one day or one month, two months, three months, six months, one year, two years, three years, and may even be for the life of the human patient. The dosage may be administered as a single dose or divided into multiple doses.

In some embodiments, an agent is administered about 1 to about 3 times (e.g. 1, or 2 or 3 times).

The compounds of this disclosure may be prepared or isolated in general by synthetic and/or semi-synthetic methods known to those skilled in the art for analogous compounds and by methods described in detail in the Examples, herein. In one embodiment, the compounds selected from those compounds set forth in Table 1 were prepared by the methods illustrated in Scheme A.

Scheme A.

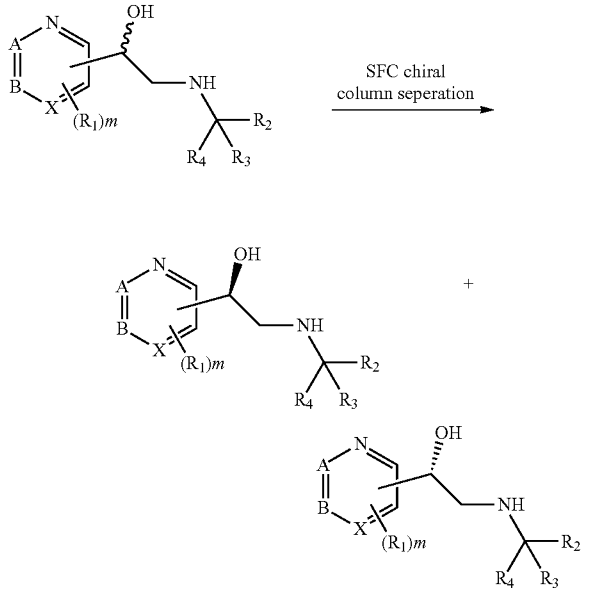

In one embodiment, the compounds selected from those compounds set forth in Table 1 were prepared by the methods illustrated in Scheme B.

Scheme B.

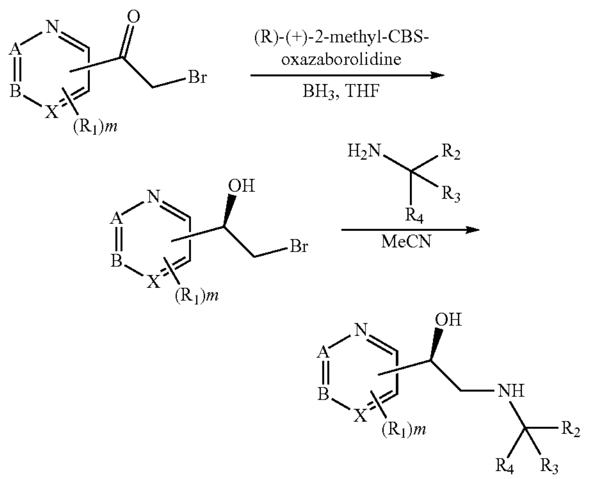

In one embodiment, the compounds selected from those compounds set forth in Table 1 were prepared by the methods illustrated in Scheme C.

Scheme C.

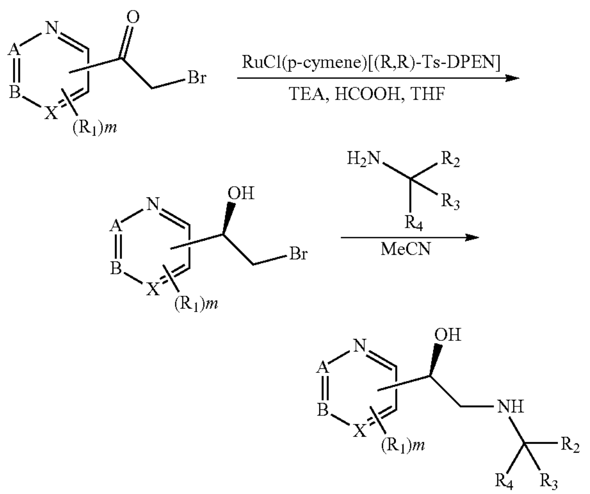

In one embodiment, the compounds selected from those compounds set forth in Table 1 were prepared by the methods illustrated in Scheme D.

Scheme D.

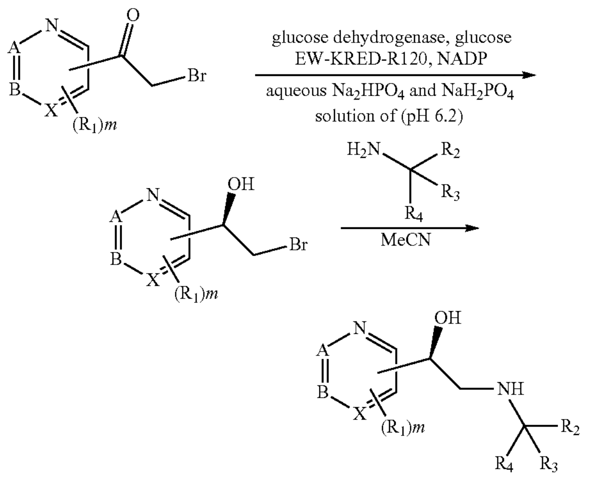

In one embodiment, the compounds selected from those compounds set forth in Table 1 were prepared by the methods illustrated in Scheme E.

Scheme E.

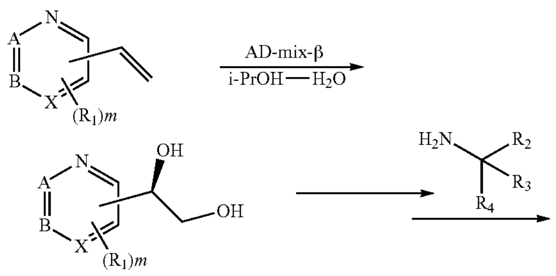

-continued

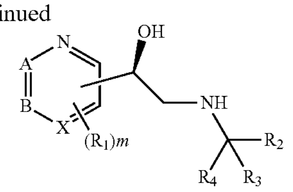

In one embodiment, the compounds selected from those compounds set forth in Table 1 were prepared by the methods illustrated in Scheme F.

Scheme F.

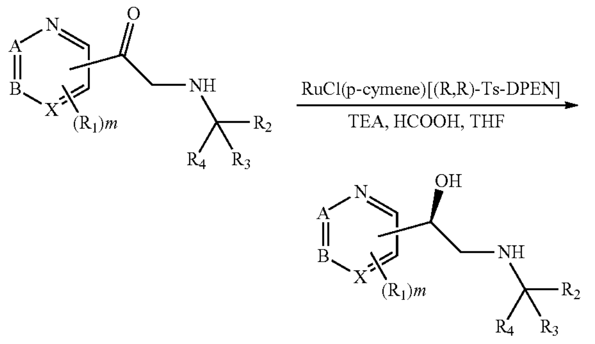

In one embodiment, the compounds selected from those compounds set forth in Table 1 were prepared by the methods illustrated in Scheme G.

Scheme G.

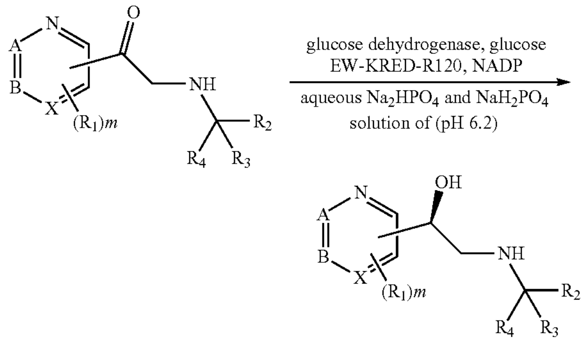

Specific Embodiments

In addition to the aspects and embodiments disclosed elsewhere herein, the following are specifically contemplated:

1. A method comprising:
   administering to a patient a β-agent and a peripherally acting β-blocker (PABRA), wherein the peripherally acting β-blocker (PABRA) is administered in a sub-therapeutic dose.
2. A method, comprising:
   administering to a patient a β-agent and a peripherally acting β-blocker (PABRA) to improve cognition and/or treat a neurodegenerative disease in said patient, wherein the peripherally acting β-blocker ((PABRA) is administered in a sub-therapeutic dose.

3. The method of any of the preceding embodiments, further comprising:
   subjecting said patient to brain imaging to determine cognitive function and/or to identify whether said patient is in need of or desiring improvement of cognitive function and/or treatment of a neurodegenerative disease.
4. The method of any of the preceding embodiments, further comprising:
   identifying a particular type of neurodegenerative disease based on a spatial pattern of the brain imaging result.
5. The method of any of the preceding embodiments, further comprising:
   subsequently re-subjecting said patient to brain imaging to determine any improvement in cognitive function and/or treatment of said neurodegenerative disease.
6. The method of any of the preceding embodiments, wherein the brain imaging is fluorodeoxyglucose positron emission tomography (FDG-PET) scan, magnetic resonance imaging-arterial spin labeling (MRI-ASL), or magnetic resonance imaging-blood oxygenation level dependent computerized tomography (MRI-BOLD).
7. The method of any of the preceding embodiments, wherein said β-agent is administered at a dose of from about 30 to 160 μg.
8. The method of any of the preceding embodiments, wherein said β-agent is administered at a dose of from about 50 to 160 μg.
9. The method of any of the preceding embodiments, wherein said dose of said β-agent is a total daily dose and is administered daily for a period of weeks or more.
10. The method of any of the preceding embodiments, wherein said β-agent is administered at a dose of from about 0.1 to 30 mg.
11. The method of any of the preceding embodiments, wherein said β-agent is administered at a dose of from about 30 to 200 mg.
12. The method of any of the preceding embodiments, wherein the peripherally acting (3-blocker (PABRA) is administered in a dose of about 0.1 to 30 mg.
13. The method of any of the preceding embodiments, wherein the peripherally acting (3-blocker (PABRA) is administered in a dose of about 5 to 10 mg.
14. The method of any of the preceding embodiments, wherein said dose of the peripherally acting β-blocker (PABRA) is a total daily dose and is administered daily for a period of weeks or more.
15. The method of any of the preceding embodiments, wherein the peripherally acting (3-blocker (PABRA) is one or more selected from the group consisting of nadolol, atenolol, sotalol and labetalol.
16. The method of any of the preceding embodiments, wherein the peripherally acting (3-blocker (PABRA) is nadolol.
17. The method according to any of the preceding embodiments, wherein nadolol is a mixture of four diastereomers.
18. The method according to any of the preceding embodiments, wherein the nadolol administered is a specific enantiomerically pure isomer.
19. The method of any of the preceding embodiments, wherein the peripherally acting (3-blocker (PABRA) is atenolol.

20. The method of any of the preceding embodiments wherein the β-agent and peripherally acting β-blocker (PABRA) are each administered orally.
21. The method of any of the preceding embodiments, wherein the β-agent is administered at a dose of from about 30 to 160 μg.
22. The method of any of the preceding embodiments, wherein the β-agent is administered at a dose of from about 50 to 160 μg.
23. The method of any of the preceding embodiments, wherein said β-agent is administered at a dose of from about 0.1 to 30 mg.
24. The method of any of the preceding embodiments, wherein said β-agent is administered at a dose of from about 30 to 200 mg.
25. The method of any of the preceding embodiments, wherein said dose of said β-agent is a total daily dose and is administered daily for a period of weeks or more.
26. The method of any of the preceding embodiments, wherein said dose of said β-agent is a weekly dose and is administered weekly for a period of two weeks or more.
27. The method of any of the preceding embodiments, wherein the peripherally acting j-blocker (PABRA) is administered in a dose of about 0.1 to 15 mg.
28. The method of any of the preceding embodiments, wherein the peripherally acting 3-blocker (PABRA) is administered in a dose of about 5 to 10 mg.
29. The method of any of the preceding embodiments, wherein said dose of the peripherally acting β-blocker (PABRA) is a total daily dose and is administered daily for a period of weeks or more.
30. The method of any of the preceding embodiments, wherein said dose of the peripherally acting β-blocker (PABRA) is a weekly dose and is administered weekly for a period of two weeks or more.
31. The method of any of the preceding embodiments wherein the neurodegenerative disease is one or more selected from the group consisting of MCI, aMCI, Vascular Dementia, Mild Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), Parkinson's disease associated with REM sleep behavior disorder (RBD+PD) and/or positive response to RBD Single-Question Screen (RBD1Q) and without hallucinations, MCI or mild dementia due to Parkinson's disease associated with REM sleep behavior disorder (RBD+PD) and/or positive response to RBD Single-Question Screen (RBD1Q) and without hallucinations, ADHD (attention deficit hyperactivity disorder), and Down Syndrome.
32. The method of any of the preceding embodiments wherein the neurodegenerative disease is one or more selected from the group consisting of MCI, aMCI, Vascular Dementia, mild Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), Parkinson's disease associated with REM sleep behavior disorder (RBD+PD) and/or positive response to RBD Single-Question Screen (RBD1Q) and without hallucinations, MCI or mild dementia due to Parkinson's disease associated with REM sleep behavior disorder (RBD+PD) and/or positive response to RBD Single-Question Screen (RBD1Q) and without hallucinations, and ADHD (attention deficit hyperactivity disorder).
33. The method of any of the preceding embodiments, wherein said patient is diagnosed with MCI.
34. The method of any of the preceding embodiments, wherein said patient is diagnosed with mild dementia.
35. The method of any of the preceding embodiments wherein, said patient is diagnosed with Parkinson's disease associated with REM sleep behavior disorder (RBD+PD).
36. The method of any of the preceding embodiments wherein, said patient is diagnosed with Parkinson's disease associated with REM sleep behavior disorder (RBD+PD) and/or positive response to RBD Single-Question Screen (RBD1Q).
37. The method of any of the preceding embodiments wherein, said patient is diagnosed with Parkinson's disease associated with REM sleep behavior disorder (RBD+PD) and/or positive response to RBD Single-Question Screen (RBD1Q) and without hallucinations.
38. The method of any of the preceding embodiments wherein, said patient is diagnosed with MCI or mild dementia due to Parkinson's disease associated with REM sleep behavior disorder (RBD+PD).
39. The method of any of the preceding embodiments wherein, said patient is diagnosed with MCI or mild dementia due to Parkinson's disease associated with REM sleep behavior disorder (RBD+PD) and/or positive response to RBD Single-Question Screen (RBD1Q).
40. The method of any of the preceding embodiments wherein, said patient is diagnosed with MCI or mild dementia due to Parkinson's disease associated with REM sleep behavior disorder (RBD+PD) and/or positive response to RBD Single-Question Screen (RBD1Q) and without hallucinations.
41. The method of any of the preceding embodiments, wherein said patient is diagnosed with MCI or mild dementia due to Alzheimer's disease.
42. The method of any of the preceding embodiments, wherein said patient is diagnosed with MCI due to Alzheimer's disease.
43. The method of any of the preceding embodiments, wherein said patient is diagnosed with mild dementia due to Alzheimer's disease 44. The method of any of the preceding embodiments, wherein said patient does not have Alzheimer's disease.
45. The method of any of the preceding embodiments, wherein said patient does not have Down Syndrome.
46. The method of any of the preceding embodiments, wherein said patient does not have Parkinson's disease.
47. The method of any of the preceding embodiments, wherein said patient does not have dementia with Lewy bodies.
48. The method of any of the preceding embodiments, wherein the tulobuterol is (S)-tulobuterol that is substantially free of (R)-tulobuterol.
49. The method of any of the preceding embodiments, wherein the tulobuterol is (R)-tulobuterol that is substantially free of (S)-tulobuterol.
50. A method, comprising:
subjecting a patient to a test to determine cognitive function and/or to identify whether said patient is in need of or desiring improvement of cognitive function and/or treatment of a neurodegenerative disease;
identifying a particular type of neurodegenerative disease based on a spatial pattern of the test result;
and subsequently administering to said patient a pharmaceutical composition comprising a β-agent, wherein the peripherally acting β-blocker (PABRA) is administered in a dose of about 15 mg or less.
51. A method, comprising:
subjecting a patient to a test to determine cognitive function and/or to identify whether said patient is in need of or desiring improvement of cognitive function and/or treatment of a neurodegenerative disease;
identifying a particular type of neurodegenerative disease based on a spatial pattern of the test result;
and subsequently administering to said patient a pharmaceutical composition comprising a β-agent, wherein the peripherally acting β-blocker (PABRA) is administered in a sub-therapeutic dose.
52. A method, comprising:
subjecting a patient to a test to determine cognitive function and/or to identify whether said patient is in need of or desiring improvement of cognitive function and/or treatment of a neurodegenerative disease;
identifying a particular type of neurodegenerative disease based on a spatial pattern of the test result;
administering to said patient a pharmaceutical composition to improve cognition and/or treat a neurodegenerative disease in said patient, said pharmaceutical composition comprising a β-agent, a $\beta_1$-AR agonist, a $\beta_2$-AR agonist, a peripherally acting β-blocker (PABRA), or any combination thereof, wherein the peripherally acting β-blocker (PABRA) is administered in a dose of about 15 mg or less; and
subsequently re-subjecting said patient to the test to determine any improvement in cognitive function and/or treatment of said neurodegenerative disease.
53. A method, comprising:
subjecting a patient to a test to determine cognitive function and/or to identify whether said patient is in need of or desiring improvement of cognitive function and/or treatment of a neurodegenerative disease;
identifying a particular type of neurodegenerative disease based on a spatial pattern of the test result;
administering to said patient a pharmaceutical composition to improve cognition and/or treat a neurodegenerative disease in said patient, said pharmaceutical composition comprising a β-agent, a $\beta_1$-AR agonist, a $\beta_2$-AR agonist, a peripherally acting β-blocker (PABRA), or any combination thereof, wherein the peripherally acting β-blocker (PABRA) is administered in a subtherapeutic dose; and
subsequently re-subjecting said patient to the test to determine any improvement in cognitive function and/or treatment of said neurodegenerative disease.
54. A method, comprising:
subjecting a patient to a test to determine cognitive function in said patient;
identifying a particular type of neurodegenerative disease based on a spatial pattern of the test result;
administering to said patient a pharmaceutical composition comprising a β-agent, a $\beta_1$-AR agonist, a $\beta_2$-AR agonist, a peripherally acting β-blocker (PABRA), or any combination thereof, wherein the peripherally acting β-blocker (PABRA) is administered in a dose of about 15 mg or less; and
subsequently re-subjecting said patient to the test to determine any improvement in cognitive function.
55. A method, comprising:
subjecting a patient to a test to determine cognitive function in said patient;
identifying a particular type of neurodegenerative disease based on a spatial pattern of the test result;
administering to said patient a pharmaceutical composition comprising a β-agent, a $\beta_1$-AR agonist, a $\beta_2$-AR agonist, a peripherally acting β-blocker (PABRA), or any combination thereof, wherein the peripherally acting β-blocker (PABRA) is administered in a subtherapeutic dose; and
subsequently re-subjecting said patient to the test to determine any improvement in cognitive function.
56. A method, comprising:
treating a subject identified as having diminished cognitive function and/or being in need of or desiring improvement of cognitive function and/or treatment of a neurodegenerative disease by administering the subject a pharmaceutical composition comprising a β-agent, a $\beta_1$-AR agonist, a $\beta_2$-AR agonist, a peripherally acting β-blocker (PABRA), or any combination thereof, wherein the peripherally acting β-blocker (PABRA) is administered in a dose of about 15 mg or less.
57. A method, comprising:
treating a subject identified as having diminished cognitive function and/or being in need of or desiring improvement of cognitive function and/or treatment of a neurodegenerative disease by administering the subject a pharmaceutical composition comprising a β-agent, $a_1$-AR agonist, a $\beta_2$-AR agonist, a peripherally acting β-blocker (PABRA), or any combination thereof, wherein the peripherally acting β-blocker (PABRA) is administered in a sub-therapeutic dose.
58. The method of any of the preceding embodiments, wherein the test is brain imaging.
59. The method of any of the preceding embodiments, wherein the test is fluorodeoxyglucose positron emission tomography (FDG-PET) scan, magnetic resonance imaging-arterial spin labeling (MRI-ASL), or magnetic resonance imaging-blood oxygenation level dependent computerized tomography (MRI-BOLD).
60. The method of any of the preceding embodiments, wherein the pharmaceutical composition comprises a β-agent and a PABRA.
61. The method of any of the preceding embodiments, wherein the β-agent is administered at a dose of from about 30 to 160 μg.

62. The method of any of the preceding embodiments, wherein the β-agent is administered at a dose of from about 50 to 160 μg.
63. The method of any of the preceding embodiments, wherein said β-agent is administered at a dose of from about 0.1 to 30 mg.
64. The method of any of the preceding embodiments, wherein said β-agent is administered at a dose of from about 30 to 200 mg.
65. The method of any of the preceding embodiments, wherein said dose of the β-agent is a total daily dose and is administered daily for a period of weeks or more.
66. The method of any of the preceding embodiments, wherein the dosage of the pharmaceutical composition is adjusted based on the test result.
67. The method of any of the preceding embodiments, wherein the peripherally acting (3-blocker (PABRA), if present, is one or more selected from the group consisting of nadolol, atenolol, sotalol and labetalol.
68. The method of any of the preceding embodiments, wherein the peripherally acting β-blocker (PABRA) is nadolol.
69. The method of any of the preceding embodiments, wherein the peripherally acting β-blocker (PABRA) is atenolol.
70. The method of any of the preceding embodiments, wherein the peripherally acting β-blocker (PABRA) is administered in a dose of about 0.1 to 30 mg.
71. The method of any of the preceding embodiments, wherein the peripherally acting β-blocker (PABRA) is administered in a dose of about 5 to 10 mg.
72. The method of any of the preceding embodiments, wherein said dose of the peripherally acting β-blocker (PABRA) is a total daily dose and is administered daily for a period of weeks or more.
73. The method of any of the preceding embodiments, wherein said dose of the peripherally acting β-blocker (PABRA) is a weekly dose and is administered weekly for a period of weeks or more.
74. The method of any of the preceding embodiments wherein the pharmaceutical composition is administered orally.
75. The method of any of the preceding embodiments wherein the neurodegenerative disease is one or more selected from the group consisting of MCI, aMCI, Vascular Dementia, Mixed Dementia, FTD (frontotemporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), and Down Syndrome.
76. The method of any of the preceding embodiments wherein the neurodegenerative disease is one or more selected from the group consisting of MCI, aMCI, Vascular Dementia, Mixed Dementia, FTD (frontotemporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder).
77. The method of any of the preceding embodiments, wherein said patient does not have Alzheimer's disease.
78. The method of any of the preceding embodiments, wherein said patient does not have Down Syndrome.
79. The method of any of the preceding embodiments, wherein said patient does not have Parkinson's disease.
80. The method of any of the preceding embodiments, wherein said patient does not have dementia with Lewy bodies.
81. A pharmaceutical tablet or capsule, comprising:
   a therapeutically effective amount of a β-agent, and
   a peripherally acting β-blocker (PABRA) in an amount from 15 mg or less.
82. A pharmaceutical tablet or capsule, comprising:
   a therapeutically effective amount of a β-agent, and
   a peripherally acting β-blocker (PABRA) in an amount that achieves a sub-therapeutic dose.
83. A pharmaceutical tablet or capsule, comprising:
   a β-agent in an amount from about 0.01 to 100 mg, and
   a peripherally acting β-blocker (PABRA) in an amount from 15 mg or less.
84. A pharmaceutical tablet or capsule, comprising:
   a β-agent in an amount from about 0.01 to 100 mg, and
   a peripherally acting β-blocker (PABRA) in a subtherapeutic dose.
85. A pharmaceutical tablet or capsule, comprising:
   a β-agent in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
   a peripherally acting β-blocker (PABRA) in an amount from 15 mg or less.
86. A pharmaceutical tablet or capsule, comprising:
   a β-agent in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
   a peripherally acting β-blocker (PABRA) in a subtherapeutic dose.
87. A joint formulation, comprising:
   a therapeutically effective amount of a β-agent, and
   a peripherally acting β-blocker (PABRA) in an amount that achieves a sub-therapeutic dose.
88. A joint formulation, comprising:
   A therapeutically effective amount of a β-agent, and
   a peripherally acting β-blocker (PABRA) in an amount from 15 mg or less.
89. A joint formulation, comprising:
   a β-agent in an amount from about 0.01 to 100 mg, and
   a peripherally acting β-blocker (PABRA) in an amount that achieves a sub-therapeutic dose.

90. A joint formulation, comprising:
a β-agent in an amount from about 0.01 to 100 mg, and
a peripherally acting β-blocker (PABRA) in an amount from 15 mg or less.

91. A joint formulation, comprising:
a β-agent in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in an amount that achieves a sub-therapeutic dose.

92. A joint formulation, comprising:
a β-agent in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in an amount from 15 mg or less.

93. A single formulation, comprising:
a therapeutically effective amount of a β-agent, and
a peripherally acting β-blocker (PABRA) in an amount that achieves a sub-therapeutic dose.

94. A single formulation, comprising:
a therapeutically effective amount of a β-agent, and
a peripherally acting β-blocker (PABRA in an amount from 15 mg or less.

95. A pharmaceutical tablet or capsule, comprising:
a therapeutically effective amount of Compound 03-5, and
a peripherally acting β-blocker (PABRA) in an amount that achieves a sub-therapeutic dose.

96. A pharmaceutical tablet or capsule, comprising:
Compound 03-5 in an amount from about 0.01 to 100 mg, and
a peripherally acting β-blocker (PABRA) in an amount from 15 mg or less.

97. A pharmaceutical tablet or capsule, comprising:
Compound 03-5 in an amount from about 0.01 to 100 mg, and
a peripherally acting β-blocker (PABRA) in a subtherapeutic dose.

98. A pharmaceutical tablet or capsule, comprising:
Compound 03-5 in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in an amount from 15 mg or less.

99. A pharmaceutical tablet or capsule, comprising:
Compound 03-5 in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in a subtherapeutic dose.

100. A joint formulation, comprising:
a therapeutically effective amount of Compound 03-5, and
a peripherally acting β-blocker (PABRA) in an amount that achieves a sub-therapeutic dose.

101. A joint formulation, comprising:
A therapeutically effective amount of a β-agent, and
a peripherally acting β-blocker (PABRA) in an amount from 15 mg or less.

102. A joint formulation, comprising:
Compound 03-5 in an amount from about 0.01 to 100 mg, and
a peripherally acting β-blocker (PABRA) in an amount that achieves a sub-therapeutic dose.

103. A joint formulation, comprising:
Compound 03-5 in an amount from about 0.01 to 100 mg, and
a peripherally acting β-blocker (PABRA) in an amount from 15 mg or less.

104. A joint formulation, comprising:
Compound 03-5 in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in an amount that achieves a sub-therapeutic dose.

105. A joint formulation, comprising:
Compound 03-5 in an amount from about 0.5-20 mg; or 1-10 mg; or 2-8 mg; or about 1 mg; or about 2 mg; or about 3 mg; or about 4 mg; or about 5 mg; or about 6 mg; or about 7 mg; or about 8 mg; or about 10 mg, and
a peripherally acting β-blocker (PABRA) in an amount from 15 mg or less.

106. A single formulation, comprising:
a therapeutically effective amount of Compound 03-5, and
a peripherally acting β-blocker (PABRA) in an amount that achieves a sub-therapeutic dose.

107. A single formulation, comprising:
a therapeutically effective amount of Compound 03-5, and
a peripherally acting β-blocker (PABRA in an amount from 15 mg or less.

108. The method or composition of any one of the preceding embodiments wherein, the PABRA is administered at a sub-therapeutic dose.

109. The method or composition of any one of the preceding embodiments wherein the dose of the PABRA is 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a dose that the agent is effective for, or approved for treating a specific disease indication.

110. The method or composition of any one of the preceding embodiments wherein the PABRA is administered at a sub-therapeutic dose that is 90% or less; or 85% or less; or 80% or less; or 75% or less; or 70% or less; or 65% or less; or 60% or less; or 55% or less; or 50% or less; or 45% or less; or 40% or less; or 35% or less; or 30% or less; or 25% or less; or 20% or less; or 15% or less; or 10% or less; or 5% or less; or 4% or less; or 3% or less; or 2.5% or less; or 2% or less; or 1.5% or less; or 1% or less; or 0.5% or less as compared to a dose that the agent is approved for treating a specific disease indication.

111. The method or composition of any one of the preceding embodiments wherein the total daily dose of the β-agent is from about 1 to 300 μg, 5 to 200 μg, 10 to 180 μg, 10 to 40 μg, 20 to 50 μg, 40 to 80 μg, 50 to 100 μg, 100 to 200 μg, 30 to 160 μg, 50 to 160 g, 80 to 160 μg, 100 to 160 μg, 120 to 160 μg, 140 to 160 μg, 150 to 170 μg, 30 to 140 μg, 50 to 140 μg, 80 to 140 μg, 100 to 140 μg, 120 to 140 μg, 30 to 120 μg, 50 to 120 μg, 80 to 120 μg, 100 to 120 μg, 30 to 100 μg, 50 to 100 μg, 80 to 100 μg, 30 to 80 μg, 50 to 80 μg, 30 to 50 μg, about 10 μg, about 20 μg, about 25 μg, about 30 μg, about 40 μg, about 50 μg, about 60 μg, about 70 μg, about 80 μg, about 90 μg, about 100 μg, about 110 μg, about 120 μg, about 125 μg, about 130 μg, about 140 μg, about 150 μg, or about 160 μg, about 170 μg, about 175 μg, about 180 μg, about 190 μg, about or 200 μg.

112. The method or composition of any one of the preceding embodiments wherein the (3-agent is administered at a dose from 0.5-20 mg; or 1-10 mg; or 2-8 mg; or 1-15 mg; or 3-12 mg; or about 1 mg; or about 2 mg; or about 3 mg; or about 4 mg; or about 5 mg; or about 6 mg; or about 7 mg; or about 8 mg; or about 10 mg; or about 11 mg; or about 12 mg; or about 13 mg; or about 15 mg.

113. The method or composition of any one of the preceding embodiments wherein the (3-agent is a compound with a structure of Formula (I), Formula (I''), Formula (II), Formula (III), Formula (I'), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), or Formula (XXV'); or an optically pure stereoisomer, pharmaceutically acceptable salt, solvate, or prodrug thereof.

114. The method or composition of any one of the preceding embodiments wherein the β-agent is a compound with a structure of Formula (I) or an optically pure stereoisomer, pharmaceutically acceptable salt, solvate, or prodrug thereof.

115. The method or composition of any one of the preceding embodiments wherein the β-agent is a compound with a structure of Formula (I'') or an optically pure stereoisomer, pharmaceutically acceptable salt, solvate, or prodrug thereof.

116. The method or composition of any one of the preceding embodiments wherein the β-agent is a compound with a structure of Formula (II) or an optically pure stereoisomer, pharmaceutically acceptable salt, solvate, or prodrug thereof.

117. The method or composition of any one of the preceding embodiments wherein the β-agent is a compound with a structure of Formula (III) or an optically pure stereoisomer, pharmaceutically acceptable salt, solvate, or prodrug thereof.

118. The method or composition of any one of the preceding embodiments wherein the β-agent is a compound with a structure of Formula (I') or an optically pure stereoisomer, pharmaceutically acceptable salt, solvate, or prodrug thereof.

119. The method or composition of any one of the preceding embodiments wherein the β-agent is a compound with a structure of Formula (II') or an optically pure stereoisomer, pharmaceutically acceptable salt, solvate, or prodrug thereof.

120. The method or composition of any one of the preceding embodiments wherein the β-agent is a compound with a structure of Formula (III') or an optically pure stereoisomer, pharmaceutically acceptable salt, solvate, or prodrug thereof.

121. The method or composition of any one of the preceding embodiments wherein the β-agent is a compound with a structure of Formula (IV') or an optically pure stereoisomer, pharmaceutically acceptable salt, solvate, or prodrug thereof.

122. The method or composition of any one of the preceding embodiments wherein the β-agent is a compound with a structure of Formula (V') or an optically pure stereoisomer, pharmaceutically acceptable salt, solvate, or prodrug thereof.

123. The method or composition of any one of the preceding embodiments wherein the β-agent is a compound with a structure of Formula (VI') or an optically pure stereoisomer, pharmaceutically acceptable salt, solvate, or prodrug thereof.

124. The method or composition of any one of the preceding embodiments wherein the β-agent is a compound with a structure of Formula (VII'); or an optically pure stereoisomer, pharmaceutically acceptable salt, solvate, or prodrug thereof.

125. The method or composition of any one of the preceding embodiments wherein the β-agent is a compound with a structure of Formula (VIII') or an optically pure stereoisomer, pharmaceutically acceptable salt, solvate, or prodrug thereof.

126. The method or composition of any one of the preceding embodiments wherein the β-agent is a compound with a structure of Formula (IX') or an optically pure stereoisomer, pharmaceutically acceptable salt, solvate, or prodrug thereof.

127. The method or composition of any one of the preceding embodiments wherein the β-agent is a compound with a structure of Formula (X') or an optically pure stereoisomer, pharmaceutically acceptable salt, solvate, or prodrug thereof.

128. The method or composition of any one of the preceding embodiments wherein the β-agent is a compound with a structure of Formula (XI') or an optically pure stereoisomer, pharmaceutically acceptable salt, solvate, or prodrug thereof.

129. The method or composition of any one of the preceding embodiments wherein the β-agent is a compound with a structure of Formula (XII') or an optically pure stereoisomer, pharmaceutically acceptable salt, solvate, or prodrug thereof.

130. The method or composition of any one of the preceding embodiments wherein the β-agent is a compound with a structure of Formula (XIII') or an optically pure stereoisomer, pharmaceutically acceptable salt, solvate, or prodrug thereof.

131. The method or composition of any one of the preceding embodiments wherein the β-agent is a compound with a structure of Formula (XIX') or an optically pure stereoisomer, pharmaceutically acceptable salt, solvate, or prodrug thereof.

132. The method or composition of any one of the preceding embodiments wherein the β-agent is a compound with a structure of Formula (XX') or an optically pure stereoisomer, pharmaceutically acceptable salt, solvate, or prodrug thereof.

133. The method or composition of any one of the preceding embodiments wherein the β-agent is a compound with a structure of Formula (XXI') or an optically pure stereoisomer, pharmaceutically acceptable salt, solvate, or prodrug thereof.
134. The method or composition of any one of the preceding embodiments wherein the β-agent is a compound with a structure of Formula (XXII') or an optically pure stereoisomer, pharmaceutically acceptable salt, solvate, or prodrug thereof.
135. The method or composition of any one of the preceding embodiments wherein the β-agent is a compound with a structure of Formula (XXIII') or an optically pure stereoisomer, pharmaceutically acceptable salt, solvate, or prodrug thereof.
136. The method or composition of any one of the preceding embodiments wherein the β-agent is a compound with a structure of Formula (XXIV') or an optically pure stereoisomer, pharmaceutically acceptable salt, solvate, or prodrug thereof.
137. The method or composition of any one of the preceding embodiments wherein the β-agent is a compound with a structure of Formula (XXV') or an optically pure stereoisomer, pharmaceutically acceptable salt, solvate, or prodrug thereof.
138. The method or composition of any one of the preceding embodiments wherein the β-agent is a compound of Table 1.
139. The method or composition of any one of the preceding embodiments wherein the β-agent is a compound having the structure:

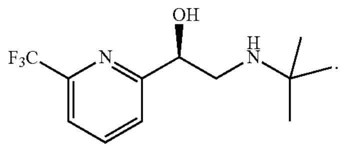 [SMILES: CC(C)(C)NC[C@H](O)c1cccc(C(F)(F)F)n1]

140. The method or composition of any one of the preceding embodiments wherein the β-agent is a compound having the structure:

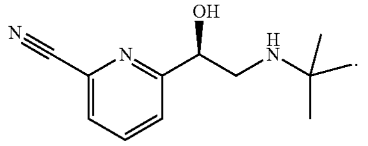 [SMILES: CC(C)(C)NC[C@H](O)c1cccc(C#N)n1]

141. The method or composition of any one of the preceding embodiments wherein the β-agent is a compound having the structure:

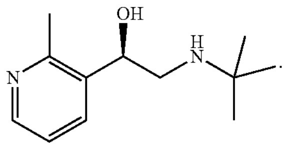

EXAMPLES

The present disclosure will be further described in the following examples, which do not limit the scope of the present disclosure.

Example 1: Treatment of Human Patients with Clenbuterol

Patients are screened using FDG-PET brain imaging. The identified as diagnosed with one or more of MCI, aMCI, Vascular Dementia, mild dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), Parkinson's disease associated with REM sleep behavior disorder (RBD+PD) and/or positive response to RBD Single-Question Screen (RBD1Q) and without hallucinations, MCI or mild dementia due to Parkinson's disease associated with REM sleep behavior disorder (RBD+PD) and/or positive response to RBD Single-Question Screen (RBD1Q) and without hallucinations, or ADHD (attention deficit hyperactivity disorder).

A single dose of clenbuterol was provided to the patients ranging in an amount from 30 to 160 μg. A single dose of nadolol was also administered in some patients in an amount of 5 mg to counter any adverse effects of the clenbuterol. The patient are tracked over the course of 3 days after the single dose of clenbuterol and/or nadolol. The patients demonstrated robust global increase in cerebral blood flow from the baseline following treatment with clenbuterol and/or nadolol.

As shown in FIG. 1, a first group of patients was administered a single dose of clenbuterol in an amount of 160 μg and a second group of patients was administered a single dose of clenbuterol in an amount of 160 μg and nadolol in an amount of 5 mg. Relative to their baseline prior to the single dose of treatment, clenbuterol produces a robust global increase in cerebral blood flow (CBF) relative to the baseline in these patients. The second group of patients also demonstrated a robust global increase in cerebral blood flow (CBF) relative to the baseline in these patients, in which nadolol was also administered with clenbuterol to counter any adverse effects of clenbuterol.

Figure 3:
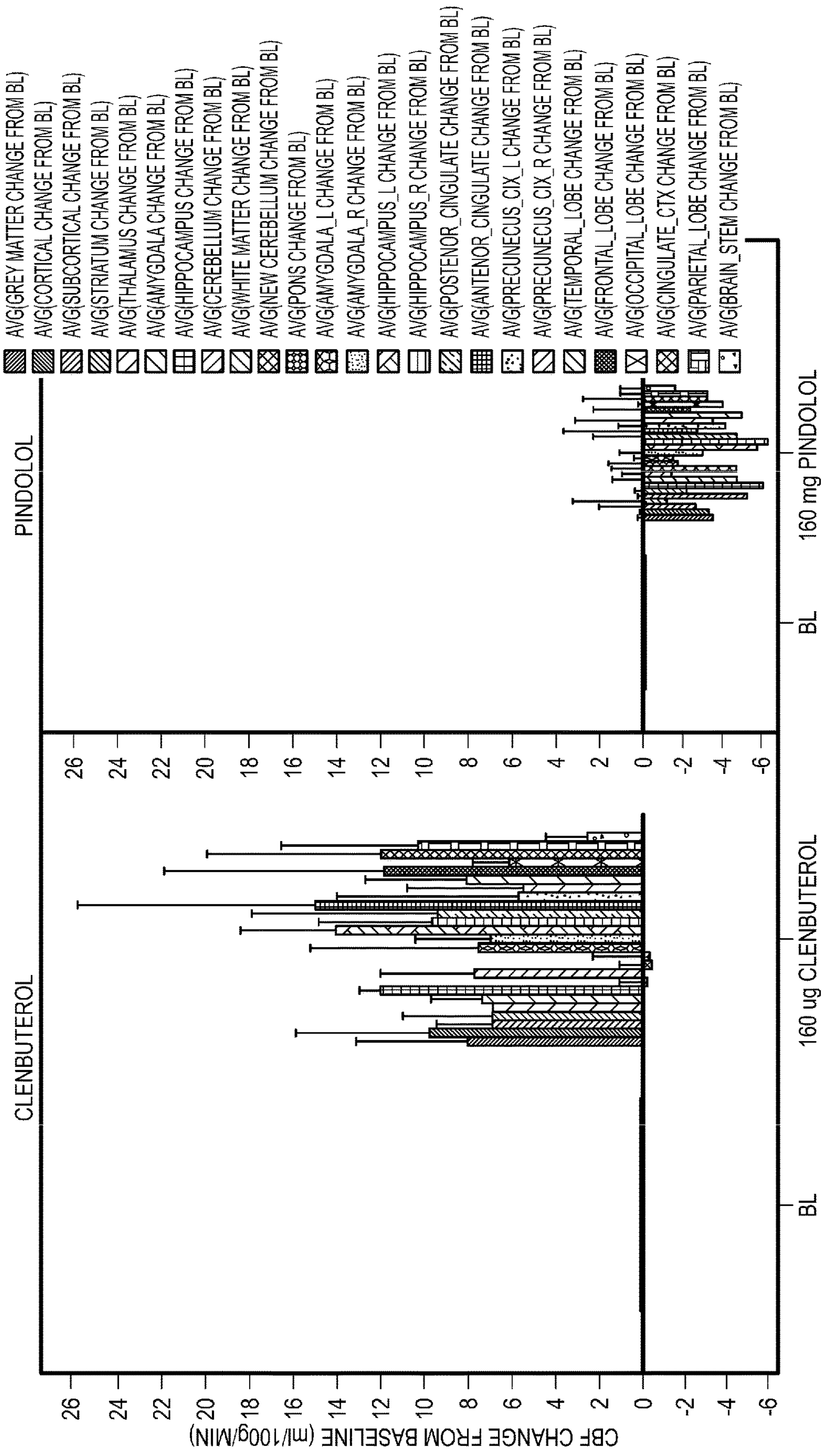
FIG. 3 shows a graph of cerebral blood flow in patients after being administered a single dose of clenbuterol and patients after being administered a single dose of pindolol relative to their baseline.

As shown in FIG. 3, a first group of patients was administered a single dose of clenbuterol in an amount of 160 μg and a second group of patients was administered a single dose of pindolol in an amount of 60 mg. Treatment with clenbuterol showed a positive increase in cerebral blood flow relative to the base line. Treatment with pindolol showed a decrease in cerebral blood flow relative to the base line.

Figure 4:
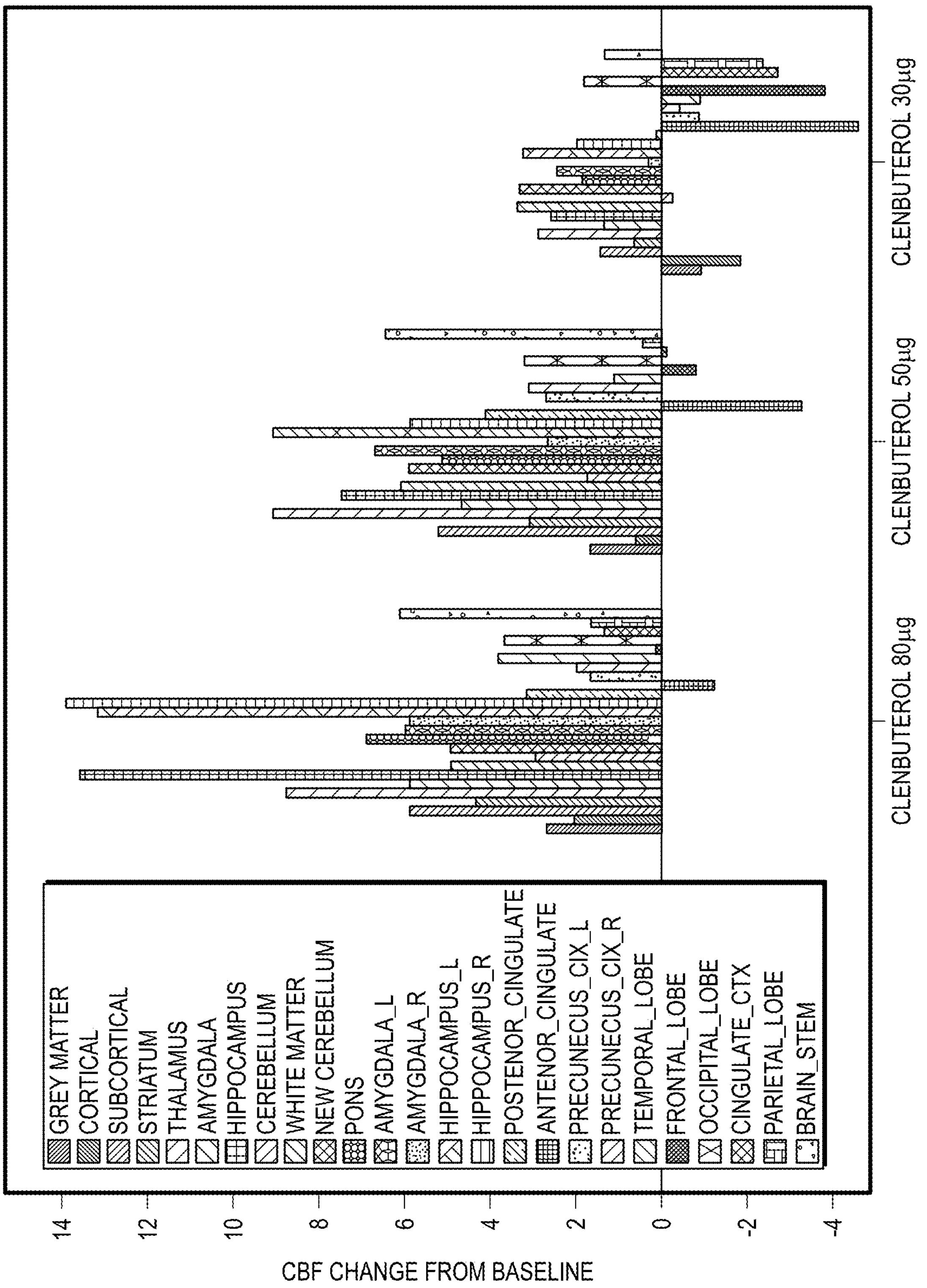
FIG. 4 shows a graph of cerebral blood flow in patients after being administered a single dose of clenbuterol in varying amounts relative to their baseline.
Figure 5:
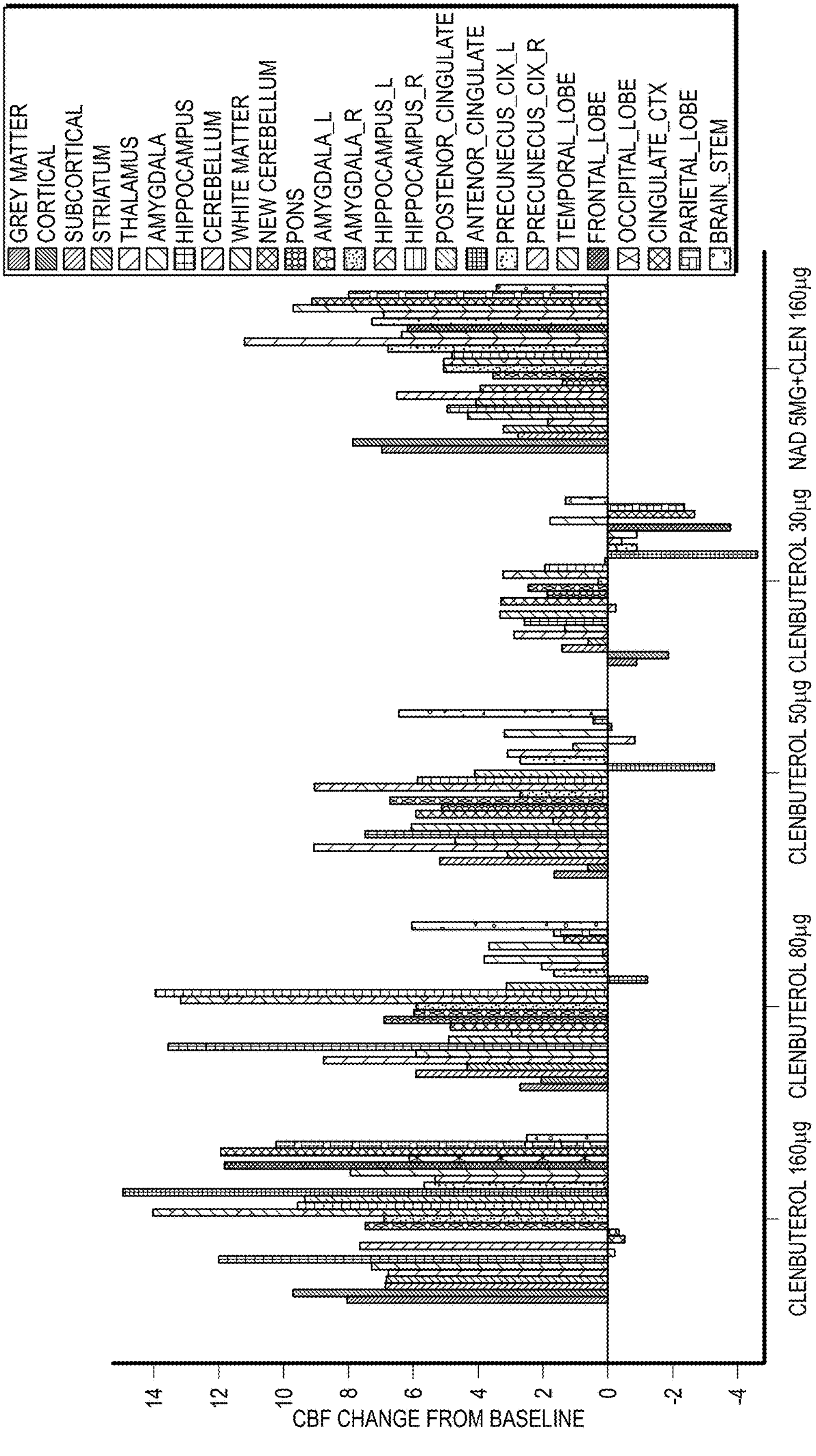
FIG. 5 shows a graph of cerebral blood flow in patients after being administered a single dose of clenbuterol in varying amounts and patients after being administered a single dose of clenbuterol and nadolol relative to their baseline.

As shown in FIGS. 4 and 5, a groups of patients were administered a single dose of varying amounts of clenbuterol ranging from 30 to 160 μg, and another group of patients was administered a single dose of clenbuterol in an amount of 160 μg and nadolol in an amount of 5 mg to counter any adverse effects of clenbuterol. The patients were tracked over the course of 3 days. Relative to their baseline prior to the single dose of treatment, clenbuterol in an amount ranging from 30 to 160 μg produces a robust global increase in cerebral blood flow (CBF) relative to the baseline in these patients. The patients administered a single dose of clenbuterol in an amount of 160 μg and nadolol in an amount of 5 mg also showed a robust global increase in cerebral blood flow (CBF) relative to the baseline.

In some embodiments, cognitive tests and/or FDG-PET imaging can be used. In some embodiments, magnetic resonance imaging-arterial spin labeling (MRI-ASL) can be used for neuroimaging. In some embodiments, magnetic resonance imaging-blood oxygenation level dependent computerized tomography (MRI-BOLD) can be used for neuroimaging.

Example 2: Synthesis of Compound 03-5 and 03-48

The below Scheme illustrates the synthesis of compound 03-5 and 03-48.

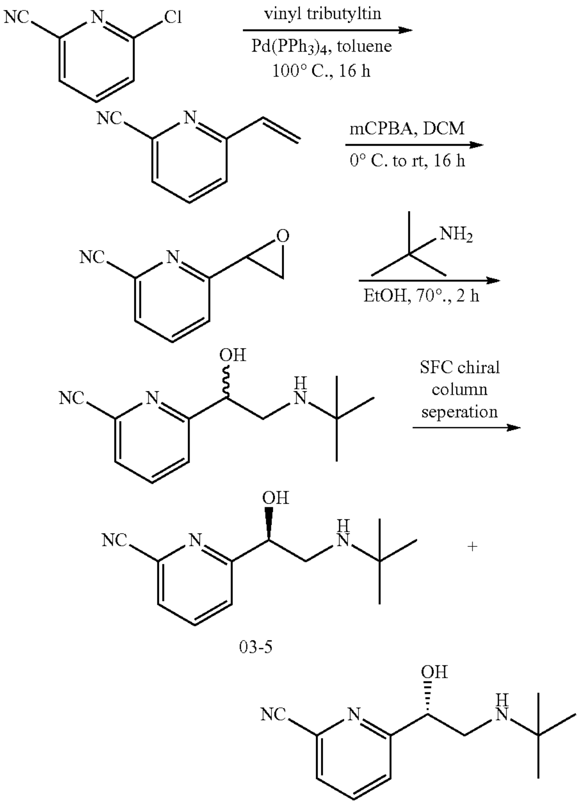

03-5

03-48

Step 1. Synthesis of 2-cyano-6-vinylpyridine

To a stirred mixture of 2-chloro-6-cyanopyridine (8.0 g, 69.3 mmol), 1-vinyltri-n-butyltin (21.97 g, 69.29 mmol, 20.34 mL), and $Pd(PPh_3)_4$ (3.34 g, 3.61 mmol) in anhydrous toluene (150 mL) was bubbled with $N_2$ for 5 min, before heating to 80° C. overnight. After cooling, the reaction mixture was poured into an aqueous solution of KF (40 g in 200 mL) and stirred for 30 min. The mixture was then filtered through celite and solid was washed with EtOAc (2×50 mL). The aqueous phase of the filtrate was separated and extracted with EtOAc (2×250 mL). The combined organic phases were washed with brine, dried over $Na_2SO_4$, filtered and concentrated under reduced pressure. The residue was purified by flash chromatography eluting with Hexanes/EtOAc (silica, 95/5 to 90/10) to provide 2-cyano-6-vinylpyridine as a pale yellow liquid (6.5 g, 86%). MS (m/z): 131.1 (M+H)+.

Step 2: Synthesis of 6-(oxiran-2-yl)picolinonitrile

To a stirred solution of 2-cyano-6-vinylpyridine (6.5 g, 49.94 mmol) in DCM (300 mL) was added mCPBA (61.56 g, 249.72 mmol) at 0° C. slowly portion wise over a period of 30 min and stirred at RT for 24 h. After completion of reaction, reaction mixture was cooled to 5° C. and added aqueous saturated $NaHCO_3$ solution and extracted with DCM (200 mL×2). Organic layers were combined, dried over $Na_2SO_4$, filtered, and concentrated under reduced pressure. The residue was purified by flash chromatography eluting with Hexanes/EtOAc (silica, 90/10 to 80/20) to provide 6-(oxiran-2-yl)picolinonitrile as a colorless liquid (3.85 g, 52%). MS (m/z): 147.1 (M+H)+.

Step 3: Synthesis of (S)-6-(2-(tert-butylamino)-1-hydroxyethyl)picolinonitrile and (R)-6-(2-(tert-butylamino)-1-hydroxyethyl)picolinonitrile To a stirred solution of 6-(oxiran-2-yl) picolinonitrile (3.5 g, 18.2 mmol) in ethanol (25 mL) was added tert-butylamine (6.66 g, 91.0 mmol). The reaction mixture was stirred at 80° C. for 3 h in a sealed tube, while monitoring reaction by TLC and LCMS. After completion of reaction, solvent was evaporated to get a residue, which was purified by reverse phase chromatography to provide desired products as a racemic mixture. A racemic mixture was separated by SFC (Chiralpak AS-H (30*250) mm, 5μ column, using $CO_2$: 80% Co-solvent: 20% (0.2% isopropylamine in IPA as eluent) to provide compound 03-5 (S)-6-(2-(tert-butylamino)-1-hydroxyethyl)picolinonitrile (1.05 g, 26.3%) and compound 03-48 (R)-6-(2-(tert-butylamino)-1-hydroxyethyl)picolinonitrile (0.98 g, 24.5%) as white solids. Compound 03-5: $^1$HNMR 400 MHz, DMSO-d6: δ 8.03 (t, J=8.00 Hz, 1H), 7.90 (dd, J=0.80 Hz, 7.60 Hz, 1H), 7.82 (d, J=8.00 Hz, 1H), 5.63 (s, 1H), 4.60 (q, J=4.40 Hz, 1H), 2.86-2.80 (m, 1H), 2.67-2.49 (m, 1H), 1.44-1.40 (m, 1H), 0.98 (s, 9H). Compound 03-48: $^1$HNMR 400 MHz, DMSO-d6: δ 8.03 (t, J=7.60 Hz, 1H), 7.90 (d, J=6.80 Hz, 1H), 7.82 (d, J=8.00 Hz, 1H), 5.62 (s, 1H), 4.60 (s, 1H), 2.81-2.82 (m, 1H), 2.62-2.64 (m, 1H), 1.44 (s, 1H), 0.98 (s, 9H).

Example 3: Cerebral Perfusion

Several recent studies have demonstrated the clinical relevance of cerebral perfusion (De Vis 2018, Staffaroni 2019). These studies demonstrate that cerebral perfusion declines with age, is correlated with the progression of AD, and is strongly correlated with cognitive performance such that subjects with higher cerebral perfusion tend to perform better in cognitive tests. Additionally, a study in AD patients demonstrated that the clinical effect of donepezil could be predicted by the perfusion increase seen after a single dose of the drug such that the subjects who had an increase in perfusion after acute administration were the same subjects who had a cognitive improvement after 6 months of treatment with the drug (Tepmongkol 2019). In a clinical study, healthy subjects were administered doses of clenbuterol ranging from 20 to 160 μg and ASL MRI was conducted prior to and after dosing with an objective to ascertain whether this neuroimaging method enables the detection of a clinically relevant CNS signal. The neuroimaging data from the study using ASL MRI demonstrated a clinically relevant signal, an increase in cerebral perfusion after a single dose of clenbuterol. specifically, 160 μg of clenbuterol causes a robust global increase in cerebral perfusion and in particular in areas such as the hippocampus, thalamus, and cortex, all of which are very relevant in the pathogenesis of neurodegenerative disorders (see FIG. 6)

Figure 6:
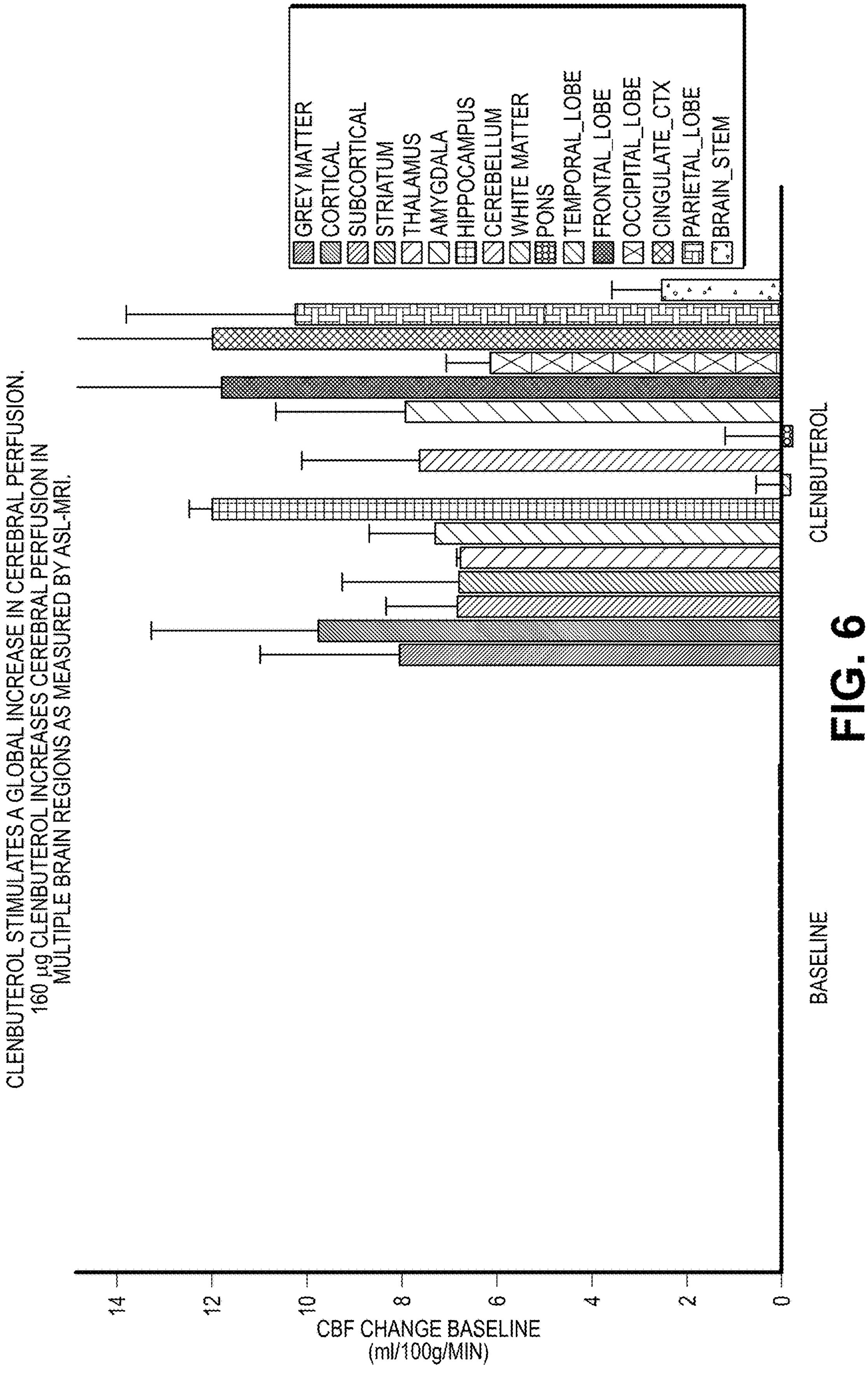
FIG. 6 shows that after dosing with a single dose of 160 μg of clenbuterol there is a global increase in cerebral perfusion. The legend on the right shows the different regions of interest (ROIs). The data are plotted as change from baseline in cerebral blood flow in different regions of the brain.
Figure 7:
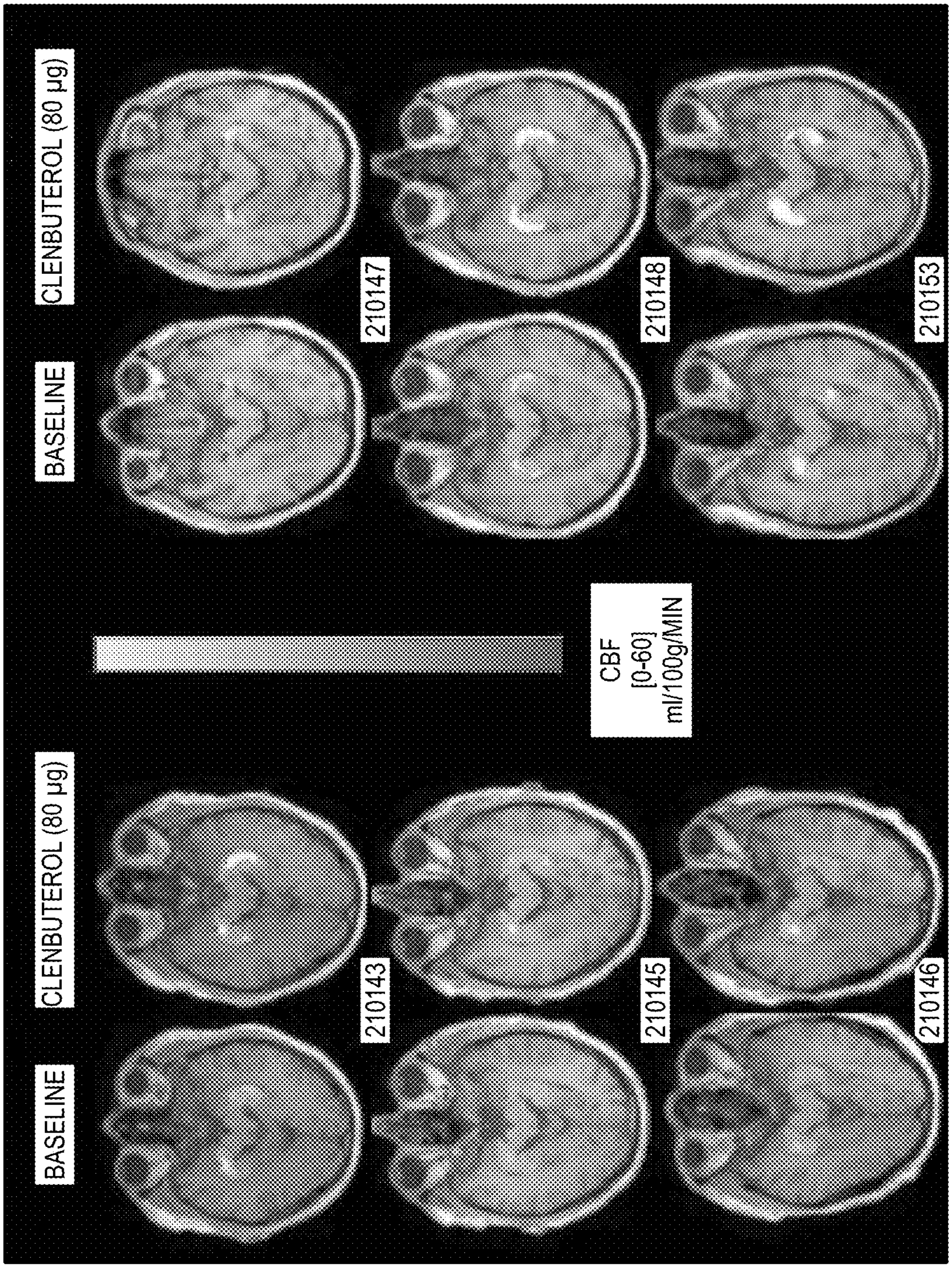
FIG. 7 shows a perfusion MRI-ASL image of the hippocampus as the region of interest (ROI). Six healthy subjects aged 44-52 were treated with a single dose of 80 μg clenbuterol. The Baseline vs. post-dose paired t-tests results: $p=0.019$. The color scale is shown in the middle and indicates cerebral blood flow with low values in red and high values in yellow.
Figure 8:
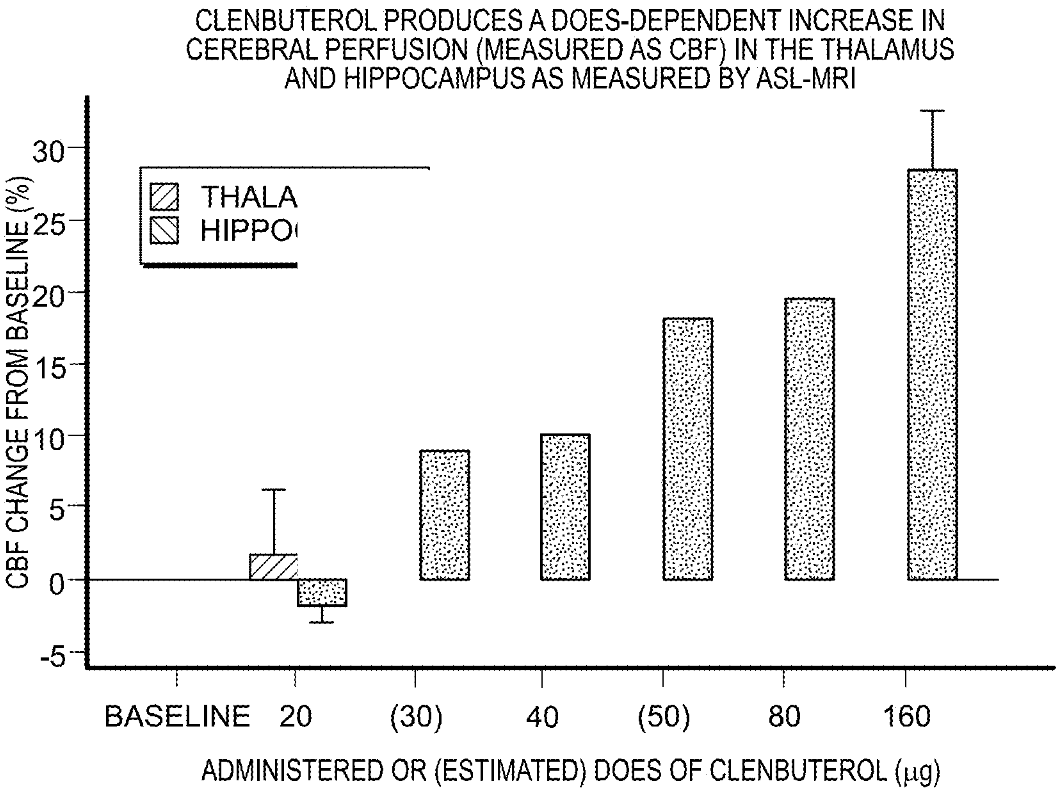
FIG. 8 shows that in a cohort 5 of the study, "estimated doses" of clenbuterol were based on dose equivalents calculated from PK modeling of exposures at 24 hours (estimated dose of 50 μg) and 48 hours (estimated dose of 30 μg) after a single dose of 80 μg clenbuterol administered to subjects on Day 1.

In a region of interest (ROI) analysis focusing on the hippocampus, which is well understood to be affected in neurodegenerative disorders, a single dose of 80 μg of clenbuterol causes a robust increase in perfusion (see FIG. 7). In this cohort of 6 healthy subjects treated with a single dose of 80 μg of clenbuterol every subject had an increase in hippocampal perfusion, which on average was 25%. The neuroimaging data from the study using ASL MRI demonstrated that doses of 80 and 160 μg of clenbuterol stimulate a robust, global increase in perfusion. In particular, areas of the brain thought to be relevant to the neuropathology of neurodegenerative disorders demonstrate significant improvements in perfusion in the range of 25% (FIGS. 6 and 7). An ROI analysis of the hippocampus in 6 healthy subjects aged 44 to 52 demonstrates a robust increase in this area of the brain for each subject FIG. 7. Taken together with other cohorts in which ASL MRI was conducted, a clear dose response relationship is seen between dose of clenbuterol and cerebral perfusion (FIG. 8). Doses below 30 μg do not produce significant cerebral perfusion increases as measured by CBF and a dose of 40 μg produces a minimal increase while doses of 80 and 160 μg produce global increases in cerebral perfusion, with particularly robust increases of 20% to 25% in areas of the brain relevant to neurodegenerative disorders such as the hippocampus and the thalamus (FIG. 8, Bartsch 2015, Leh 2016). Our hypothesis is that by improving cerebral perfusion, particularly in areas of the brain that are relevant for symptoms that are commonly found in neurodegenerative diseases such as PD and AD, the administration of a β-AR agonist (such as a β-agent) will have a positive effect on clinically relevant symptoms such as memory and cognition. In particular for cognition, preliminary data from the study suggest that a single dose of 160 μg of clenbuterol improves cognition in healthy subjects as measured by adaptive tracking and word recall.

Example 4: Treatment of Human Patients with a β-Agent and PABRA

The procedures described in Examples 1 and 3 are repeated, replacing clenbuterol or other $\beta_2$-AR agonist with a β-agent (such as, for example Compound 03-5). The starting dose of the β-agent is determined by preclinical study and the clinical dose is optimized.

Example 5: Clinical Effectiveness

Figure 9:
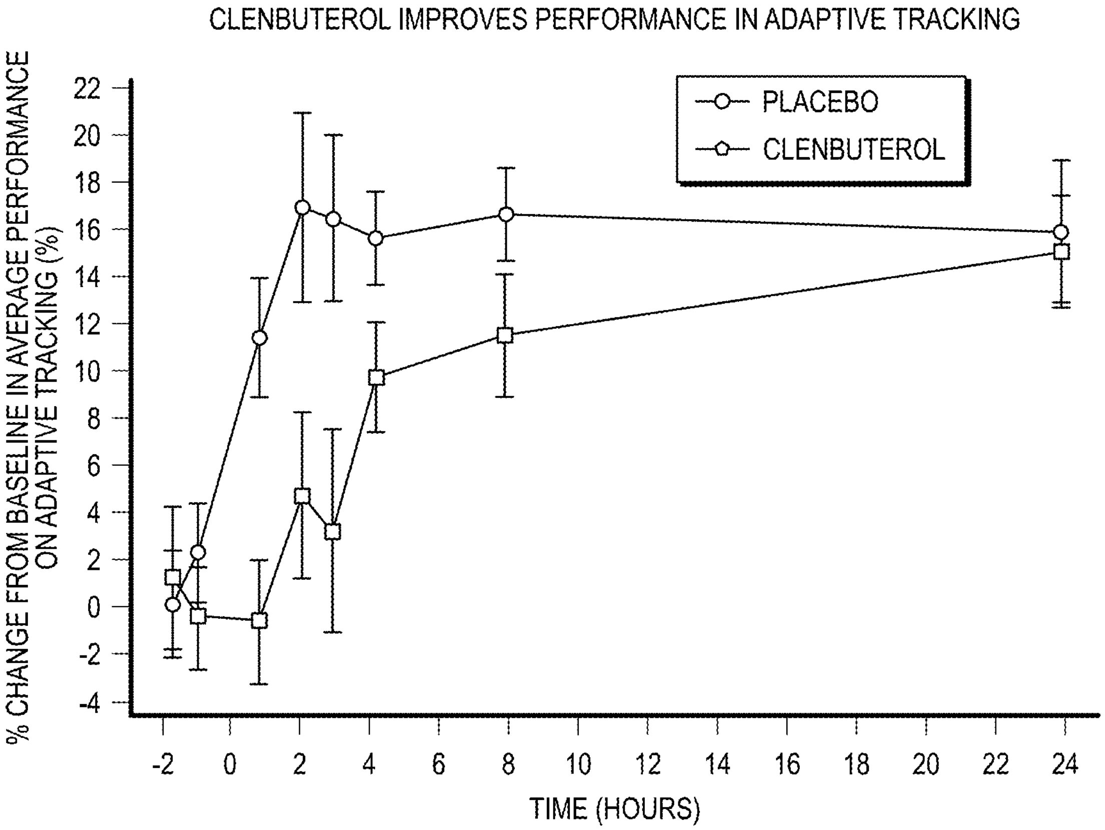
FIG. 9 shows improved adaptive tracking in response to clenbuterol.

Adaptive tracking measures visuomotor coordination and vigilance. In this test, the subject uses a joystick to move a small dot so that it stays within a continuously moving circle on a computer screen (Boland 1984). During the test, the speed of the circle is adjusted in response to the subject's ability to keep the dot in the circle, ensuring that the test is adapted to the individual subject. Results suggest that after a single dose of 160 μg clenbuterol performance in adaptive tracking improves as measured by the percent time that the subject is able to keep the small dot within the moving circle (see FIG. 9). The improvement shown by subjects is in the same range as that seen with subjects treated with the acetylcholinesterase inhibitor donepezil, which is in clinical use for the treatment of mild to moderate AD (Groeneveld 2016).

Figure 10:
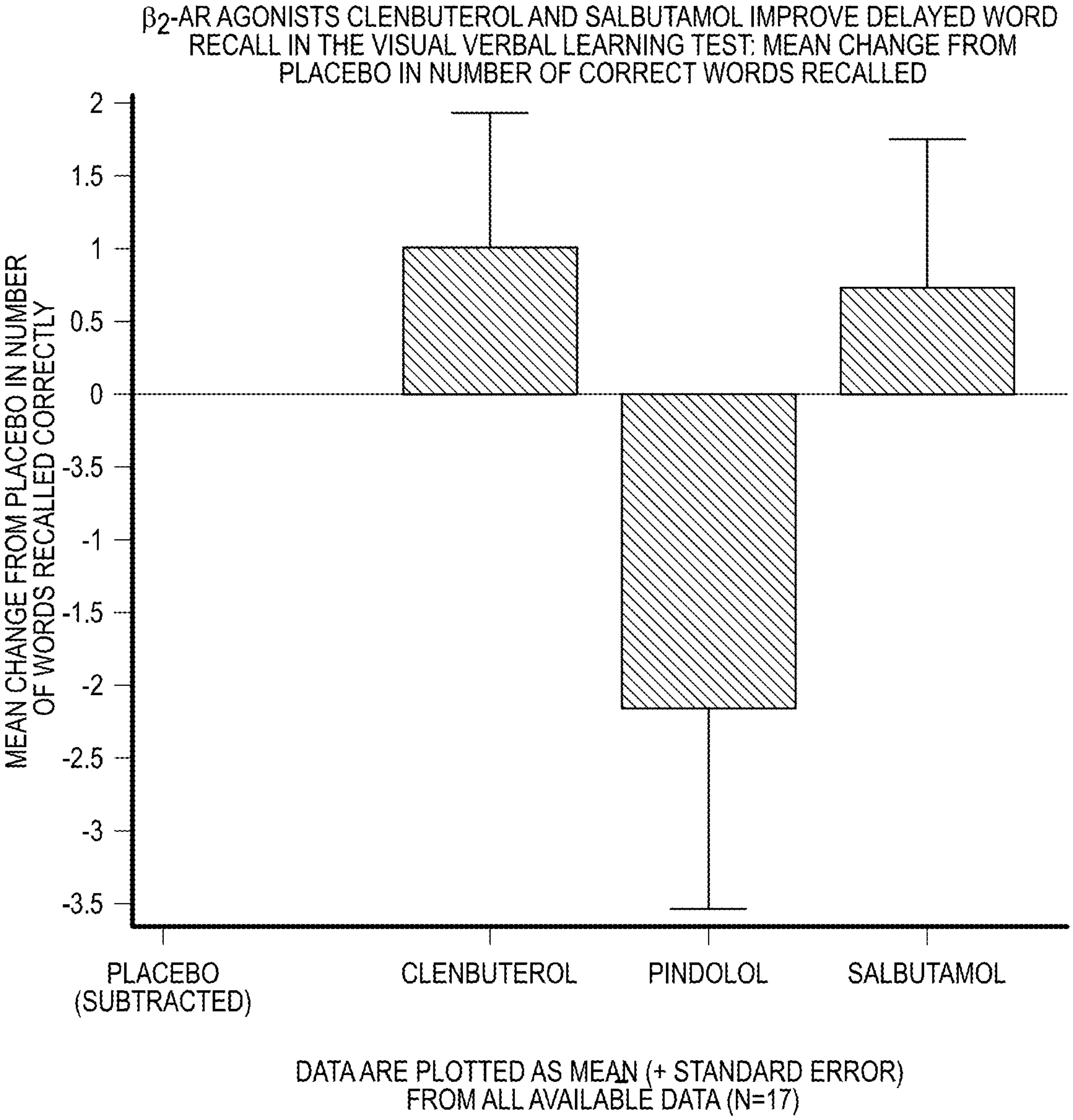
FIG. 10 shows effects of clenbuterol and a $\beta_2$-AR antagonist/$\beta_1$-AR partial agonist on the visual verbal learning test (VVLT).

The visual verbal learning test (VVLT) is a test for learning and memory (de Haas 2009). Subjects are presented 30 words on a screen, one at a time, for 1 second with a 1-second interval between words over a total of 1 minute. This is repeated in 3 trials. After each trial, subjects are asked to recall as many words as they can. After the third trial, there is a delay of 2.5 hours and subjects are then tested once for delayed recall. Clenbuterol improved performance in VVLT in both the immediate recall (Trial 1, not shown) and the delayed recall (see FIG. 10). The effect for clenbuterol is an improvement in approximately 1.5 to 2 correctly recalled words, which is clinically meaningful. Since this was a crossover study, everyone who completed Part A was dosed with the 3 agents plus placebo. The $\beta_2$-AR agonists tested in this study, clenbuterol and salbutamol, had positive effects on the VVLT. In contrast, the $\beta_2$-AR antagonist/$\beta_1$-AR partial agonist pindolol had a detrimental effect on this learning and memory test.

Example 6: Treatment of Human Patients with Compound 03-5 and Nadolol

Healthy volunteers were be enrolled into 2 cohorts in a study to undertake within-subject dose titration of Compound 03-5 and/or nadolol in order to explore doses/dose combinations that mitigate peripheral effects of Compound 03-5, e.g. on heart rate, while preserving possible central effects of Compound 03-5 on cerebral perfusion and pupillary light reflex.

A. Cohort D1.

Cohort D1 enrolled 8 healthy subjects and undertook an evaluation of the effects of treatment on ECG following repeat dosing of Compound 03-5 in the presence of escalating doses of nadolol according to following schematic.

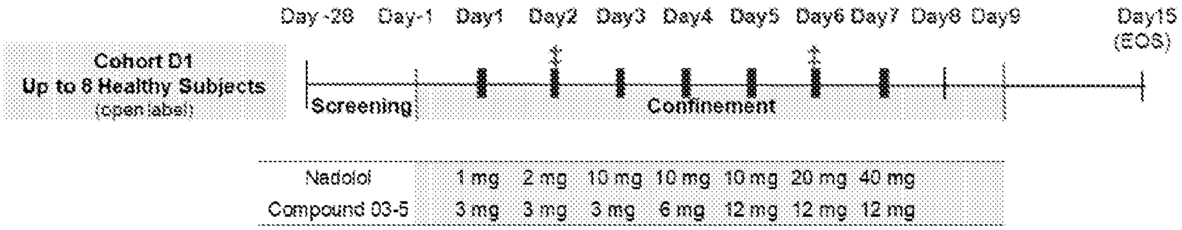
Day -28
Day-1
Day1
Day2
Day3
Day4
Day5
Day6
Day7
Day8
Day9
Day15 (EOS)
Cohort D1
Up to 6 Healthy Subjects
(open label)
Screening
Confinement
Nadolol 1 mg 2 mg 10 mg 10 mg 10 mg 20 mg 40 mg
Compound 03-5 3 mg 3 mg 3 mg 6 mg 12 mg 12 mg 12 mg Compound 03-5 dosing day(s). A single dose of nadolol (up to 40 mg) will be pre-administered or co-administered with Compound 03-5 on one or more of the dosing days. The dose of Compound 03-5 and/or nadolol may vary over the 7 dosing days. For example, the dose of Compound 03-5 may be 3 mg on Day 1 through Day 6, and increase at the direction of the DLRM to 6 mg on Day 7, while the dose of nadolol may increase daily from 1 mg on Day 2 through 5 mg on both Day 6 and Day 7.

Part D will be initiated after DLRM review of safety and PK (where available) data through at least Day 4 from the first cohort in Part B. Enrollment into Part D will commence after DLRM review.

‡ One CSF sample will be collected from each subject in this cohort for determination of concentrations of Compound 03-5 and nadolol (if relevant): at approximately 2 hours after dosing on Day 2 from 4 subjects, and at approximately 2 hours after dosing on Day 6 from the remaining 4 subjects.

Eight healthy subjects aged 18-50 years were enrolled into Cohort D1 and received escalating doses of Compound 03-5 (3-12 mg) administered once daily 2 hours follow pre-administration of nadolol (1-40 mg). On all dosing days, study drug(s) were administered orally after an overnight fast of at least 8 hours.

Routine measures of ECG, vital signs, safety labs, physical exams and plasma sample collections for analysis of drug pharmacokinetics (PK) were undertaken according to the Schedule of Events (Table 1). A single sample of cerebrospinal fluid (CSF) was collected from 7 of the 8 subjects enrolled in Cohort D1 for determination of concentrations of Compound 03-5 and nadolol on either Day 2 (N=3) or Day 6 (N=4).

TABLE 2

Schedule of Events for Cohort D1

| | Screening Day −28 to −2 | Day −1 | Day 1 | Day 2 | Day 3 | Day 4 | Day 5 | Day 6 | Day 7 | Day 8 | Day 9 | EOS Day 15[12] |
|---|---|---|---|---|---|---|---|---|---|---|---|---|
| Outpatient visit | X | | | | | | | | | | | X |
| In-patient admission[1] | | X | | | | | | | | | | |
| In-patient stay | | | X | X | X | X | X | X | X | X | | |
| Discharge[2] | | | | | | | | | | | X | |
| Informed consent[3] | X | | | | | | | | | | | |
| Evaluate Inclusion/Exclusion criteria | X | X | | | | | | | | | | |
| Medical history | X | | | | | | | | | | | |
| Urine tests for drugs, cotinine | X | X | | | | | | | | | | |
| Alcohol breath test | X | X | | | | | | | | | | |
| Hepatitis and HIV serologies | X | | | | | | | | | | | |
| Evaluation of SARS-CoV-2 infection[4] | X | X | | | | | | | | | | |
| Height, weight | X | | | | | | | | | | | |
| Serum pregnancy or FSH test[5] | X | | | | | | | | | | | |
| Urine pregnancy test[5] | | X | | | | | | | | | | X |
| Compound 03-5 administration[13] | | | X | X | X | X | X | X | X | | | |
| nadolol administration[13] | | | X | X | X | X | X | X | X | | | |
| Vital signs[6] | X | X | X | X | X | X | X | X | X | X | X | X |
| Physical exam, complete | X | | | | | | | | | | | X |
| Physical exam, abbreviated | | X | X[11] | | X[11] | | | | | | X | |
| Safety labs[7] | X | X | X | X | X | X | X | X | X | | X | X |
| ECG[8] | X | X | X | X | X | X | X | X | X | X | X | X |
| Assessment of AEs | | X | X | X | X | X | X | X | X | X | X | X |
| Concomitant medications | X | X | X | X | X | X | X | X | X | X | X | X |
| Plasma PK sample collection[9] | | | X | X | X | X | X | X | X | X | X | |
| CSF PK sample collection[10] | | | | X | | | | X | | | | |

AE = adverse event; ECG = electrocardiogram; HIV = human immunodeficiency virus, PK = pharmacokinetics; EOS = End of Study

[1]Subjects were admitted on Day −1.

[2]Subjects were discharged on the afternoon of Day 9.

[3]Informed consent was obtained before any study-related procedures are performed.

[4]SARS-CoV-2 evaluation included testing from throat or nasal swab for current infection at Screening, and/or evaluation of possible ongoing infection based on body temperature (>37.3° C.), blood oxygen (<90 %) and Investigator judgement at the start of confinement.

[5]For females of childbearing potential, a serum β-hCG pregnancy test was performed at screening, and urine dipstick test was performed on Day −1 and at EOS. For postmenopausal women, an FSH test will be performed at Screening.

[6]Vital signs including temperature, respirations, triplicate blood pressure, and triplicate heart rate measurements (done 3 times separated by approximately 1 minute in supine position) were assessed after the subject had been at rest in the supine position for at least 5 minutes on Day −1 and at the times identified below.

At Screening and on Day −1

On Day 1 through Day 7: twice within 1 hour prior to dosing nadolol, twice within 1 hour prior to the daily dose of Compound 03-5, and after the first daily dose of Compound 03-5 at hour 0.25 ± 0.1, 0.5 ± 0.25, 1 ± 0.25, 2 ± 0.25, 4 ± 0.5, 8 ± 1 and 12 ± 1.

On Day 8 at 24 ± 1 hours after the last dose of Compound 03-5

On Day 9 at 48 ± 2 hours after the last dose of Compound 03-5

TABLE 2-continued

| Schedule of Events for Cohort D1 | | | | | | | | | | | | |
|---|---|---|---|---|---|---|---|---|---|---|---|---|
| | Screening Day −28 to −2 | Day −1 | Day 1 | Day 2 | Day 3 | Day 4 | Day 5 | Day 6 | Day 7 | Day 8 | Day 9 | EOS Day 15[12] |

Day 15 (EOS) at any time during the site visit

[7]Safety labs, including hematology, clinical chemistries, urinalysis, and cardiac troponin, were evaluated at 2-6 hours after administration of Compound 03-5 Days 1, 2, 4, and 7, and at any time of day on all other scheduled assessment days.

[8]Triplicate ECGs were obtained at the times listed below. Unless otherwise stated, subjects will be required to rest in a supine position for at least 5 minutes prior to the recording of ECG.

At screening;

on Day −1 at the same times of day as planned for Day 1 (±0.5 hours);

On Day 1 through Day 7: twice within 1 hour prior to dosing nadolol, twice within 1 hour prior to the daily dose of Compound 03-5, and after the daily dose of Compound 03-5 at hour 0.25 ± 0.1, 0.5 ± 0.25, 1 ± 0.25, 2 ± 0.25, 3 ± 0.5, 4 ± 0.5, 6 ± 0.5, 8 ± 1,10 ± 1, 12 ± 1, and 14 ± 1;

On Day 8: 24 ± 1 and 36 ± 1 hours after the last dose of Compound 03-5 on Day 7;

On Day 9: 48 ± 2 hours after the last dose of Compound 03-5;

Day 15 (EOS) at any time during the site visit.

[9]Plasma PK samples were collected for analysis of Compound 03-5 and nadolol concentrations at the following times:

On Days 1 through 7 within 1 hour prior to first dose of nadolol (if administered), within 0.5 hour prior to first dose of Compound 03-5 and after the first dose of Compound 03-5 at hour 0.25 ± 0.1, 0.5 ± 0.1, 1 ± 0.25, 2 ± 0.5 (to be collected within 30 minutes of the CSF sample), 4 ± 0.5, 6 ± 1, and 12 ± 1;

On Day 8: at 24 (±1) and 36 (±1) hours after the last dose of Compound 03-5;

And on Day 9 at 48 (±2) hours after the last dose of Compound 03-5.

[10]A single CSF sample was collected from each subject enrolled in this cohort for determination of concentrations of Compound 03-5 and nadolol.

Attempted from 4 subjects, but successfully collected in only 3 subjects at 2 ± 0.5 hours after dosing on Day 2.

from the remaining 4 subjects at approximately 2 ± 0.5 after dosing on Day 6.

A time-matched plasma PK sample was collected within ± 0.5 hours of the CSF collection.

[11]An abbreviated physical exam was conducted at the time of the predicted $C_{max}$ at 2 hours after dosing (or within a 4-hour window thereafter) on Day 1.

[12]End of Study (EOS) was conducted on Day 15 ± 3 days.

[13]nadolol (1-40 mg) was pre-administered 2 hour before Compound 03-5 (3-12 mg) on each of the 7 dosing days according to the dose escalation plan provided in the Study Schematic.

A. Cohort D2.

In Cohort D2, 8 healthy volunteers aged 55-75 years were admitted on Day −1 for a 5-day confinement period at the research facility. During this confinement, subjects received escalating doses of open label Compound 03-5 (1-10 mg) once-daily from Day 1 through Day 3 2 hours after pre-administration of open-label nadolol (3 mg) one each for the 3 dosing days according to the the following schematic. Subjects remained in-residency until all study procedures are completed on Day 4.

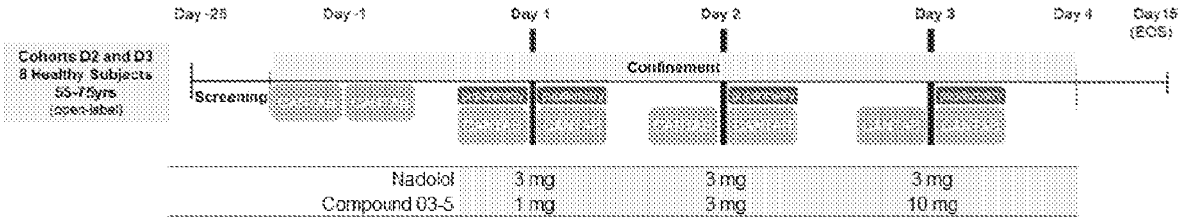
Day -25
Day -1
Day 1
Day 2
Day 3
Day 4
Day 15
(EOS)
Cohorts D2 and D3
8 Healthy Subjects
55-75yrs
(open-label)
Confinement
Screening
Nadolol
3 mg
3 mg
3 mg
Compound 03-5
1 mg
3 mg
10 mg Compound 03-5 dose administration. Compound 03-5 was administered as escalating doses on Day 1 (1 mg), Day 2 (3 mg) and Day 3 (10 mg). CANTAB was conducted twice in all subjects on the day prior to start of dosing (Day −1) to familiarize subjects with the platform, and prior to dosing and approximately 3 hours after Compound 03-5 administration on Days 1, 2, and 3.

TABLE 3

Schedule of Events for Cohort D2

| | Screening Day −28 to −2 | Day −1 | Day 1 | Day 2 | Day 3 | Day 4 | EOS Day 15[15] |
|---|---|---|---|---|---|---|---|
| Outpatient visit | X | | | | | | X |
| In-patient admission[1] | | X | | | | | |
| In-patient stay | | | X | X | X | | |
| Discharge[2] | | | | | | X | |
| Informed consent[3] | X | | | | | | |
| Evaluate Inclusion/Exclusion criteria | X | X | | | | | |
| Medical history | X | | | | | | |
| Urine tests for drugs, cotinine | X | X | | | | | |
| Alcohol breath test | X | X | | | | | |
| Hepatitis and HIV serologies | X | | | | | | |
| Evaluation of SARS-CoV-2 infection[4] | X | X | | | | | |
| Height, weight | X | | | | | | |
| Serum pregnancy or FSH test[5] | X | | | | | | |
| Urine pregnancy test[5] | | X | | | | | X |
| Study drug administration (Compound 03-5 dose escalation with nadolol)[6] | | | X | X | X | | |
| CANTAB[7] | | X | X | X | X | | |
| Pupillometry[9] | | | X | X | X | | |
| Vital signs[10] | X | X | X | X | X | X | X |
| Physical exam, complete | X | | | | | | X |
| Physical exam, abbreviated[11] | | X | X | X | X | X | |
| Safety labs[12] | X | X | X | X | X | X | X |
| ECG[13] | X | X | X | X | X | X | X |
| Assessment of AEs | | X | X | X | X | X | |
| Concomitant medications | X | X | X | X | X | X | X |
| Plasma PK sample collection[14] | | | X | X | X | X | |

AE = adverse event; ECG = electrocardiogram; HIV = human immunodeficiency virus, PK = pharmacokinetics; EOS = End of Study

[1]Subjects were admitted on Day −1.

[2]Subjects were discharged on the afternoon of Day 4.

[3]Informed consent was obtained before any study-related procedures are performed.

[4]SARS-CoV-2 evaluation included testing from throat or nasal swab for current infection at Screening, and/or evaluation of possible ongoing infection based on body temperature (>37.3° C.), blood oxygen (<90%) and Investigator judgement at the start of confinement.

[5]For females of childbearing potential, a serum β-hCG pregnancy test was performed at screening, and urine dipstick test was performed on Day −1 and at EOS. For postmenopausal women, an FSH test will be performed at Screening.

[6]nadolol (3 mg) was pre-administered 2 hour before Compound 03-5. Compound 03-5 was administered once daily as escalating doses of 1, 3, 10 mg on Day 1, Day 2 and Day 3.

[7]CANTAB was administered twice on Day −1, once to familiarize the subject with the tests and equipment, and a second time at least 3 hours later (as a pre-dose measure). On Days 1, 2, and 3, CANTAB was administered within 2 hours prior to administration of nadolol, and repeated starting 3 ± 1 hours after dosing of Compound 03-5.

[9]Pupillary light reflex was measured twice for each eye at the following times at sites where operationally feasible:

On Day 1: prior to dosing and at 2 ± 0.5, 4 ± 2 and 6 ± 1 hours after last administration of Compound 03-5 on Day 1

On Day 2: at 2 ± 0.5, 4 ± 2 and 6 ± 1 hours after last administration of Compound 03-5 on Day 2

On Day 3: at 2 ± 0.5, 4 ± 2 and 6 ± 1 hours after last administration of Compound 03-5 on Day 3

[10]Vital signs including temperature, respirations, triplicate blood pressure, and triplicate heart rate measurements (done 3 times separated by approximately 1 minute in supine position) were assessed after the subject had been at rest in the supine position for at least 5 minutes on Day −1 and at the times identified below.

At Screening and on Day −1

On Day 1, Day 2 and Day 3: once within 2 hours prior to dosing nadolol, once within 1 hour prior to the daily dose of Compound 03-5, and after the daily dose of Compound 03-5 at hour 1 ± 0.25, 2 ± 0.25, 3 ± 0.5, 4 ± 0.5, 5 ± 1, 6 ± 1, 7 ± 1, 8 ± 1, 9 ± 1, and 10 ± 1.

On Day 4: at 24 ± 1 hour after the last administration of Compound 03-5 on Day 3.

Day 15 (EOS) at any time during the site visit

[11]An abbreviated physical exam was conducted at 2 hours after the first administration of Compound 03-5 or within a 4-hour window thereafter on Days 1, 2, and 3.

[12]Safety labs, including standard panels for hematology, clinical chemistries, urinalysis, and cardiac troponin were evaluated between 2-to 6 hours after administration of Compound 03-5 on Days 1, 2, and 3, and at any time of day on Day 15 (EOS).

[13]Triplicate ECGs obtained at the times listed below. Subjects were in a supine position for at least 5 minutes prior to the recording of ECG.

At screening;

on Day −1 at the same times of day as planned for Day 1 (±0.5 hours).

On Day 1, Day 2 and Day 3: once within 2 hours prior dosing nadolol, once within 2 hour priors to the daily dose of Compound 03-5, and after the daily dose of Compound 03-5 at hour 0.25 ± 0.2, 0.5 ± 0.25, 1 ± 0.25, 2 ± 0.25, 3 ± 0.5, 4 ± 0.5, 5 ± 1, 6 ± 1, 7 ± 1, 8 ± 1, 9 ± 1, and 10 ± 1;

On Day 4: at 24 ± 1 hour and 30 ± 1 after the last administration of Compound 03-5 on Day 3;

Day 15 (EOS) at any time during the site visit.

[14]Plasma PK samples were collected for analysis of Compound 03-5 and nadolol at the following times:

On Days 1,2, and 3 within 1 hour prior to dosing of nadolol, within 0.5 hour prior to dosing of Compound 03-5 and at the following times after the first daily dose of Compound 03-5 1 ± 0.25, 2 ± 0.25, 4 ± 0.5, and 6 ± 1.

On Day 4: at 24 ± 1 and 30 ± 1 hour after the last administration of Compound 03-5 on Day 3.

[15]End of Study (EOS) visit was conducted on Day 15 ± 5 days. .

Results.

Figure 11A:
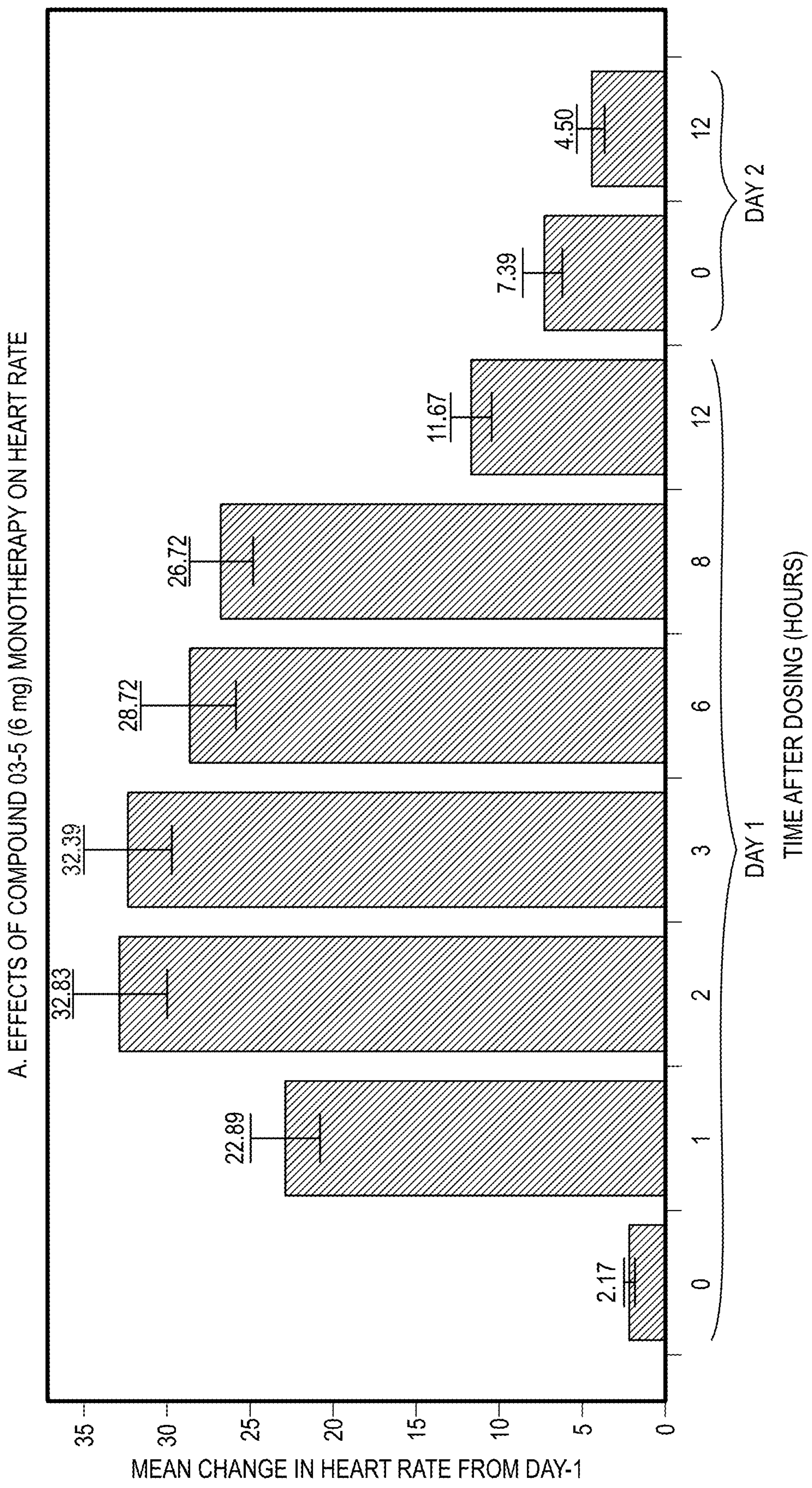
FIGS. 11A-11B show the effects of Compound 03-5 monotherapy (6 mg) on heart rate (FIG. 11A) and administered 2 hours after nadolol (1-40 mg) (FIG. 11B). Heart rate was measured by triplicate ECG recordings. Data are presented as means changes from time-matched measures recorded on the day before the first dose of study drug (Day −1).
Figure 11B:
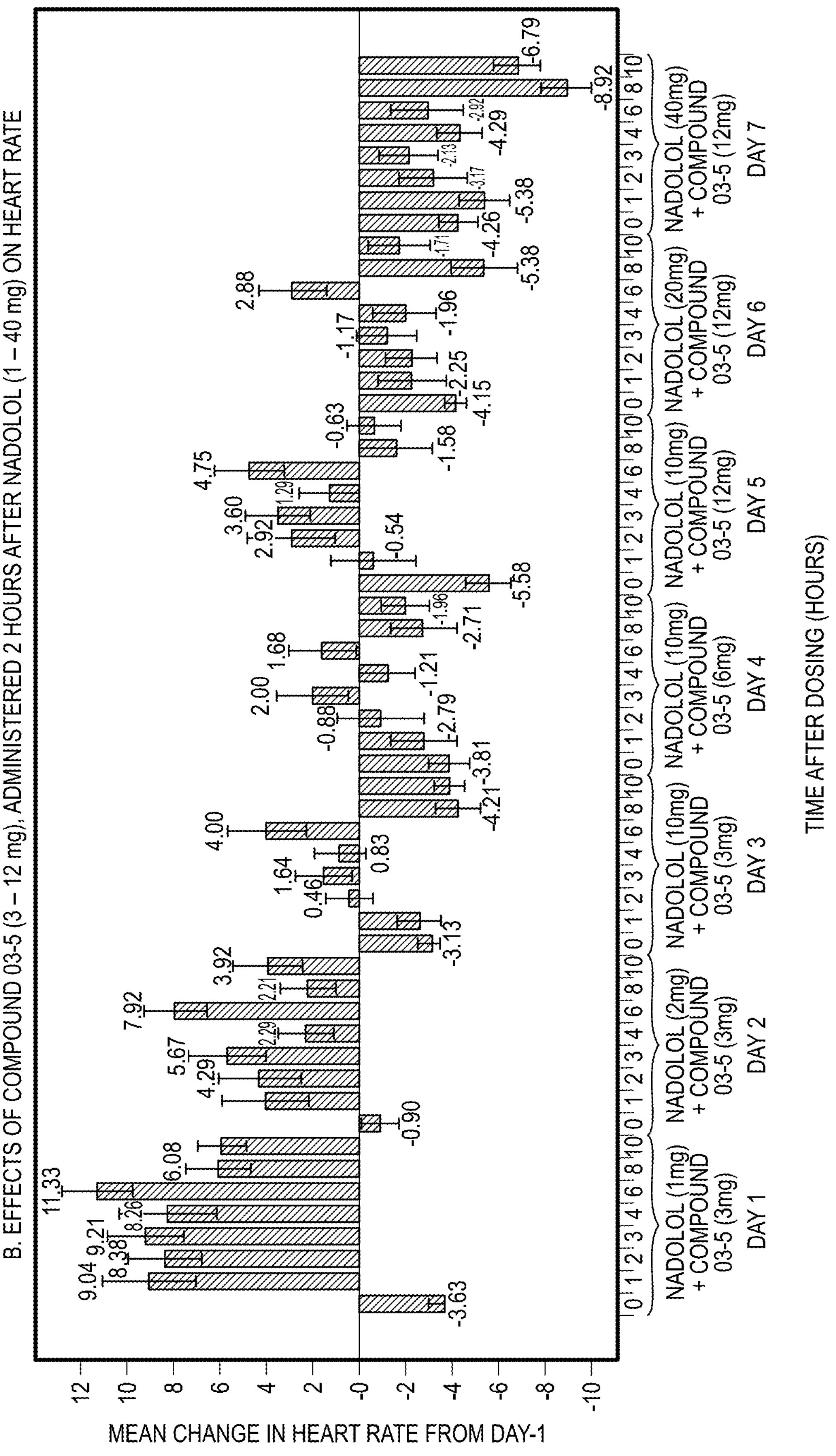

In earlier cohorts, maximum mean increases in heart rate up to approximately 30 beats per minute were observed following monotherapy with 6 mg Compound 03-5. FIG. 11. This effect was substantially attenuated to a mean maximum increase of 7 beats per minute by pre-administration of 1 mg nadolol. Concomitant attenuation of the effects of Compound 03-5 on blood glucose and potassium, tachycardia, tremor and palpitations was also noted. These effects of Compound 03-5 are similar to the widely reported responses reported with marketed $\beta_2$-AR agonists such as salbutamol.

Figure 12:
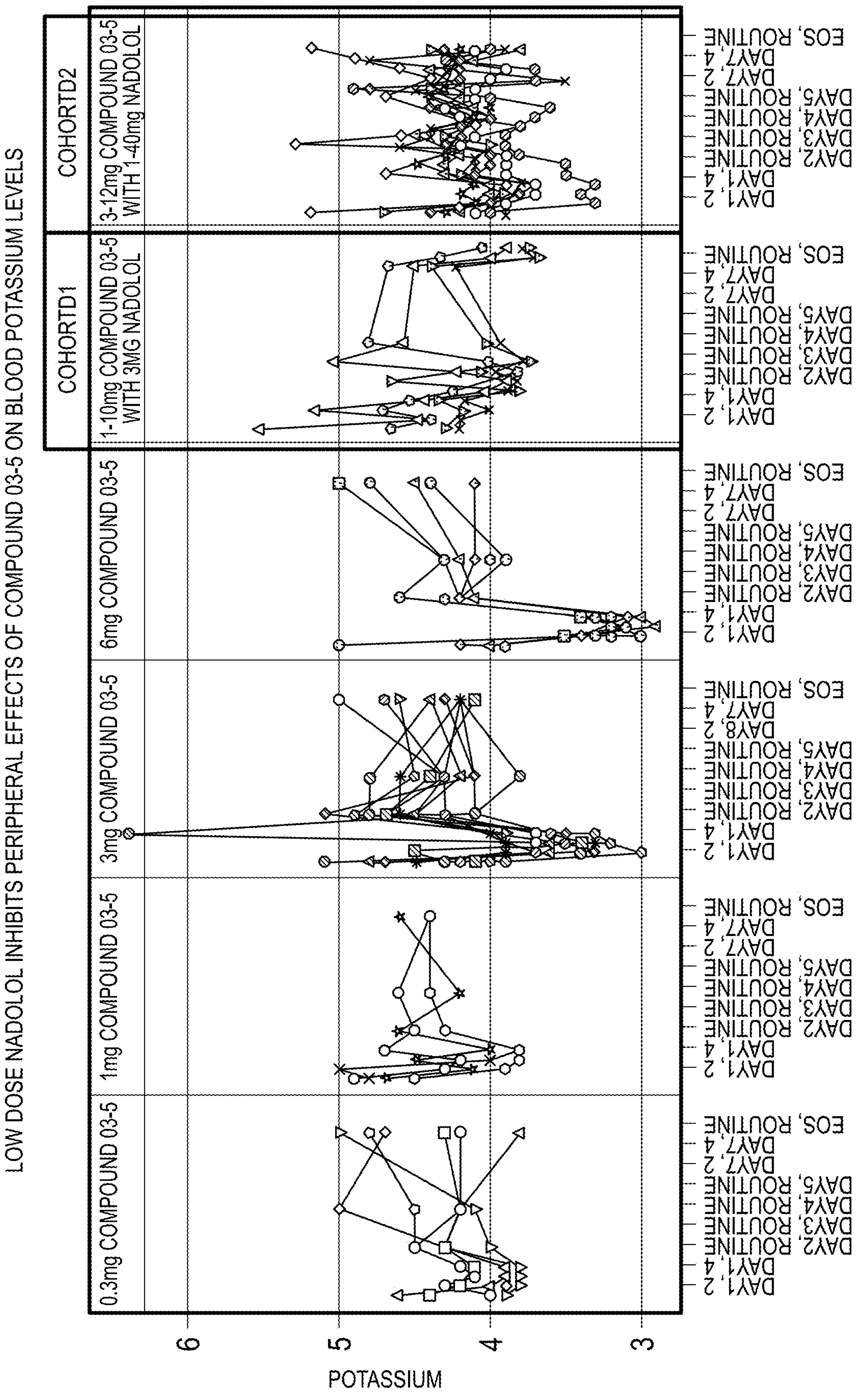
FIG. 12 shows low dose nadolol Inhibits Peripheral effects of Compound 03-5 on blood potassium levels Dose-dependent increases in hypokalemia receiving Compound 03-5 monotherapy (0.3 mg-6 mg) in Cohorts A1, A2, A3, A4 and A5, and attenuation of hypokalemia in subjects dosed with nadolol (1-40 mg) in Cohorts D1 and D2. Data are presented as individual observations for all available subjects.

In Cohort D1, as with other cohorts, pre-administration of 1 mg nadolol substantially attenuated the effects of Compound 03-5, administered orally at doses up to 6 mg, to increase heart rate and other peripheral effects of Compound 03-5 including hyper glycemia and hypokalemia. FIG. 11 and FIG. 12.

Figure 13:
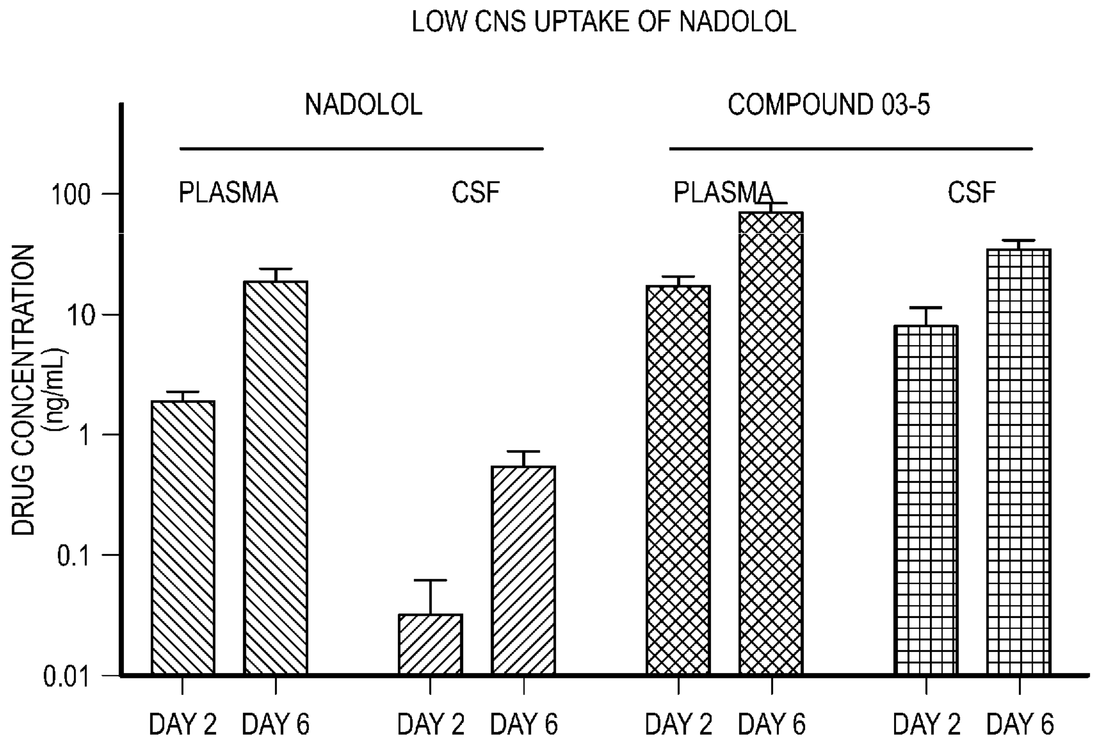
FIG. 13 is a chart showing low CNS uptake of nadolol. Time-matched concentrations for Compound 03-5 and nadolol in plasma and cerebrospinal fluid (CSF) from subjects in Cohort D1 were determined in samples collected after administration of nadolol and Compound 03-5 on Day 2 (N=3-4 subjects) and Day 6 (N=4 subjects). Data are presented as mean±SEM observations from N=3-4 subjects per dose level.
Figure 14:
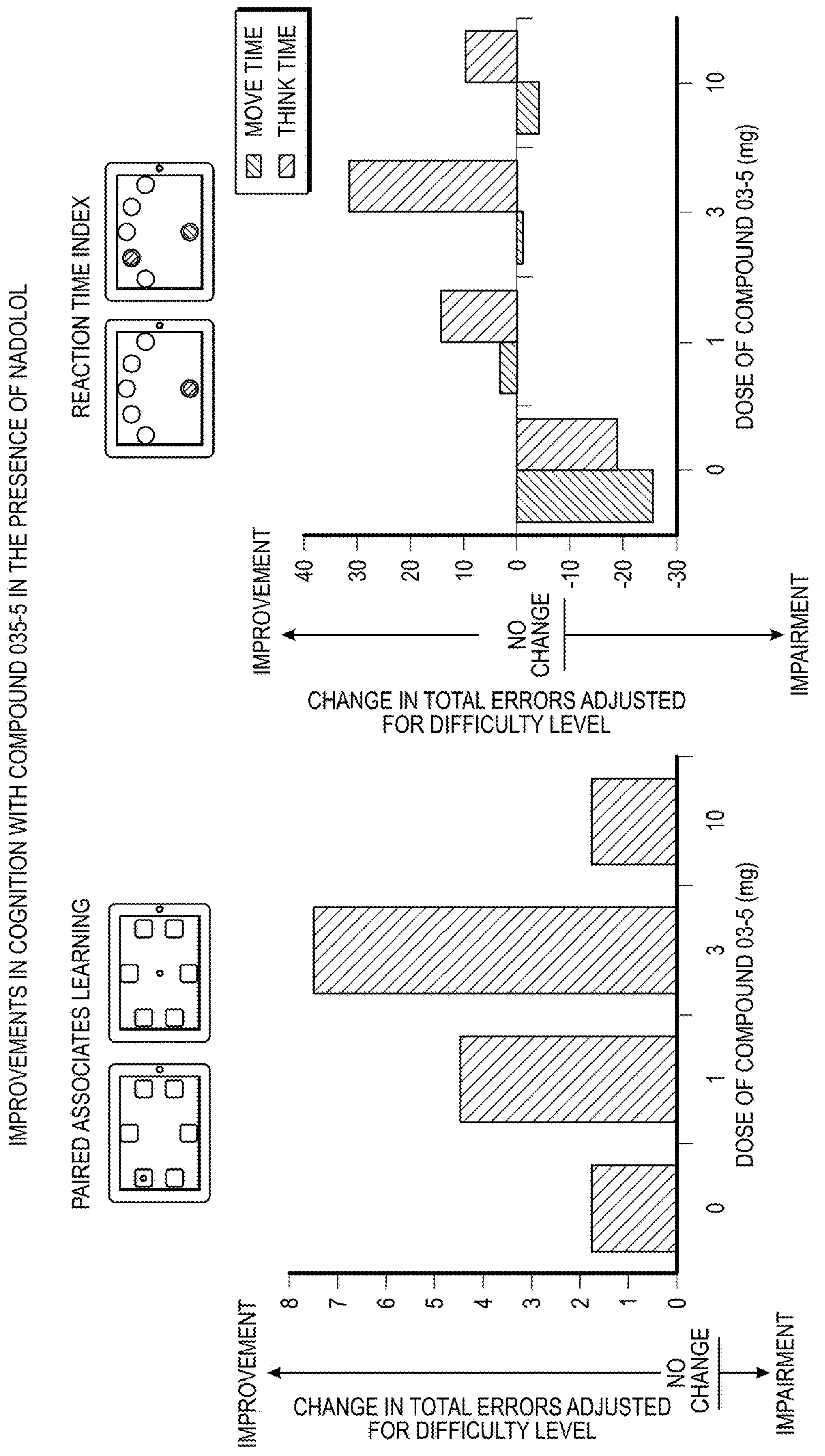
FIG. 14 shows improvements in cognition with Compound 03-5 in the presence of nadolol. CANTAB data from healthy adults 55-75 years of age (N=4) who received once-daily 3 mg nadolol and Compound 03-5 (1, 3, and 10 mg) on Day1, Day 2 and Day 3. Data show all available data in Cohort D2 (N=4 on Apr. 22, 2021) for 2 of the tests in the CANTAB battery. Data are presented as mean changes from the within-day pre-dose assessment.

Drug concentrations in cerebrospinal fluid (CSF) of subjects enrolled in Cohort D1 were measured after they received Compound 03-5 (3 mg [N=3] or 12 mg [N=4]), and nadolol (2 mg [N=3] or 20 mg ([N=4]). The estimated concentrations of nadolol in CSF demonstrate that it is substantially peripherally restricted with approximately 2-3% of time-matched plasma concentration detected. In contrast, the concentrations of Compound 03-5 in CSF were approximately 50% of the time-matched plasma concentration. FIG. 13.

Conclusion.

Nadolol is approved for treatment at doses in humans from 40 mg up to 320 mg/day.

In earlier cohorts, maximum mean increases in heart rate up to approximately 20 beats per minute were observed following monotherapy with 6 mg Compound 03-5. This effect was substantially attenuated to a mean maximum increase of 7 beats per minute by pre-administration of 1 mg nadolol.

In Cohort D1, pre-administered nadolol (1 mg up to 40 mg) blocked the peripheral effects of Compound 03-5 (3-12 mg) on heart rate, glucose, potassium, and other clinical observations associated with $\beta_2$-AR agonists such as tachycardia, tremor and palpitations. Emerging preliminary data on CSF concentrations of nadolol in Cohort D1 of this study demonstrate that nadolol is a β-AR antagonist with very low CNS penetration.

In Cohort D2, pre-administered nadolol (3 mg) similarly blocked the peripheral effects of Compound 03-5 (1-10 mg) on heart rate, etc. However, improvements in performance in the CANTAB cognition battery were observed and are presumed mediated by the selective stimulation of $\beta_2$-ARs in the brain by Compound 03-5.

The effects of low dose nadolol (3 mg) to control untoward peripheral effects of the selective b2-AR agonist, without inhibiting the pro-cognitive central effects, coupled with the evidence of low CNS penetration of nadolol observed in Cohort D1, support the use of low dose nadolol for specific and selective control of peripheral effects of $\beta_2$-AR agonists intended for treatment of CNS diseases.

Example 7: A Study of COMPOUND 03-5 and NADOLOL in Subjects with Mild Cognitive Impairment or Mild Dementia Due to Parkinson's or Alzheimer's Disease Healthy volunteers were be enrolled into 2 cohorts in a study to undertake within-subject dose titration of Compound 03-5 and/or nadolol in order to explore doses/dose combinations that mitigate peripheral effects of Compound 03-5, e.g. on heart rate, while preserving possible central effects of Compound 03-5 on cerebral perfusion and pupillary light reflex.

Study Description

Brief Summary: This is a Phase 2a, randomized, placebo-controlled, double-blind, crossover study to evaluate the effects COMPOUND 03-5 administered with NADOLOL on cognition in subjects with Mild Cognitive Impairment (MCI) or mild dementia.

Detailed Description: Approximately 40 subjects will be enrolled in a 2 period, 2-way crossover design following study eligibility confirmation during the screening period. During each treatment period, subjects will receive daily doses of COMPOUND 03-5 administered with NADOLOL or matching placebo for 14 days. Each treatment period will be separated by a washout period of 7 days. All subjects will complete clinical, cognitive and pharmacodynamic assessments during each treatment period. PK blood samples will be collected prior to, during and after study medication administration.

Conditions

Conditions: Mild Cognitive Impairment, Dementia.

Study Design

Study Type: Interventional

Primary Purpose: Treatment

Study Phase: Phase 2

Interventional Study Model: Crossover Assignment

Number of Arms: 4

Masking: Quadruple (Participant, Care Provider, Investigator, Outcomes Assessor)

Allocation: Randomized

Enrollment: 40 [Anticipated].

Arms and Interventions

| ARMS | INTERVENTIONS |
|---|---|
| Experimental: COMPOUND 03-5 (3 mg)/NADOLOL (3 mg) to Placebo<br>Subjects will receive daily doses of COMPOUND 03-5 (3 mg) co-administered with NADOLOL (3 mg) for 14 days, followed by a washout period of no drug for 7 days, followed by matching placebo for COMPOUND 03-5 and matching placebo for NADOLOL for 14 days. | Drug: COMPOUND 03-5, matching placebo for COMPOUND 03-5,<br>NADOLOL, matching placebo for NADOLOL<br>COMPOUND 03-5 and matching placebo white tablets,<br>NADOLOL and matching placebo yellow tablets |
| Experimental: Placebo to COMPOUND 03-5 (3 mg)/NADOLOL (3 mg)<br>Subjects will receive matching placebo for COMPOUND 03-5 and matching placebo for NADOLOL for 14 days | Drug: COMPOUND 03-5, matching placebo for COMPOUND 03-5,<br>NADOLOL, matching placebo for NADOLOL<br>COMPOUND 03-5 and matching placebo white tablets,<br>NADOLOL and matching placebo yellow tablets |

-continued

| ARMS | INTERVENTIONS |
|---|---|
| followed by a washout period of no drug for 7 days, followed by daily doses of COMPOUND 03-5 (3 mg) coadministered with NADOLOL (3 mg) for 14 days. | |
| Experimental: COMPOUND 03-5 (6 mg)/NADOLOL (3 mg) to Placebo Subjects will receive daily doses of COMPOUND 03-5 (6 mg) co-administered with NADOLOL (3 mg) for 14 days, followed by a washout period of no drug for 7 days, followed by matching placebo for COMPOUND 03-5 and matching placebo for NADOLOL for 14 days. | Drug: COMPOUND 03-5, matching placebo for COMPOUND 03-5, NADOLOL, matching placebo for NADOLOL COMPOUND 03-5 and matching placebo white tablets, NADOLOL and matching placebo yellow tablets |
| Experimental: Placebo to COMPOUND 03-5 (6 mg)/NADOLOL (3 mg) Subjects will receive matching placebo for COMPOUND 03-5 and matching placebo for NADOLOL for 14 days followed by a washout period of no drug for 7 days, followed by daily doses of COMPOUND 03-5 (6 mg) coadministered with NADOLOL (3 mg) for 14 days. | Drug: COMPOUND 03-5, matching placebo for COMPOUND 03-5, NADOLOL, matching placebo for NADOLOL COMPOUND 03-5 and matching placebo white tablets, NADOLOL and matching placebo yellow tablets |

Outcome Measures

Primary Outcome Measure:

1. Treatment-emergent adverse events

The number of subjects experiencing treatment-emergent adverse events after receiving COMPOUND 03-5 doses of 3 mg and 6 mg co-administered with a NADOLOL dose of 3 mg compared to placebo

[Time Frame: Days 1, 7, and 14 of each treatment period (two 14-day periods)]

2. Vital Signs

Change from Baseline in supine blood pressure (diastolic blood pressure and systolic blood pressure) after COMPOUND 03-5 doses of 1 mg and 6 mg co-administered with a NADOLOL dose of 3 mg compared to placebo

[Time Frame: Days 1, 7, and 14 of each treatment period (two 14-day periods)]

3. Electrocardiograms (ECGs)

Change from Baseline in QTc interval using the Fredericia (QTcF) and Bazett (QTcB) corrections after COMPOUND 03-5 doses of 1 mg and 6 mg co-administered with a CST107 dose of 3 mg compared to placebo

[Time Frame: Days 1, 7, and 14 of each treatment period (two 14-day periods)]

Secondary Outcome Measure.

4. Change from Baseline in CANTAB Reaction Time Task

Measures changes in cognition by testing psychomotor speed (selecting a flashing circle on a touch tablet screen as quickly as possible).

[Time Frame: Days 1, 7, and 14 of each treatment period (two 14-day periods)]

5. Change from Baseline in CANTAB Rapid Visual Information Processing

Measures changes in cognition by testing sustained attention, response accuracy, target sensitivity and reaction times. Single digits appear in random order in the center of a touch tablet screen and subjects must detect a series of 3-digit target sequences and respond by touching the button at the bottom of the screen when they see the final number of the sequence.

[Time Frame: Days 1, 7, and 14 of each treatment period (two 14-day periods)]

6. Change from Baseline in CANTAB Verbal Recognition Memory

Measures changes in cognition by testing memory (recall of 18 words flashed onto a touch tablet screen).

[Time Frame: Days 1, 7, and 14 of each treatment period (two 14-day periods)]

7. Change from Baseline in CANTAB Adaptive Tracking Task

Measures changes in visual and motor coordination and vigilance. In this task, a small circle (target) continuously moves across the screen in a semi-randomized fashion, so as to minimize the subject's ability to predict the trajectory of the target. The subject is instructed to use his/her finger on the touch screen to move a small dot so that it is consistently within the center of the moving target on the screen. During the test, the speed of the circle is adjusted in response to the subject's ability to keep the dot in the circle, ensuring that the test is adapted to the individual subject.

[Time Frame: Days 1, 7, and 14 of each treatment period (two 14-day periods)]

8. Change from Baseline in CANTAB Paired Associates Learning Test

Measures changes in cognition by testing attention (remembering the location of an abstract pattern on a touch tablet screen).

[Time Frame: Days 1, 7, and 14 of each treatment period (two 14-day periods)]

9. Change from Baseline in CANTAB Stop Signal Task

Measures response inhibition (impulse control). Subjects must respond to an arrow stimulus by selecting one of two options, depending on the direction in which the arrow points. If an audio tone is present, subjects must withhold making that response (inhibition).

[Time Frame: Days 1, 7, and 14 of each treatment period (two 14-day periods)]

10. Change from Baseline in Negative Emotional Bias in the Facial Expression Recognition Task (FERT)

Faces with six different basic emotions (happiness, fear, anger, disgust, sadness, surprise) are briefly displayed on a screen and participants are required to indicate the expression of the face via a button-press.

[Time Frame: Days 1, 7, and 14 of each treatment period (two 14-day periods)]

Eligibility

Minimum Age: 50 Years

Maximum Age: 90 Years

Sex: All

Gender Based: No

Accepts Healthy Volunteers: No

Criteria: Inclusion Criteria:

Male or female subjects ≥50 and ≤90 years of age at time of informed consent.

Diagnosis of mild cognitive impairment OR mild dementia due to either: Parkinson's disease associated with REM sleep behavior disorder (RBD+PD) and positive response to the RBD Single-Question Screen (RBD1Q) and without hallucinations; OR Alzheimer's Disease (AD).

For subjects taking anti-Parkinsonian medication: stable daily dosing for at least 1 month prior to Screening and through the End of Study If the subject is taking a single drug for AD (e.g., donepezil or other cholinesterase inhibitors or memantine; dual therapy is excluded), they must have been on a stable dose for at least 2 months prior to Day 1, and the dose must remain unchanged during the study unless required for management of adverse events (AEs).

Cognitive decline not primarily caused by traumatic, or medical problems (alternative causes of cognitive decline are ruled out).

Adequate visual and auditory abilities to perform all aspects of the cognitive and functional assessments.

Has a spouse or caregiver who can accompany the subject at specified study visits (if required based on cognitive function).

A score of greater than or equal to one standard deviation below age and educational norms in the Digit Symbol Substitution Test (DSST) during screening or within 6 months prior to Screening.

Montreal Cognitive Assessment (MoCA) score ≥18 and ≤26.

Adaptive criteria for enrollment based on the locus ceruleus (LC) neuromelanin sensitive magnetic resonance imaging (NM-MRI) contrastto-noise ratio (CNR).

Unless confirmed to be azoospermic (vasectomized or secondary to medical cause), males must agree to use a male condom from Day 1 until the follow-up visit when having penile-vaginal intercourse with a woman of childbearing potential who is not currently pregnant. Note: Men with a pregnant or breastfeeding partner must agree to remain abstinent from penile-vaginal intercourse or use a condom during each episode of penile vaginal penetration until after the Follow-Up Visit.

Females of childbearing potential (i.e., not postmenopausal or surgically sterile) who have a male partner must have a negative serum pregnancy test result and must agree to one of the following from start of Screening through 30 days after the last study medication administration: use a highly effective method of birth control; or monogamous relationship with a male partner of confirmed sterility; or practice complete abstinence.

Females of non-childbearing potential may be enrolled if it is documented that they are postmenopausal.

Body weight greater or equal to 50 kg and body mass index (BMI) between 18 and 35 kg/m2, inclusive at Screening.

Stable medical conditions for 3 months prior to Screening visit (e.g., controlled hypertension, dyslipidemia).

Willing to follow the protocol requirements and comply with protocol restrictions.

Capable of providing informed consent and complying with study procedures.

Criteria: Exclusion Criteria:

Subjects with poorly controlled hypertension despite lifestyle modifications and/or pharmacotherapy.

Subjects with pulmonary disease, including asthma if requiring the use of a β2-adrenergic bronchodilator, or evidence of clinically significant moderate or severe pulmonary symptoms.

Clinical signs indicating syndromes such as corticobasal degeneration, supranuclear gaze palsy, multiple system atrophy, chronic traumatic encephalopathy, signs of frontotemporal dementia, history of stroke, head injury or encephalitis, cerebellar signs, early severe autonomic involvement, or Babinski sign.

Current evidence or history in the past two years of: epilepsy, focal brain lesion, head injury with loss of consciousness or meeting DSM-V diagnostic criteria for psychotic disorders, such as schizophrenia or bipolar disorder, or have unstable concomitant psychiatric symptomatology except for depressed mood.

Evidence of any significant clinical disorder or laboratory finding that renders the participant unsuitable for receiving an investigational drug including clinically significant or unstable hematologic, hepatic, cardiovascular, pulmonary, gastrointestinal, endocrine (including thyrotoxicosis, excluding managed hypo and hyperthyroidism), metabolic, renal, or other systemic disease or laboratory abnormality.

History of malignant disease within 5 years, including solid tumors and hematologic malignancies (except basal cell and squamous cell carcinomas of the of the skin that have been completely excised and are considered cured).

Any clinically significant illness or disease as determined by medical and surgical history, physical examination, 12-lead electrocardiogram (ECG) and clinical laboratory assessments conducted at Screening.

Clinically significant abnormalities of ECG, including QTcF>450 ms, for males and QTcF>470 ms for females, and/or HR<50 beats per minute, or evidence of clinically significant bundle branch blocks, as indicated by 12-lead ECG during the Screening Period.

A calculated creatinine clearance of ≤60 mL/min according to the Cockcroft-Gault equation.

Current use of any prohibited prescription medication, over-the-counter medication, or herbal supplements including green tea/products during Screening or throughout study, unless approved by both the Investigator and the Sponsor Medical Monitor.

Prior treatment with any investigational drug ≤90 days prior to dosing (Day 1), or ≤5 half-lives of the drug (whichever is longer), or current enrollment in any other study treatment or disease study, except for observational studies.

Known or suspected alcohol or substance abuse within the past 12 months and/or positive test for alcohol or drugs of abuse at Screening or Day 1.

Suicidal ideation with actual intent or plan ("Yes" answer on the C—SSRS ideation items 4 or 5) within 3 months prior to study Screening.

Positive screening test for hepatitis C antibody (HCV Ab) or current hepatitis B infection (defined as positive for hepatitis B surface antigen [HBsAg] at Screening). Subjects with immunity to hepatitis B (defined as negative HbsAg and positive hepatitis B surface antibody [HbsAb]) are eligible to participate in the study.

Positive screening test for human immunodeficiency virus (HIV).

Current infection with severe acute respiratory syndrome coronavirus 2 (SARS-CoV-2).

Females who are breastfeeding.

Any other reason for which the PI considers it is not in the best interest of the participant to undertake the study.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

All references referred to in the present disclosure are hereby incorporated by reference in their entirety. Various embodiments of the present disclosure may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the disclosure described above are intended to be merely exemplary; numerous variations and modifications will be apparent to those skilled in the art. All such variations and modifications are intended to be within the scope of the present disclosure as defined in any appended claims.

What is claimed is:

1. A method comprising: administering to a subject desiring improvement in cognitive function a β-agent and a peripherally acting β-blocker (PABRA), wherein the β-agent is Compound 03-5 administered at a 3 or 6 mg daily dose and the peripherally acting β-blocker (PABRA) is nadolol administered at a 3 mg daily dose.

2. The method of claim 1, wherein the Compound 03-5 is administered at a 6 mg daily dose and the peripherally acting β-blocker (PABRA) is nadolol administered at a 3 mg daily dose.

3. A method comprising: administering to a subject identified as having mild dementia and desiring improvement in cognitive function, a β-agent and a peripherally acting β-blocker (PABRA), wherein the PABRA is administered in a subtherapeutic dose, wherein the β-agent is Compound 03-5 administered at a 3 or 6 mg daily dose and the peripherally acting β-blocker (PABRA) is nadolol administered at a 3 mg daily dose.

4. A method comprising: administering to a subject having Parkinson's disease associated with REM sleep behavior disorder (RBD+PD) and/or positive response to RBD Single-Question Screen (RBD1Q) and desiring improvement in cognitive function, a β-agent and a peripherally acting β-blocker (PABRA), wherein the β-agent is Compound 03-5 administered at a 3 or 6 mg daily dose and the peripherally acting β-blocker (PABRA) is nadolol administered at a 3 mg daily dose.

5. The method of claim 4, wherein the patient does not have hallucinations.

6. A method comprising: administering to a subject having mild cognitive impairment (MCI) or mild dementia due to Parkinson's disease associated with REM sleep behavior disorder (RBD+PD) and/or positive response to RBD Single-Question Screen (RBD1Q) and desiring improvement in cognitive function, a β-agent and a peripherally acting β-blocker (PABRA), wherein the β-agent is Compound 03-5 administered at a 3 or 6 mg daily dose and the peripherally acting β-blocker (PABRA) is nadolol administered at a 3 mg daily dose.

7. The method of claims 1, 3, 4, or 6, wherein the β-agent is Compound 03-5 administered at a 3 mg daily dose and the peripherally acting β-blocker (PABRA) is nadolol administered at a 3 mg daily dose.

8. The method of claims 3, 4, or 6, wherein the β-agent is Compound 03-5 administered at a 6 mg daily dose and the peripherally acting β-blocker (PABRA) is nadolol administered at a 3 mg daily dose.

9. A method comprising: administering to a subject desiring improvement in cognitive function a β-agent and a peripherally acting β-blocker (PABRA), wherein: i) the β-agent is Compound 03-5 administered at a 0.3, 1, 3 or 6 mg daily dose and the peripherally acting β-blocker (PABRA) is nadolol administered at a 1 or 2 mg daily dose, or ii) the β-agent is Compound 03-5 administered at a 0.3 or 1 mg daily dose and the peripherally acting β-blocker (PABRA) is nadolol administered at a 3 mg daily dose.

* * * * *